(12) United States Patent
Jakobovits et al.

(10) Patent No.: US 11,135,245 B2
(45) Date of Patent: Oct. 5, 2021

(54) ENGINEERED γδ T-CELLS

(71) Applicant: Adicet Bio, Inc., South San Francisco, CA (US)

(72) Inventors: Aya Jakobovits, Beverly Hills, CA (US); Orit Foord, Foster City, CA (US); Andy An-deh Lin, Palo Alto, CA (US); Marianne Theresa Santaguida, Belmont, CA (US)

(73) Assignee: ADICET BIO, INC., Menlo Park, CA (US)

( * ) Notice: Subject to any disclaimer, the term of this patent is extended or adjusted under 35 U.S.C. 154(b) by 914 days.

(21) Appl. No.: 14/944,106

(22) Filed: Nov. 17, 2015

(65) Prior Publication Data

US 2016/0175358 A1    Jun. 23, 2016

Related U.S. Application Data

(60) Provisional application No. 62/080,500, filed on Nov. 17, 2014.

(51) Int. Cl.
| | | |
|---|---|---|
| *C12N 5/0783* | (2010.01) | |
| *A61K 35/17* | (2015.01) | |
| *C12N 15/00* | (2006.01) | |
| *A61K 39/00* | (2006.01) | |
| *C07K 14/705* | (2006.01) | |
| *C07K 14/74* | (2006.01) | |

(52) U.S. Cl.
CPC .......... *A61K 35/17* (2013.01); *A61K 39/0011* (2013.01); *C07K 14/70503* (2013.01); *C12N 5/0636* (2013.01); *C12N 15/00* (2013.01); *A61K 2039/5156* (2013.01); *A61K 2039/5158* (2013.01); *C07K 14/70539* (2013.01); *C12N 2501/2302* (2013.01); *C12N 2501/515* (2013.01); *C12N 2501/599* (2013.01); *C12N 2501/999* (2013.01)

(58) Field of Classification Search
None
See application file for complete search history.

(56) References Cited

U.S. PATENT DOCUMENTS

| | | |
|---|---|---|
| 5,185,250 A | 2/1993 | Brenner et al. |
| 5,260,223 A | 11/1993 | Brenner et al. |
| 7,728,114 B2 * | 6/2010 | Mach ...................... A61P 17/06 530/388.15 |
| 7,985,739 B2 | 7/2011 | Kay et al. |
| 9,540,448 B2 | 1/2017 | Scheinberg et al. |
| 2003/0138433 A1 | 7/2003 | Newell et al. |
| 2006/0026986 A1 | 1/2006 | Wang et al. |
| 2006/0122130 A1 | 6/2006 | Rabbani |
| 2006/0205089 A1 | 9/2006 | Dratz et al. |
| 2008/0026986 A1 | 1/2008 | Wang et al. |
| 2008/0171014 A1 * | 7/2008 | Wu ...................... C07K 16/244 424/85.2 |
| 2010/0272739 A1 | 10/2010 | Gelfand et al. |
| 2012/0034221 A1 | 2/2012 | Bonvini et al. |
| 2014/0141513 A1 | 5/2014 | De Carvalho Silva Santos et al. |
| 2015/0259645 A1 | 9/2015 | Inserm et al. |
| 2018/0169147 A1 * | 6/2018 | Anjos ..................... A61K 35/17 |

FOREIGN PATENT DOCUMENTS

| | | | |
|---|---|---|---|
| CN | | 1506456 A | 6/2004 |
| CN | | 102994448 A | 3/2013 |
| WO | WO | 1993/020221 A1 | 10/1993 |
| WO | WO | 2003/087341 A2 | 10/2003 |
| WO | WO | 2011/090804 A1 | 7/2011 |
| WO | WO | 2012/012667 A2 | 1/2012 |
| WO | WO | 2013/074916 A1 | 5/2013 |
| WO | WO | 2013/079174 A1 | 6/2013 |
| WO | WO | 2014/009370 A2 | 1/2014 |
| WO | WO | 2014/134412 A1 | 9/2014 |
| WO | WO | 2015/061694 A2 | 4/2015 |
| WO | WO | 2016/081518 A2 | 5/2016 |
| WO | WO | 2017/011804 A1 | 1/2017 |

OTHER PUBLICATIONS

Harlow et al., Antibodies, A Laboratory Manual, Cold Spring Harbor laboratory, 1988, pp. 37-47. (Year: 1988).*
Damschroder et al. (Mol Immunol. Aug. 2004;41(10):985-1000). (Year: 2004).*
Edwards et al. (J. Mol. Biol. (2003) 334, 103-118). (Year: 2003).*
Lloyd et al., Protein Engineering, Design & Selection vol. 22 No. 3 pp. 159-168, 2009. (Year: 2009).*
Meyer et al. (British Journal of Haematology, 2018, 180, 808-820). (Year: 2018).*
U.S. Appl. No. 15/563,830, entitled, "Methods for Selective Expansion of Gamma Delta T-Cell Populations and Compositions Thereof," filed Oct. 2, 2017, of Adicet Bio, Inc.
Appay et al, "Memory CD8+ T cells vary in differentiation phenotype in different persistent virus infections," Nature Medicine, vol. 8, pp. 379-385 (2002).
Bornstein et al, "Development of a new fully human anti-CD20 monoclonal antibody for the treatment of B-cell malignancies," Investigational New Drugs., Vo. 28, Issue 5, pp. 561-574 (2010).
Boucherma et al., "HLA-A*01:03, HLA-A*24-02, HLA-B8:08-01, HLA-B*27:05, HLA-B*35:01, HLA-B*44:02, AND HLA-C*07:01 Monochain Transgenic/H-2 Class I Null Mice: Novel Versatile Preclinical Models of Human T Cell Responses," J. Immunol., vol. 191, pp. 583-593 (2013).
Carding and Egan, "γδ TCELLS: Functional Plasticity and Heterogeneity," Nat Rev Immunol vol. 2, pp. 336-345 (2002).

(Continued)

*Primary Examiner* — Zachary S Skelding
(74) *Attorney, Agent, or Firm* — Todd A. Lorenz

(57) ABSTRACT

The present invention relates to engineered γδ T-cell(s) and methods for using the same as a therapeutic with a potent and selective ability to target an antigen of choice. Engineered γδ T-cells of the disclosure are useful in the treatment of various cancers, infectious diseases, and immune disorders. Also disclosed are methods for expanding engineered and non-engineered γδ T-cell(s) populations to therapeutically useful quantities. An engineered γδ T-cell of the disclosure can be a universal donor, and can be administered to a subject with any MHC haplotype.

12 Claims, 13 Drawing Sheets

Specification includes a Sequence Listing.

(56) References Cited

OTHER PUBLICATIONS

Cheever et al., "The Prioritization of Cancer Antigens: A National Cancer Institute Pilot Project for the Acceleration of Translational Research," Clin. Cancer Res., vol. 15(17), pp. 5323-5337 (2009).
Chen et al., "Selection and analysis of an optimized anti-VEGF antibody: crystal structure of an affinity-matured Fab in complex with antigen," J. Mol. Biol. vol. 293, pp. 865-881 (1999).
Chothia and Lesk, "Canonical Structures for the Hypervariable Regions of Immunoglobulins," J. Mol. Biol., vol. 196, pp. 901-917 (1987).
Chothia et al., "Conformations of immunoglobulin hypervariable regions," Nature, vol. 342, pp. 878-883 (1989).
Dao et al. "Targeting the intracellular WT1 oncogene product with a therapeutic human antibody" Science translational medicine, vol. 5(176): 176ra33, pp. 1-22 (2013).
Daubenberger et al., "Functional and Structural Similarity of Vγ9Vδ2 T Cells in Humans and Aotus Monkeys, a Primate Infection Model for Plasmodium falciparum Malaria," J Immunol, vol. 167, pp. 6421-6430 (2001).
Davis and Merwe, "The structure and ligand interactions of CD2: implications for T-cell function," Immunol. Today, vol. 17, Issue 4, pp. 177-187 (1996).
Deniger et al., "Bispecific T-cells Expressing Polyclonal Repertoire of Endogenous γδ T-cell Receptors and Introduced CD19-specific Chimeric Antigen Receptor," Molecular Therapy, vol. 21, No. 3, pp. 638-647 (2013).
Dohan & Reiter, "T-cell-receptor-like antibodies—generation, function and applications," Expert Rev Mol Med., vol. 14(e6), pp. 1-17 (2012).
Dokouhaki et al, Adoptive immunotherapy of cancer using ex vivo expanded human γδ T cells: A new approach, Cancer Letters, vol. 297, pp. 126-136 (2010).
Gonzalez et al., "Humanized mice: novel model for studying mechanisms of human immune-based therapies," Immunol. Res. vol. 57, pp. 326-334 (2013).
Gra et al., "Analysis of T-Cell Receptor-γ Gene Rearrangements Using Oligonucleotide Microchip: A Novel Approach for the Determination of T-Cell Clonality," Journal of Molecular Diagnostics, vol. 9, No. 2 pp. 249-257 (2007).
Groh et al., "Broad tumor-associated expression and recognition by tumor-derived gamma delta T cells of MICA and MICB," PNAS, vol. 96, pp. 6879-6884 (1999).
Hamers-Casterman et al., "Naturally occurring antibodies devoid of light chains," Nature, vol. 63, pp. 446-448 (1993).
Hayday A.C., "γδ Cells: A Right Time and Right Place for a Conserved Third Way of Protection," Annu Rev Immunol. vol. 18, pp. 975-1026 (2000).
Hayday and Pennington, "Key factors in the organized chaos of early T cell development," Nature Immunology. vol. 8, No. pp. 137-144 (2007).
Jakobovits et al., "Production of fully human antibodies by transgenic mice," Curr. Opin. Biotechnol., vol. 6, Issue 5, pp. 561-566 (1995).
Janssens et al., "Generation of heavy-chain-only antibodies in mice," PNAS, vol. 103, No. 41, pp. 15130-15135 (2006).
Jin et al., "Oligoclonal expansion of TCR Vδ T cells may be a potential immune biomarker for clinical outcome of acute myeloid leukemia," Journal of Hematology & Oncology vol. 9:126, pp. 1-7 (2016).
Kabelitz and He, "The Multifunctionality of Human Vγ9Vδ2 γδ T Cells: Clonal Plasticity or Distinct Subsets? : Plasticity of Human γδ T Cells," Scandinavian Journal of Immunology, vol. 76, pp. 213-222 (2012).
Kang et al., "Adoptive immunotherapy of lung cancer with immobilized anti-TCRγδ antibody-expanded human γδ T-cells in peripheral blood," Cancer Biology & Therapy, vol. 8, Issue 16, pp. 1540-1549 (2009).
Kim and Hong, "Humanization by CDR Grafting and Specificity-Determining Residue Grafting," Methods in Molecular Biology, vol. 907, pp. 237-245 (2012).
Klebanoff et al, "CD8+ T-cell memory in tumor immunology and immunotherapy," Immunol Rev., vol. 211, pp. 214-224 (2006).
Kress et al., Distinct gene expression in human Vγ1 and Vδ2 γδ T cells following non-TCR agonist stimulation, Molecular Immunology, vol. 43, pp. 2002-2011 (2006).
Kondo et al., "Zoledronate facilitates large-scale ex vivo expansion of functional γδ T cells from cancer patients for use in adoptive immunotherapy," Cytotherapy, vol. 10, No. 8, pp. 842-856 (2008).
Lamb and Lopez, "γδ T cells: A New Frontier for Immunotherapy?," Biology of Blood and Marrow Transplantation, vol. 11, pp. 161-168 (2005).
Lang et al., "Pilot trial of interleukin-2 and zoledronic acid to augment γδ T cells as treatment for patients with refractory renal cell carcinoma," Cancer Immunol Immunother, vol. 60, pp. 1447-1460 (2011).
Lefranc et al., "IMGT unique numbering for immunoglobulin and T cell receptor variable domains and Ig superfamily V-like domains," Developmental & Comparative Immunology, vol. 27, pp. 55-77 (2003).
Li et al, "Transgenic mice with a diverse human T cell antigen receptor repertoire," Nature Med.vol. 16, pp. 1029-1035 (2010).
Lopez et al., "CD2-mediated IL0120dependent signals render human-T cells resistant to mitogen-induced apoptosis, permitting the large-scale ex vivo expansion of functionally distinct lymphocytes: implications for the development of adoptive immunotherapy strategies," Blood, vol. 96, pp. 3827-3837 (2000).
Malmborg et al., "BIAcore as a tool in antibody engineering," J. Immunol. Methods, vol. 183, pp. 7-13 (1995).
Mangan et al., "Cutting Edge: CD1d Restriction and Th1/Th2/Th17 Cytokine Secretion by Human V 3 T Cells," J. of Immunol., vol. 191, pp. 30-34 (2013).
Michie et al., "Lifespan of human lymphocyte subsets defined by CD45 isoforms," Nature, vol. 360, pp. 364-365 (1992).
Moonka and Loh, "A consensus primer to amplify both α and β chains of the human T cell receptor," Journal of Immunological Methods, vol. 169, pp. 41-51 (1994).
Nagamine et al., Induction of γδ T Cells Using Zoledronate Plus Interleukin-2 in Patients with Metastatic Cancer, Hiroshima J. Med. Sci, vol. 58, No. 2, pp. 37-44 (2009).
Nakajima et al., "A phase I study of adoptive immunotherapy for recurrent non-small-cell lung cancer patients with autologous γδ T cells," European Journal of Cardio-thoracic Surgery, vol. 37, pp. 1191-1197 (2010).
Nicol et al., "Clinical evaluation of autologous gamma delta T cell-based immunotherapy for metastatic solid tumours," British Journal of Cancer, vol. 105, pp. 778-786 (2011).
Nussbaumer et al., "Essential Requirements of Zoledronate-Induced Cytokine and γδ T Cell Proliferative Responses,", J. of Immunol., vol. 191, No. 3, pp. 1346-1355 (2013).
Rei et al., "The Emerging Protumor Role of γδ T Lymphocytes: Implications for Cancer Immunotherapy," Cancer Research, vol. 75(5), pp. 798-802 (2015).
Sallusto et al., "Two subsets of memory T lymphocytes with distinct homing potentials and effector functions," Nature, vol. 401, p. 708-712 (1999).
Saitoh et al., "Anti-tumor cytotoxicity of γδ T cells expanded from peripheral blood cells of patients with myeloma and lymphoma," Med Oncol., vol. 25, pp. 137-147 (2008).
Scheinberg et al., "Reaching Un-Drugable Intracellular Targets with the Long Arm of Antibodies," Oncotarget, vol. 4(5), pp. 647-648 (2013).
Scheper et al., "Hunting for clinical translation with innate-like immune cells and their receptors", Leukemia, vol. 28, No. 6, pp. 1181-1190 (2014).
Sheriff and Constantine, "Redefining the minimal antigen-binding fragment," Nature Struct. Biol., vol. 3, No. 9, pp. 733-736 (1996).
Siegers et al., "Human V delta 1 gamma delta T cells expanded from peripheral blood exhibit specific cytotoxicity against B-cell chronic lymphocytic leukemia-derived cells", Cytotherapy, vol. 13, No. 6, pp. 753-764 (2011).

(56) References Cited

OTHER PUBLICATIONS

Weidanz et al., "TCR-Like Biomolecules Target Peptide/MHC Class I Complexes on the Surface of Infected and Cancerous Cells," Int. Rev. Immunol., vol. 30, pp. 328-340 (2011).
Wild et al., "Dependence of T Cell Antigen Recognition on the Dimensions of an Accessory Receptor-Ligand Complex," J. Exp. Med, vol. 190, No. 1, pp. 31-41 (1999).
Wilhelm et al., "γδ T cells for immune therapy of patients with lymphoid malignancies," Blood, vol. 102, No. 1, pp. 200-206 (2003).
Wilhelm et al., "Successful adoptive transfer and in vivo expansion of haploidentical γδ T Cells," J Transl Med., vol. 12, pp. 1-6 (2014).
Wu et al., "Ex vivo expanded human circulating Vδ1 γδ T cells exhibit favorable therapeutic potential for colon cancer," Oncoimmunology, vol. 4:3, pp. e992749-13 (2015).
Xu et al., "Diversity in the CDR3 region of V(H) is sufficient for most antibody specificities," Immunity, vol. 13, pp. 37-45 (2000).
Yoon et al., "The Cell Cycle Time of CD8+ T Cells Responding In Vivo Is Controlled by the Type of Antigenic Stimulus," PLOS One, vol. 5(11), pp. 1-12 (2010).
Yu et al., "Expansion and Immunological Study of Human Tumor Infiltrating Gamma-Delta T Lymphocytes in vitro," Int Arch Allergy Immunol, vol. 119, pp. 31-37 (1999).
Zapata et al., "Engineering linear F(ab')2 fragments for efficient production in *Escherichia coli* and enhanced antiproliferative activity," Protein Eng. vol. 8, No. 10, pp. 1057-1062 (1995).
Zhou et al., "Anti-γδ TCR antibody-expanded γδ T cells: a better choice for the adoptive immunotherapy of lymphoid malignancies," Cellular & Molecular Immunology, vol. 9, pp. 34-44 (2012).
Fisher et al., "Neuroblastoma Killing Properties of Vδ2 and Vδ2-Negative γδT Cells Following Expansion by Artificial Antigen-Presenting Cells," Clinical Cancer Research, vol. 20, No. 22, pp. 5720-5732 (2014).
Hiasa et al., "Dual specificity of αβ-γδ TCR T cells: transformation of Vγ9Vδ2 T cells with MAGE-A4143-151 specific αβ type TCR genes," Annual Meeting of the Japanese Cancer Association, vol. 66, p. 423 (2007).
Hua et al., "Potentinal regulatory role of in vitro-expanded Vδ1 T cells from human peripheral blood," Immunol Res. vol. 56, pp. 172-180 (2013).
Luoma et al., "γδ T cell surveillance via CD1 molecules," Trens in Immunolgoy, vol. 35, No. 12, pp. 613-621 (2014).
Petros et al., "Improved analysis of TCR γδ variable region expression in humans," Journal of Immunological Methods, vol. 434, pp. 66-72 (2016).
Qi et al., "Immobilized MICA Could Expand Human Vδ1 γδT Cells In Vitro that Displayed Major Histocompatibility Complex Class I Chain-Related A-Dependent Cytotoxicity to Human Epithelial Carcinomas." Scandinavian Journal of Immunology, vol. 58, No. 2, pp. 211-220 (2003).
Sagar et al., "In vivo immunogenicity of Tax(11-19) epitope in HLA-A2/DTR transgenic mice: Implication for dendritic cell-based anti-HTLV-1 vaccine," Vaccine, vol. 32, , pp. 3274-3284 (2014).
Shang et al., "Rational optimization of tumor epitopes using in silico analysis-assisted substitution of TCR contact residues," European Journal of Immunology, vol. 39, pp. 2248-2258 (2009).
BioCompare, "Monoclonal Antibody Anti-Human TCR PAN [gamma]/[delta] PN IM1349—Purified—Freeze-dried—0.1 mg—Clone IMMU510 For Research Use Only. Not for use in diagnostic procedures", Beckman Coulter: Jan. 1, 2006, p. 1, left-hand column, paragraph 1, Retrieved from the Internet [on Apr. 8, 2019] at URL:https://www.bc-cytometry.com/PDF/DataSheet/IM1349.pdf.
Ciccone, "A monoclonal antibody specific for a common determinant of the human T cell receptor gamma/delta directly activates CD3+WT31-lymphocytes to express their functional program(s)", The Journal of Experimental Medicine, vol. 168, pp. 1-11 (1988).
Ehl et al., "A variant of SCID with specific immune responses and predominance of gamma delta T cells", J. of Clinical Investigation, vol. 115, No. 11, pp. 3140-3148 (2005).
Romagne F et al, "Structural analysis of gammadelta TCR using a novel set of TCR gamma and delta chain-specific monoclonal antibodies generated against soluble gammadelta TCR Evidence for a specific conformation adopted by the Jdelta2 region and for a Vdelta1 polymorphism", Journal of Immunological Methods, vol. 189, No. 1, pp. 25-36 (1996).
Siegers et al., "Extensive expansioin of primary human gamma delta T cells generates cytotoxic effector memory cells that can be labeled with Feraheme for cellular MRI", Cancer Immunol. Immunother, vol. 62(3), pp. 571-583 (2012).
Taupin et al., "An enlarged subpopulation of T lymphocytes bearing two distinct [gamma][delta] TCR in an HIV-positive patient", International Immunology, vol. 11, No. 4, pp. 545-552 (1999).
Vantourout et al., "Specific requirements for Vγ9Vδ2 T cell stimulation by a natural adenylated photphoantigen", J. Immunol., vol. 183(6), pp. 3848-3857 (2009).

\* cited by examiner

Panel A

TCR γδ   Engineered Tumor
         Recognition Moiety

Panel B

TCR γδ   Engineered Tumor
         Recognition Moiety

SEQUENCE LISTING

```
<160> NUMBER OF SEQ ID NOS: 16

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 1
atgctgttct ccagcctgct gtgtgtattt                                    30

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atgcagagga tctcctccct catccatct                                     29

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atgattctta ctgtgggctt tagcttttg                                     30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cttggggtag aattccttca ccagacaagc                                    30

<210> SEQ ID NO 5
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Pro Ala Tyr Gln Gln Gly Gln Asn Gln Leu Tyr Asn Glu Leu Asn
1               5                   10                  15

Leu Gly Arg Arg Glu Glu Tyr Asp Val Leu Asp Lys Arg
            20                  25

<210> SEQ ID NO 6
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Pro Gln Arg Arg Lys Asn Pro Gln Glu Gly Leu Tyr Asn Glu Leu Gln
1               5                   10                  15

Lys Asp Lys Met Ala Glu Ala Tyr Ser Glu Ile Gly Met
            20                  25

<210> SEQ ID NO 7
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Arg Arg Arg Gly Lys Gly His Asp Gly Leu Tyr Gln Gly Leu Ser
1               5                   10                  15

Thr Ala Thr Lys Asp Thr Tyr Asp Ala Leu His Met Gln
            20                  25

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agagtgaagt tcagcaggag cgca                                          24

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctcgagtggc tgttagccag a                                             21

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggtgcttcta gctttcctgt ctcctgc                                       27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atgctgttgg ctctagctct gcttcta                                       27

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 12
atgctgtcac tgctccacac atcaacg                                              27

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggaagaaaaa tagtgggctt gggggaa                                              27

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atgacaacac ccagaaattc agtaaatgg                                            29

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tcaaggagag ctgtcatttt ctattggtg                                            29

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Leu Leu Met Trp Ile Thr Gln Cys
1               5
```

ENGINEERED γδ T-CELLS

CROSS-REFERENCE

This application claims priority from U.S. Provisional Application No. 62/080,500, filed on Nov. 17, 2014, the entire content of which is incorporated herein by reference in its entirety.

BACKGROUND

Antigen recognition by T lymphocytes may be achieved by highly diverse heterodimeric receptors, the T-cell receptors (TCRs). Approximately 95% of human T-cells in blood and lymphoid organs express a heterodimeric αβ TCR receptor (αβ T-cell lineage). Approximately 5% of human T-cells in the blood and lymphoid organs express heterodimeric γδ TCR receptor (γδ T-cell lineage). These T-cell subsets may be referred to as 'αβ' and 'γδ' T-cells, respectively. αβ and γδ T-cells are different in function. αβ T-cells drive MHC-restricted adoptive immunity and γδ T-cells bridge innate and non-MHC restricted adoptive immunity. Activation of αβ T-cells then occurs when an antigen presenting cell (APC) presents an antigen in the context of class I/II MHC. Dendritic cells are the strongest known activators of nave T-cells. Two signals are necessary for full αβ T-cell activation: a) a signal generated by the interaction of MHC-peptide with a TCR-CD3 complex; and b) a signal generated by interaction of CD28 on the T-cells and members of the B7 family on the APC (co-stimulatory signal). In contrast to αβ T-cells, γδ T-cells can recognize an antigen directly, and do not require the interaction of MHC-peptide with a TCR-CD3 complex. Hence, it is said that γδ T-cells are not MHC restricted. In endogenous T-cells, lack of co-stimulatory signal results in clonal anergy.

The ability of endogenous γδ T-cells to recognize an antigen directly renders γδ T-cells an attractive therapeutic tool. However, difficulties in manipulating and directing endogenous γδ T-cells limit the therapeutic usefulness of patient derived γδ T-cells in the clinic.

SEQUENCE LISTING

The instant application contains a Sequence Listing which has been submitted in ASCII format via EFS-Web and is hereby incorporated by reference in its entirety. Said ASCII copy, created on Mar. 3, 2016 is named 47165-701.201-SL.txt and is 4,366 Kilobytes in size.

SUMMARY

In some embodiments, the disclosure provides an engineered γδ T-cell, wherein the engineered γδ T-cell is engineered to express one, two, or more different tumor recognition moieties, wherein each tumor recognition moiety recognizes a tumor antigen. A tumor recognition moiety can be designed to recognize different epitopes of the same tumor antigen, antigens of distinct tumors, a tumor antigen and an activating or inactivating co-stimulatory/immune modulation receptors, an antigen in complex with an MHC molecule, or a homing receptor. In some cases, the disclosure provides a method for treating a cancer with engineered γδ T-cell. An engineered γδ T-cell can be designed to be allogeneic to a subject and an engineered γδ T-cell can be a tumor-specific allogeneic γδ T-cell. In some cases, the engineered γδ T-cell lacks a human HLA locus. The HLA locus can be chosen from the group consisting of HLA-A, HLA-B, HLA-C, HLA-DP, HLA-DM, HLA-DOA, HLA-DOB, HLA-DQ, and HLA-DR and as engineered γδ T-cell can be designed engineered to lack gene expression from two or more HLA loci. In some cases, at least one engineered tumor recognition moiety is an engineered T-cell receptor. A T-cell receptor can be a human T-cell receptor, a mouse T-cell receptor, a rat T-cell receptor, or a chimeric T-cell receptor. An engineered T-cell receptor can be an engineered αβ TCR and two different engineered αβ TCRs can be designed to recognize different epitopes of the same antigen. In other cases, the engineered T-cell receptor is a engineered γδ TCR. In some embodiments, an engineered γδ T-cell is designed to infiltrate a solid tumor. An engineered γδ T-cell can be designed to recognize a tumor antigen that is expressed intracellularly or extracellularly within a tumor cell. In the case of an extracellularly expressed tumor antigen, an engineered γδ T-cell can be configured to recognize an antigen that is a peptide in complex with an MHC molecule. In some cases, the tumor antigen is a lymphoma antigen, a leukemia antigen, a multiple myeloma antigen, breast cancer antigen, a prostate cancer antigen, a bladder cancer antigen, a colon and rectal cancer antigen, a brain cancer antigen, a gastric cancer antigen, a head and neck cancer antigen, a kidney cancer antigen, a lung cancer antigen, a pancreatic cancer antigen, a sarcoma antigen, a mesothelioma antigen, an ovarian cancer antigen or a melanoma antigen. In some cases, the engineered γδ T-cell is derived from a Vδ1$^+$ T-cell, a Vδ2$^+$ T-cell or a Vδ3$^+$ T-cell, or a mixture of Vδ1$^+$, Vδ2$^+$, or Vδ3$^+$ T-cells. The engineered γδ T-cell can be derived from CD3$^+$ T-cell or a CD3$^-$ T-cell. The engineered γδ T-cell can be designed to recognize different epitopes of the same antigen.

In some cases, the two or more different tumor recognition moieties are encoded by different polynucleotide sequences, and each different polynucleotide sequence is engineered to recognize a different epitope of the same antigen. In some cases, at least one tumor recognition moiety is cloned from a tumor cell. In other cases, at least one tumor recognition moiety is synthetically engineered. In some cases, at least one tumor recognition moiety is an antibody fragment, or an antigen binding fragment thereof, that recognizes a tumor antigen. A tumor recognition moiety can be an engineered immunoglobulin light chain, an engineered immunoglobulin heavy chain, or any fragment thereof. In some cases, the engineered γδ T-cell also expresses a migration and a homing receptor. A homing molecule can adhere an engineered γδ T-cell to a solid tumor. In some cases the engineered γδ T-cell is further engineered to lack at least one immune checkpoint gene and the immune checkpoint gene can be a CTLA-4 gene, a PD-1 gene, a LAG3 gene, a CEACAM-1 gene, or another gene. In some cases, the tumor antigen is selected from CD19, CD30, CD22, CD37, CD38, CD56, CD33, CD30, CD138, CD123, CD79b, CD70, CD75, CA6, GD2, alphafetoprotein (AFP), carcinoembryonic antigen (CEA), CEACAM5, CA-125, MUC-16, 5T4, NaPi2b, ROR1, ROR2, 5T4, PLIF, Her2/Neu, EGFRvIII, GPMNB, LIV-1, glycolipidF77, fibroblast activating protein, PSMA, STEAP-1, STEAP-2, mesothelin, c-met, CSPG4, Nectin-4, VEGFR2, PSCA, folate binding protein/receptor, SLC44A4, Cripto, CTAG1B, AXL, IL-13R, IL-3R, SLTRK6, gp100, MART1, Tyrosinase, SSX2, SSX4, NYESO-1, epithelial tumor antigen (ETA), MAGEA family genes (such as MAGE3A. MAGE4A), KKLC1, mutated ras, βraf, p53, MHC class I chain-related molecule A (MICA), MHC class I chain-related molecule B (MICB), HPV, or CMV. In other cases, at least one tumor recognition moiety is a chimeric antigen receptor (CAR) designed to recognize an antigen, a portion, or a fragment of any antigen described herein.

In other embodiments, an engineered γδ T-cell is engineered to express an antigen recognition moiety, wherein the antigen recognition moiety recognizes an antigen associated with an autoimmune disease. Such cells may be engineered to express one, two, or more antigen recognition moieties, wherein each antigen recognition moiety recognizes a different epitope of the same autoimmune antigen. In some cases, the tumor recognition moiety recognizes distinct antigens, an antigen and an activating or inactivating co-stimulatory/immune modulation receptors, an antigen in complex with an MHC molecule, or a homing receptor associated with an autoimmune disease.

In alternative embodiments, an engineered γδ T-cell is engineered to express an antigen recognition moiety, wherein the antigen recognition moiety recognizes a pathogenic antigen. Such cells may be engineered to express two or more antigen recognition moieties, wherein each antigen recognition moiety recognizes a different epitope of the same pathogenic antigen. In some cases, the tumor recognition moiety recognizes distinct antigens, an antigen and an activating or inactivating co-stimulatory/immune modulation receptors, an antigen in complex with an MHC molecule, or a homing receptor associated with a pathogenic antigen.

A pathogenic antigen can be a bacterial molecule or a viral molecule, such as a bacterial protein or a viral protein.

In other cases, the disclosure provides a γδ T-cell population, wherein the expansion of the γδ T-cell population is activated with an agent that stimulates an expansion of the γδ T-cell population at a mean rate of about 1 cell division in less than 24 hours. In some cases, the expanded γδ T-cell population comprises a percentage of δ1 T-cells, δ2 T-cells, or δ3 T-cells and the percentage of the any of one of the aforementioned expanded γδ T-cells can be greater than 5%. In some instances, the percentage of δ1, δ2, or δ3 T-cells in the γδ T-cell population expands in vitro or in vivo at a mean rate of about 1 cell division in less than 24 hours. In some cases, the γδ T-cell population further comprises an amount of engineered γδ T-cells, wherein the engineered γδ T-cells are engineered to express an antigen recognition moiety. The engineered γδ T-cells can be designed to also lack a human HLA locus. The agent that stimulates an expansion of the γδ T-cell population can be an antibody, and the antibody can be selected from the group consisting of 5A6.E9, B1, TS8.2, 15D, B6, B3, TS-1, γ3.20, 7A5, IMMU510, R9.12, and 11F2 antibodies. In some cases, the antibody is immobilized on a surface.

In some cases, the disclosure relates to an activating epitope of a γδ T-cell. In some cases, the activating epitope stimulates expansion of a γδ T-cell population at a mean rate of 1 cell division in less than 24 hours, or another suitable time period that support a rapid expansion of a population of γδ T-cells. In some cases the activating epitope is an amino acid sequence of a δ TCR, such as δ1, δ2, or δ3 TCR. In some instances, the activating epitope is the epitope bound by any one of the antibodies selected from the group consisting of 5A6.E9, B1, TS8.2, 15D, B6, B3, TS-1, γ3.20, 7A5, IMMU510. R9.12, and 11F2 antibodies. The activating epitope can comprise an amino sequence from a Vδ1 gene segment and a Jδ1, Jδ2, Jδ3, or Jδ4 gene segments. In some cases the activating epitope is a conformational epitope and in other cases the activating epitope is a linear epitope.

In some cases the disclosure provides a method of determining an epitope of a γδ T-cell receptor, the method comprising (a) preparing a library of epitopes from the γδ T-cell receptor; (b) contacting the library of epitopes with an antibody; and (c) identifying the amino acid sequence of at least one epitope in the library of epitopes that is bound by the antibody. The antibody can be selected from the group consisting of 5A6.E9, B1, TS8.2, 15D, B6, B3, TS-1, γ3.20, 7A5, IMMU510, R9.12, 11F2 antibodies. In some cases, the antibody is attached to a solid support. The epitope of the T-cell receptor can correspond to a continuous or to a discontinuous sequence of amino acids in the T-cell receptor. The library of epitopes can comprise fragments ranging from about 10 amino acids to about 30 amino acids in length, from about 10 amino acids to about 20 amino acids in length, from about 5 amino acids to about 12 amino acids in length. In some cases, the antibody is labeled. The label can be a radioactive molecule, a luminescent molecule, a fluorescent molecule, an enzyme, or biotin. In some cases, the library of epitopes comprises peptides translated from synthetically designed cDNAs, wherein the synthetically designed cDNAs comprise segments of a plurality of synthetically designed γ TCRs and a plurality of synthetically designed δ TCRs. In other cases the library of epitopes comprises peptides amplified from total RNA extracted from human δγ T-cells, originated from human PBMCS, or lymphocytes isolated from human malignant or normal epithelial tissue. The library of synthetically designed cDNAs can comprise a plurality of Vδ1, Vδ2, and Vδ3 gene segments differing in their Jδ region and the library can comprise a plurality of Vγ2, Vγ3, Vγ4, Vγ5, Vγ8, Vγ9, Vγ10, δ1, δ2, and δ3 gene segments.

In some embodiments, the disclosure provides a method of treating a subject in need thereof, comprising administrating to said subject an engineered γδ T cell described herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

DETAILED DESCRIPTION

Figure 1:
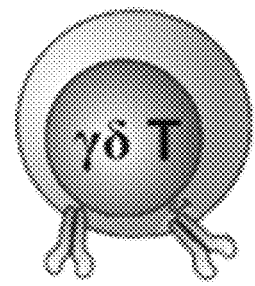
FIG. 1 schematically illustrates engineered γδ T-cells. Panel A illustrates an engineered γδ T-cell expressing one tumor recognition moiety. Panel B illustrates an engineered γδ T-cell expressing two tumor recognition moieties.
Figure 1:
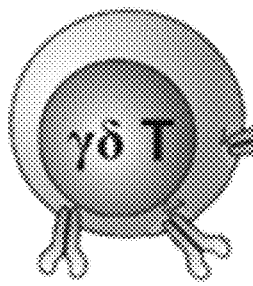

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Overview

In humans, γδ T-cell(s) are a subset of T-cells that provide a link between the innate and adaptive immune responses. These cells undergo V-(D)-J segment rearrangement to generate antigen-specific γδ T-cell receptors (γδ TCRs), and γδ T-cell(s) and can be directly activated via the recognition of an antigen by either the γδ TCR or other, non-TCR proteins, acting independently or together to activate γδ T-cell effector functions. γδ T-cells represent a small fraction of the overall T-cell population in mammals, approximately 1-5% of the T-cells in peripheral blood and lymphoid organs, and they appear to reside primarily in epithelial cell-rich compartments like skin, liver, digestive, respiratory, and reproductive tracks. Unlike αβ TCRs, which recognize antigens bound to major histocompatibility complex molecules (MHC), γδ TCRs can directly recognize bacterial antigens, viral antigens, stress antigens expressed by diseased cells, and tumor antigens in the form of intact proteins or non-peptide compounds.

The ability of γδ T-cells to recognize a broad spectrum of antigens can be enhanced by genetic engineering of the γδ T-cells. γδ T-cell(s) can be engineered to provide an universal allogeneic therapy that recognizes an antigen of choice in vivo. Described herein, is a γδ T-cell(s) that has been engineered to express an expression cassette comprising at least one tumor recognition moiety, such as an αβ TCR or γδ TCR, coupled to a transmembrane domain and/or an intracellular T-cell activation domain. The activation domains can be derived from the αβ TCR or γδ TCR machinery of a T-cell. For instance, the activation domain can be derived from a CD28, CD2, CTLA-4, ICOS, JAMAL, PD-1, 41-BB, CD27, CD30, OX40, NKG2D, HVEM, or CD46 molecules. A γδ T-cell can be engineered to express two or more distinct TCR's, distinct antibodies, or antigen binding fragments that recognize different epitopes of the same antigen. When administered to a subject, engagement of an engineered αβ TCR, γδ TCR, antibody, or chimeric antigen receptor CAR with an antigen effectively provides a γδ T-cell with significant cytotoxicity in vivo. A TCR can be derived from a human T-cell, a mouse T-cell, a rat T-cell, a humanized mice, humanized rats, an immunized mammal, or from a phage or yeast library. An antibody, a CAR, or any antigen binding fragment can be derived from a human B-cell, a mouse B-cell, a rat B-cell, a camel B-cell, a llama B-cell, an immunized mammal, or from a phage or yeast library. A tumor recognition moiety expressed by an engineered γδ T-cell can recognize an antigen that is expressed intracellular or extracellularly by a diseased cell. For instance, a cell can be infected with a cancer causing virus, such as the human papilloma virus (HPV), and the diseased cell may express one or more HPV antigens intracellularly. The diseased cell may process the intracellularly expressed HPV antigens into smaller fragments, allowing the antigenic peptide to be coupled to an MHC Class I molecule and transported to the cell surface. A tumor recognition moiety of an engineered γδ T-cell can be designed to recognize various antigen fragments, or epitopes that are intracellularly expressed by a diseased cell and presented on the cell surface in complex with an MHC Class I or class II molecule. Alternatively, a tumor recognition moiety of an engineered γδ T-cell can be designed to recognize exogenous antigens expressed on the tumor cell surface or derived peptides displayed on the cell surface in complex with MHC Class molecules.

Provided herein is an engineered γδ T-cell(s) and methods for using the same as a therapeutic product with a potent and selective ability to target an antigen of choice on a diseased cell. The polynucleotide or protein sequence of an αβ or γδ TCR can be cloned with standard techniques from one or a plurality of αβ or γδ T-cell(s) that have engaged with a tumor antigen(s), a bacterial antigen(s), a viral antigen(s), or a stress antigen(s). Alternatively, the polynucleotide sequence of an αβ or γδ TCR can be designed in silico on a computer-program product. An expression cassette comprising the engineered γδ TCR can be synthesized with, for example, oligonucleotide synthesis techniques. High throughput screening techniques can be used to characterize the binding of the engineered TCR to the tumor antigen. Engineering of an expression cassette comprising αβ or γδ TCRs, the transmembrane domain and the activation domain increases the activity and cytotoxic properties of the γδ T-cell, thereby providing an engineered γδ T-cell with potent cytotoxicity.

The engineered γδ T-cells may be derived from non-engineered T-cells isolated from blood, cord blood, stem cells, tumors, or tumor infiltrating lymphocyte (TIL). The isolated T-cells may be derived from a mammal, for example a human. One or more cells in the isolated T-cell population may be engineered to express a polynucleotide (s) from an expression cassette that comprises, for example, a tumor recognition moiety coupled with a T-cell activation or inactivation domain. The tumor recognition moiety is designed to recognize a target tumor antigen, a tumor cell inactivation or a T-cell inactivation domain. The tumor recognition moiety is designed to recognize a target tumor antigen, an activating or inactivating co-stimulatory/immune modulation receptors, or a homing receptor. A tumor antigen can be, for example, a peptide derived from intracellular or extracellular protein expressed on the cell surface in a complex with major histocompatibility complex (MHC). In some cases, the tumor recognition moiety is an αβ TCR and the antigen is a peptide presented by a tumor cell in complex with MHC. An antigen can be a molecule derived from a cell in distress, such as a cancerous cell, or from pathogens such as viruses or intracellular bacteria, which replicate within cells, or from pathogens or their products that cells have internalized by endocytosis from the extracellular fluid. In some cases, an engineered γδ T-cell is designed to express two or more different tumor recognition moieties, and each tumor recognition moiety is designed to recognize a different epitope of the same antigen. Universal engineered γδ T-cell(s) can express tumor recognition moieties that can recognize an antigen with different MHC haplotypes. The tumor recognition moiety can comprise either TCR (αβ or γδ TCR) or antibodies recognizing peptide-MHC complexes. For example, for a given antigen, different tumor recognition moieties, either TCRs or antibodies, can recognize the same or different antigen-derived peptides complexed with different HLA haplotypes.

The engineered γδ T-cells, when administered to a subject, can weaken or kill a cell expressing the target antigen. The engineered γδ T-cell(s) may be introduced to a human in need of treatment of a disease. In a preferred embodiment, the cells are administered to a person having cancer and in such cases the cells are engineered to recognize a tumor antigen or other disease related antigen. FIG. 1 schematically illustrates a γδ T-cell. Panel A illustrates an engineered γδ T-cell expressing one tumor recognition moiety. Panel B illustrates an engineered γδ T-cell expressing two tumor recognition moieties.

The recognition moiety encoded by the expression cassette, such as a Chimeric Antigen Receptor (CAR), can be a whole antibody, an antibody fragment, a single-chain variable fragment (scFv), a single domain antibody, (sdAb), a Fab, F(ab)$_2$, an Fc, the light or heavy chains on an antibody, the variable or the constant region of an antibody, or any combination thereof that binds to a cell surface tumor antigen, a peptide derived from a tumor antigen expressed on the cell surface as a complex with MHC (peptide-MHC complex), or a bi-specific construct, comprising two different antibodies directed to two different antigens, different epitopes of the same antigen, or a tumor antigen and a co-stimulatory/activating molecule, immune modulatory molecule(s), or a homing receptor(s). The antibodies can be derived from, for example, human B-cells, mouse B-cells, a rat B-cell, or from hybridoma cell lines. A mouse hybridoma cell line can be derived from immunized wild type or humanized mice, a rat B-cell, a rat hybridoma cell isolated from immunized wild type or humanized rats, or from antibody libraries derived from human, mouse, rat, camel, or llama. An engineered tumor recognition moiety can be a CAR that recognizes cell surface antigen or peptide MHC-antigen complexes. An engineered tumor recognition moiety can be an engineered αβ TCR that recognizes a tumor-specific antigen complexed with MHC class I or II. The recognition moiety can also be an γδ TCR that recognizes a tumor specific antigen in non-MHC restricted manner. A tumor recognition moiety can be an engineered TCR or a CAR that recognizes a cell surface antigen, a peptide-MHC complex, a carbohydrate, or a lipid.

One, two, or more tumor recognition moieties can be designed to recognize the same or different antigens. One, two, or more tumor recognition moieties can be designed to recognize different epitopes of the same or different antigens. In some cases, the tumor recognition moiety is an αβ TCR receptor that is expressed by an expression cassette engineered into the genome of the γδ T-cell. In some instances, the engineered αβ TCR expressed by the engineered γδ T-cell is designed to recognize a peptide, or peptide mer (such as a 9-mer) derived from an antigen that is expressed intracellularly or extracellularly or on the cell surface by a tumor cell or another diseased cell. Intracellular antigens can be produced, for example, by viruses and bacteria replicating within an infected cell or by the subject's own proteins. The subject's cell can process the antigen into peptides and present the peptides in complex with MHC class I or II molecules. Engineered γδ T-cell(s) of the disclosure can be designed to recognize various different epitopes of various different intracellular antigens. Extracellular, or exogenous antigens, such as bacteria, parasites, viruses, or even cancerous cells, can be phagocytosed by antigen presenting cells, processed into smaller fragments, and presented in complex with MHC class II molecules. Engineered γδ T-cell(s) of the disclosure can be designed to recognize various different epitopes of various different extracellular antigens. In some cases, the tumor recognition moiety is a γδ TCR receptor that provides the cell with new antigen recognition. The expression cassette may include, for example, a CAR, expressing an antibody or a ligand, which is integrated into the genome of the γδ T-cell and expressed by the same. In some instances, the tumor recognition moiety may be a bi-specific construct, comprising, for example, an antibody, a TCR, an antigen binding fragment described herein, or any combination thereof. A γδ T-cell can be engineered from a tumor infiltrating lymphocyte (TILs) and/or a tumor recognition moiety that is encoded by the expression cassette can be isolated from TILs. A γδ T-cell that is engineered from a TIL can be a tumor-specific allogeneic cell that effectively migrates, homes, and interacts with the tumor microenvironment. An engineered γδ T-cell can be engineered from TILs isolated from specific tumors, such as breast cancer, prostate cancer, bladder cancer, colon and rectal cancer, brain cancer, gastric cancer, head and neck cancer, kidney cancer, lung cancer, pancreatic cancer, sarcoma, mesothelioma, an ovarian cancer antigen or melanoma. A tumor recognition moiety can be derived from a synthetic library or a tumor recognition moiety can be derived from B-cells, T-cells isolated from, for example, lymphoma, leukemia, multiple myeloma, breast cancer, prostate cancer, bladder cancer, colon and rectal cancer, brain cancer, gastric cancer, head and neck cancer, kidney cancer, lung cancer, pancreatic cancer, sarcoma, mesothelioma, an ovarian cancer antigen or melanoma. In some cases, a tumor recognition moiety is derived from a tumor infiltrating lymphocyte isolated from a cancer.

The engineered γδ T-cell may further comprise a T-cell co-stimulatory/activation domain. A T-cell activation domain can be derived from a αβ T-cell and/or a γδ T-cell. For instance, an engineered (43 TCR can be designed to be linked to either a γδ co-stimulation/activation domain or to an αβ co-stimulation/activation domain. Non-limiting examples of αβ co-stimulatory/activation domains include CD28, CD2, CTLA4, ICOS, PD-1, 4-1 BB (CD137), OX40, CD27, HVEM. Non-limiting examples of γδ co-stimulatory/activation domains include CD28, CD2, ICOS, JAMAL, CD27, CD30, OX40, NKG2D, CD46. A tumor recognition moiety can be linked to a T-cell activation domain or any other suitable activation domain. The T-cell activation domain may be a CD3ζ domain, a CD28 domain, or another suitable activation domain including CD2, ICOS, 4-1 BB (CD137), OX40 (CD134), CD27, CD30, CD46, CD70, CD80, CD86, DAP, CD122, CTLA4, CD152, PD-1, JAMAL, NKG2D, CD314, and/or FceRIg. Transmembrane domains can include, for instance, the related domains of CD28, CD4, CD3e, CD16, and immunoglobulins.

The invention disclosed herein preferably provides an engineered γδ T-cell that expresses an expression cassette encoding a recognition molecule. In some cases, a nucleic acid sequence corresponding to the expression cassette is cloned and stably introduced into the genome of the engineered γδ T-cell. The nucleic acid sequence comprising the expression cassette, which can include the tumor recognition moiety and relevant activation domains, may be synthetically engineered and stably introduced into the genome of the engineered γδ T-cell. Two or more different tumor recognition moieties may be expressed from the same, or from a different expression cassette.

A variety of techniques may be used to engineer such cells. For example, cloned or synthetically engineered DNA can be inserted, replaced, or removed to generate an engineered γδ T-cell by genome editing methods with engineered nucleases, such as: a) the CRISPR/Cas system; b) Transcription Activator-Like Effector Nucleases (TALENs); c) zinc finger nucleases (ZFNs); d) and engineered meganuclease homing endonucleases. A Sleeping Beauty transposon system can also be used to transfer a nucleic acid comprising the code for a tumor recognition moiety to generate an engineered γδ T-cell. Various other polynucleotide delivery methods known in the art may be suitable for the engineering of γδ T-cells such as transfection, electroporation, transduction, lipofection, nanoengineered substances, such as Ormosil, viral delivery methods, including adenoviruses, retroviruses, lentiviruses, adeno-associated viruses, or another suitable method.

In some cases, the recognition moiety is derived from a single or multiple species, for example, the polynucleotide sequence of the recognition moiety can be derived, for instance, from a human (*Homo sapiens*), a mouse (e.g. *Mus musculus*), a rat (e.g. *Rattus norvegicus* or *Rattus rattus*), a camel (e.g. *Camelus dromedarius* or *Camelus bactrianus*), or from a llama (*Lama vicugna*) or the polynucleotide sequence of the recognition moiety can be a chimeric combination of both. The tumor recognition moiety is preferably derived from a human, but in some cases it may be derived from a mouse or other species, preferably a mammal. In some cases, the tumor recognition moiety is a chimeric TCR receptor or a chimeric CAR. In some cases, the polynucleotide sequence of a tumor recognition moiety derived from a non-human species is engineered to increase its similarity to a polynucleotide sequence from a human species, thereby "humanizing" the tumor recognition moiety. In some cases, a species, such as mice and rat, is "humanized" to provide, for example, humanized antibodies and TCRs.

The tumor recognition moiety is preferably constitutively expressed from the expression cassette in the engineered γδ T-cell. In some cases, the tumor recognition moiety is under the expression of an inducible expression system, such as the tetracycline-regulated T-REx™ mammalian expression system, a suitable Tet-on/Tet-off expression system, or another suitable system. In one specific case, the engineered γδ T-cell is derived from a human Vδ1+ T-cell, a human Vδ2+ T-cell, a human Vδ3+ T-cell, a human CD3+ T-cell, or a human CD3− T-cell.

The present disclosure provides methods and engineered γδ T-cell(s) that express a tumor recognition moiety from an expression cassette that can detect and targeted specific antigens in a subject in vivo. A subject can be a subject in need of treatment with a therapeutic agent that can recognize and kill or weaken a cell(s) expressing a specific antigen in an effective and selective manner. In preferred cases, the antigen is associated with a cancer. An antigen can be a lineage-specific tumor antigen. In one embodiment, the antigen is a tumor antigen such as CD19, CD30, CD22, CD37, CD38, CD56, CD33, CD30, CD138, CD123, CD79b, CD70, CD75, CA6, GD2, alphafetoprotein (AFP), carcinoembryonic antigen (CEA), CEACAM5, CA-125, MUC-16, 5T4, NaPi2b, ROR1, ROR2, 5T4, PLIF, Her2/Neu, EGFRvIII, GPMNB, LIV-1, glycolipidF77, fibroblast activating protein, PSMA, STEAP-1, STEAP-2, mesothelin, c-met, CSPG4, Nectin-4, VEGFR2, PSCA, folate binding protein/receptor, SLC44A4, Cripto, CTAG1B, AXL, IL-13R, IL-3R, SLTRK6, gp100, MART1, Tyrosinase, SSX2, SSX4, NYESO-1, epithelial tumor antigen (ETA), MAGEA family genes (such as MAGE3A. MAGE4A), KKLC1, mutated ras, βraf, p53, MHC class I chain-related molecule A (MICA), MHC class I chain-related molecule B (MICB), HPV, or CMV.

An engineered γδ T-cell of the disclosure can be autologous or allogeneic with respect to the MHC loci of a subject. For instance, autologous and allogeneic bone marrow transplantation (BMT) is used as a therapy for some conditions, particularly hematological malignancies. However, acute graft-versus-host disease (GVHD) and host-versus-graft disease (HVGD) remains the most important complication of BMT for allogeneic BMT.

Donor T-cells and host antigen-presenting cells (APCs) are critical for the induction of GVHD. Because γδ T-cells do not recognize MHC molecules from the host, antigen recognition by an engineered γδ T-cell of the invention may not trigger GVHD. An engineered γδ T-cell of the disclosure can be designed to be administered to a non-autologous subject without triggering graft-versus-host-disease. In addition, an engineered γδ T-cell can be designed to lack gene expression from one or more the MHC loci. Alternatively, a γδ T-cell can be engineered to lack one or more MHC locus (loci). Deletion of the MHC loci, or disruption of gene expression, in an engineered γδ T-cell can be achieved by gene editing technologies such as zinc finger nucleases (ZFNs), transcription activator-like effector nucleases (TALENs), CRISPR, and engineered meganucleases or by β2m deletion. In some cases, an engineered γδ T-cell of the disclosure is engineered to lack or disrupt gene expression of multiple MHC loci. In other cases, an engineered γδ T-cell is engineered to lack or disrupt gene expression in at least one MHC class I locus, at least one MHC class II locus, or both. Deletion of one or more MHC loci may provide an engineered γδ T-cell that is a universal donor for any subject with any MHC haplotype without triggering host versus graft disease, thereby providing an engineered γδ T-cell that can thrive, persist, expand, and function within the host without being targeted by the host's immune system.

The teachings and compositions described herein may be used in a whole variety of applications. In preferred embodiments, the tumor antigen is a breast cancer antigen, a prostate cancer antigen, a bladder cancer antigen, a colon and rectal cancer antigen, a brain cancer antigen, a gastric cancer antigen, a head and neck cancer antigen, a kidney cancer antigen, a lung cancer antigen, a pancreatic cancer antigen, a sarcoma antigen, a mesothelioma antigen, an ovarian cancer antigen, or a melanoma antigen. In such cases, the tumor recognition moiety may be an engineered αβ TCR or an antibody that is designed to recognize an epitope derived from an intracellular or an extracellular tumor antigen, presented on the tumor cell surface in a complex with class I or class II MHC. An engineered αβ TCR can recognize an intracellular tumor antigen that is presented by the tumor or by an APC, for instance, in the context of an HLA-A, HLA-B, or HLA-C complex, or in the context of HLA-DP, HLA-DQ, HLA-DR, HLA-DM, HLA-DO, or other HLA molecule.

In some cases, the antigen is a self-antigen. A self-antigen can be, for example, an immunoglobulin, a T-cell receptor, an intracellular tumor antigen, an extracellular tumor antigen, an MHC molecule, or an extracellular moiety associated with a condition. For instance, cellular expression of human HLA DR2 is associated with systemic lupus and multiple sclerosis and cellular expression of human HLA DR4 is associated with rheumatoid arthritis and diabetes mellitus.

In other cases, the antigen is a foreign-antigen. A foreign-antigen can be, for example, a virus, a bacteria, a protozoa, or an allergen such as pollen or a food. A foreign antigen can be associated with, for example, an infectious disease, an autoimmune disorder, or with tissue injury.

An engineered γδ T-cell of the disclosure can be designed to home to a specific physical location in the body of a subject and hence target an antigen at a particular tissue, organ or body site. Endogenous T-cells have distinct repertoires of trafficking ligands and receptors that influence their patterns of migration. An engineered γδ T-cell of the disclosure can be designed to express, from the expression cassette comprising the tumor recognition moiety or from a separate expression cassette, one or more trafficking ligand(s), or receptor(s) that guide the migration of the engineered γδ T-cell to a particular tissue, organ, or body site.

An engineered γδ T-cell of the disclosure can be a tumor-specific allogeneic cell. For instance, an engineered γδ T-cell may be derived from a non-engineered γδ T-cell that is a tumor infiltrating lymphocyte (TIL) isolated from a tumor. Different TILs that can be isolated from different tumor types. An expression cassette encoding a tumor recognition moiety, and activation domain, or another engineered featured can be inserted into the genome of a TIL isolated from various tumors. Such γδ T-cells can infiltrate solid tumors, weaken and kill tumors cells expressing one or more target antigens, and they can provide an effective treatment for various malignancies. A tumor specific allogeneic γδ T-cell can be engineered to express at least one tumor recognition moiety that recognizes an epitope of choice. In some cases, a tumor specific allogeneic γδ T-cell is designed to express at least two different tumor recognition moieties, and each different tumor recognition moiety is designed to recognize a different epitope of the same antigen, distinct antigens, an antigen and an activating or inactivating co-stimulatory/immune modulation receptor(s), an antigen in complex with an MHC molecule, or a homing receptor.

In some cases, an engineered γδ T-cell of the disclosure is designed to express specific alleles of the TCR δ and the TCR α receptor chains. Specific alleles of the TCR δ and the TCR α receptor chains of the engineered γδ T-cell may direct the migration, or homing, of the engineered γδ T-cell to one or more physical locations in a subject's body. For instance, in humans, γδ T-cells expressing the Vδ1$^+$ TCR are predominantly restricted to, and home to, epithelial or epithelia-associated/mucosal tissues of the skin, airways, digestive and urogenital tracts and several internal organs. Human γδ T-cells expressing the Vδ3$^+$ TCR are enriched in the liver. An engineered γδ T-cell of the disclosure may be constitutively activated. In wild-type T-cells, the TCRs exist as a complex of several proteins, which include CD3 proteins, such as CD3εγ, CD3εδ, and ζ-chains (CD3ζ homodimer). A number of immunoreceptor tyrosine-based activation motifs (ITAM) on the ζ-chains can be phosphorylated to generate an activation signal on T-lymphocytes. Unlike α/β TCR CD8 and CD4 cells that become activated when they recognize specific antigens associated with MHC class I or class II molecules, respectively, γδ T-cells become activated by recognizing antigens directly in a non-MHC restrictive manner. Such antigens include antigens expressed by tumor cells such as MHC class I chain-related molecules A and B (MICA and MICB), CD1, NKG2A, ULBP1-3, lipids, and phosphoantigens. An engineered γδ T-cell of the disclosure may be engineered to be constitutively active. In some cases, an engineered γδ T-cell of the disclosure is engineered to comprise a tumor recognition moiety and an activation moiety. The activation moiety may be a protein in the TCR-CD3 complex. In some cases, an engineered γδ T-cell of the disclosure constitutively expresses a genetically modified CD3ζ gene, wherein the immunoreceptor tyrosine-based activation motif of the CD3ζ gene is modified to comprise a phosphomimetic of the tyrosine gene in the YxxL/I motif. Various T-cell activation domains and transmembrane domains such as CD3ζ, CD28, CD2, ICOS, 4-1 BB (CD137), OX40 (CD134), CD27, CD70, CD80, CD86, DAP, CD122, FceRIg, CD4, CD3e, JAMAL, NKG2D, or CD16, may be engineered to, for example, comprise a phosphomimetic or another nucleic acid mutation.

Further disclosed herein is a method for the in vitro (ex vivo) expansion of an engineered γδ T-cell of the disclosure. In some cases, an engineered γδ T-cell can be expanded ex vivo without stimulation by an antigen presenting cell or an aminophosphate(s). An antigen reactive engineered T-cell of the disclosure may be expanded ex vivo and in vivo. In some cases, an active population of engineered γδ T-cells of the disclosure may be expanded ex vivo without antigen stimulation by an antigen presenting cell, an antigenic peptide, a non-peptide molecule, or a small molecule compound, such as an aminophosphate(s) but using certain antibodies, cytokines, mitogens, or fusion proteins, such as IL-17 Fc fusion, MICA Fc fusion, and CD70 Fc fusion. Examples of antibodies that can be used in the expansion of a γδ T-cell population include anti-CD3, anti-CD27, anti-CD30, anti-CD70, anti-OX40, anti-NKG2D, or anti-CD2 antibodies, examples of cytokines include IL-2, IL-15, IL-12, or IL-21, IL-18, IL-9, IL-7, IL-33 and examples of mitogens include CD70 the ligand for human CD27, phytohaemagglutinin (PHA), concavalin A (ConA), pokeweed mitogen (PWM), protein peanut agglutinin (PNA), soybean agglutinin (SBA), les culinaris agglutinin (LCA), *Pisum sativum* agglutinin (PSA), *Helix pomatia* agglutinin (HPA), *Vicia graminea* Lectin (VGA) or another suitable mitogen capable of stimulating T-cell proliferation. In some cases, a population of engineered γδ T-cells can be expanded in less than 60 days, less than 48 days, 36 days, less than 24 days, less than 12 days, or less than 6 days.

Further disclosed herein is a method for treating various conditions with an engineered γδ T-cell(s) of the disclosure. An engineered γδ T-cell of the disclosure may be used to treat a subject in need of treatment for a condition. A condition may be a cancer, such as a bladder cancer, a breast cancer, a lung cancer, a prostate cancer, a liver cancer, a skin cancer, a colon and rectal cancer, a lymphoma, a leukemia, multiple myeloma, an ovarian cancer, a sarcoma, a head and neck cancer, a mesothelioma, a brain cancer, a sarcoma or another cancer. A condition may be an infectious disease, an autoimmune disorder, transplantation, or sepsis. Also disclosed herein, is a method for providing an engineered γδ T-cell to a subject. In some cases, an engineered γδ T-cell may be administered to a subject afflicted with a condition. In some cases, an engineered γδ T-cell may be administered to a subject during a procedure, such as a bone marrow transplant. The disclosure further provides a method for administrating an engineered γδ T-cell to a subject without the co-administration of a regulatory cytokine, such as IL-2. In some cases, a γδ T-cell is engineered to express one or more cytokines or hormones that can enhance their proliferation, survival, and function when expanded ex vivo and administered in vivo, such as IL-2, IL-7, IL-15, IL-21, IL-12, IL-18, IL-9. A γδ T-cell can be engineered to express one more cytokines or hormones from the same or from a different expression cassette comprising the recognition moiety. Cytokines include chemokines, interferons, interleukins, and tumor necrosis factors. Non-limiting examples of cytokines include IL-2, IL-7, IL-15, IL-21, IL-12, IL-18, IL-9, erythropoietin (EPO), G-CSF, GM-CSF, thrombopoietin (TPO), and members of the interferon (IFN) subfamily.

In some cases, an engineered γδ T-cell may be administered to a subject as a combination therapy. In some cases, the combination therapy comprises: a) a engineered γδ T-cell of the disclosure; and b) an immune-checkpoint therapy.

Engineered γδ T Cells

Engineered γδ T-cells may be generated with various methods known in the art. An engineered γδ T-cell may be designed to stably express a particular tumor recognition moiety. A polynucleotide encoding an expression cassette that comprises a tumor recognition, or another type of recognition moiety, can be stably introduced into the γδ T-cell by a transposon/transposase system or a viral-based gene transfer system, such as a lentiviral or a retroviral system, or another suitable method, such as transfection, electroporation, transduction, lipofection, calcium phosphate (CaPO$_4$), nanoengineered substances, such as Ormosil, viral delivery methods, including adenoviruses, retroviruses, lentiviruses, adeno-associated viruses, or another suitable method. An antigen specific TCR, either αβ or γδ, can be introduced into the engineered γδ T-cell by stably inserting a polynucleotide comprising a genetic code for the antigen specific TCR into the genome of the γδ T-cell. A polynucleotide encoding a CAR with a tumor recognition moiety may be introduced into the engineered γδ T-cell by stably inserting the polynucleotide into the genome of the γδ T-cell. In some cases, the engineered tumor recognition moiety is an engineered T-cell receptor, and the expression cassette incorporated into the genome of an engineered γδ T-cell comprises a polynucleotide encoding an engineered TCR α (TCR alpha) gene, an engineered TCR β (TCR beta) gene, an TCR δ (TCR delta) gene, or an engineered TCR α (TCR gamma) gene. In some cases, the expression cassette incorporated into the genome of the engineered γδ T-cell comprises a polynucleotide encoding an antibody fragment or an antigen binding portion thereof. In some cases, the antibody fragment or antigen binding fragment thereof is a polynucleotide encoding a whole antibody, an antibody fragment, a single-chain variable fragment (scFv), a single domain antibody (sdAb), a Fab, F(ab)$_2$, an Fc, the light or heavy chains on an antibody, the variable or the constant region of an antibody, or any combination thereof that binds to a cell surface tumor antigen as part of the Chimeric Antigen Receptor (CAR) construct, or a bi-specific construct, comprising a CAR and a T-cell receptor (TCR), or CARs with antibodies directed to different antigens. In some cases, the polynucleotide is derived from a human or from another species. An antibody fragment or antigen binding fragment polynucleotide that is derived from a non-human species can be modified to increase their similarity to antibody variants produced naturally in humans, and an antibody fragment or antigen binding fragment can be partially or fully humanized. An antibody fragment or antigen binding fragment polynucleotide can also be chimeric, for example a mouse-human antibody chimera. An engineered γδ T-cell that expresses a CAR can also be engineered to express a ligand to the antigen recognized by the tumor recognition moiety.

Various techniques known in the art can be used to introduce a cloned, or synthetically engineered, nucleic acid comprising the genetic code for a tumor recognition moiety into a specific location within the genome of an engineered γδ T-cell. The RNA-guided Cas9 nuclease from the microbial clustered regularly interspaced short palindromic repeats (CRISPR) system, zinc finger nucleases (ZFNs), transcription activator-like effector nucleases (TALENs), and meganuclease technologies, as described, respectively by WO201409370, WO2003087341, WO2014134412, and WO2011090804, each of which is incorporated by reference herein in its entireties, can be used to provide efficient genome engineering in γδ T-cell(s). The technologies described herein can also be used to insert the expression cassette into a genomic location that simultaneously provides a knock-out of one gene and a knock-in of another gene. For example, a polynucleotide comprising an expression cassette of the disclosure can be inserted into a genomic region that encodes for an MHC gene. Such engineering can simultaneously provide the knock-in of one or more genes, e.g. the genes comprised in the expression cassette, and a knock-out of another gene, e.g. an MHC locus.

In one case, a Sleeping Beauty transposon that includes a nucleic acid coding for the tumor recognition moiety is introduced into the cell γδ T-cell that is being engineered. A mutant Sleeping Beauty transposase that provides for enhanced integration as compared to the wild-type Sleeping Beauty, such as the transposase described in U.S. Pat. No. 7,985,739, which is incorporated by reference herein in its entirety, may be used to introduce a polynucleotide in the engineered γδ T-cell.

In some cases, a viral method is used to introduce a polynucleotide comprising a tumor recognition moiety into the genome of an engineered γδ T-cell. A number of viral methods have been used for human gene therapy, such as the methods described in WO 1993020221, which is incorporated herein in its entirety. Non-limiting examples of viral methods that can be used to engineer a γδ T-cell include retroviral, adenoviral, lentiviral, herpes simplex virus, vaccinia virus, pox virus, or adeno-virus associated viral methods.

A polynucleotide containing the genetic code for a tumor recognition moiety may comprise mutations or other transgenes that affect the growth, proliferation, activation status of the engineered γδ T-cell or an antigen specific to tumor cells such as testis-specific cancer antigens. A γδ T-cell of the disclosure may be engineered to express a polynucleotide comprising an activation domain that is linked to the antigen recognition moiety, such as a molecule in TCR-CD3 complex or a co-stimulatory factor. An engineered γδ T-cell can express an intracellular signaling domain that is a T-lymphocyte activation domain. The γδ T-cell may be engineered to express an intracellular activation domain gene or an intracellular signaling domain. The intracellular signaling domain gene, may be, for example CD3ζ, CD28, CD2, ICOS, JAMAL, CD27, CD30, OX40, NKG2D, CD4, OX40/ CD134, 4-1BB/CD137, FcεRIγ, ILRB/CD 122, IL-2RG/ CD132, DAP molecules, CD70, cytokine receptor, CD40, or any combination thereof. In some cases, the engineered γδ T-cell is also engineered to express a cytokine, an antigen, a cellular receptor, or other immunomodulatory molecule.

The appropriate tumor recognition moiety to be expressed by the engineered γδ T-cell can be selected based on the disease to be treated. For example, in some cases a tumor recognition moiety is a TCR. In some cases, a tumor recognition moiety is a receptor to a ligand that is expressed on a cancer cell. Non-limiting examples of suitable receptors include NKG2D, NKG2A, NKG2C, NKG2F, LLT1, AICL, CD26, NKRP1, NKp30, NKp44, NKp46, CD244 (2B4), DNAM-1, and NKp80. In some cases, a tumor recognition moiety can include a ligand, e.g. IL-13 ligand, or a ligand mimetic to the tumor antigen, such as the IL-13 mimetic to IL13R.

A γδ T-cell may be engineered to express a chimeric tumor recognition moiety comprising a ligand binding domain derived from NKG2D, NKG2A, NKG2C, NKG2F, LLT1, AICL, CD26, NKRP1, NKp30, NKp44, NKp46, CD244 (2B4), DNAM-1, and NKp80, or an anti-tumor antibody such as anti-Her2neu or anti-EGFR and a signaling domain obtained from CD3-ζ, Dap 10, CD28, 4 IBB, and CD40L. In some examples, the chimeric receptor binds MICA, MICB, Her2neu, EGFR, mesothelin, CD38, CD20, CD 19, PSA, RON, CD30, CD22, CD37, CD38, CD56, CD33, CD30, CD138, CD123, CD79b, CD70, CD75, CA6, GD2, alphafetoprotein (AFP), carcinoembryonic antigen (CEA), CEACAM5, CA-125, MUC-16, 5T4, NaPi2b, ROR1, ROR2, 5T4, PLIF, Her2/Neu, EGFRvIII, GPMNB, LIV-1, glycolipidF77, fibroblast activating protein, PSMA, STEAP-1, STEAP-2, c-met, CSPG4, Nectin-4, VEGFR2, PSCA, folate binding protein/receptor, SLC44A4, Cripto, CTAG1B, AXL, IL-13R, IL-3R, SLTRK6, gp100, MART1, Tyrosinase, SSX2, SSX4, NYESO-1, epithelial tumor antigen (ETA), MAGEA family genes (such as MAGE3A. MAGE4A), KKLC1, mutated ras, βraf, p53, MHC class I chain-related molecule A (MICA), or MHC class I chain-related molecule B (MICB), HPV, CMV.

Two or more tumor recognition moieties may be expressed in the γδ T-cell from genetically different, substantially different, or substantially identical, αβ TCR polynucleotides stably expressed from the engineered γδ T-cell or from genetically distinct αβ TCR polynucleotides stably incorporated in the engineered γδ T-cell. In the case of genetically distinct αβ TCR(s), αβ TCR(s) recognizing different antigens associated with the same condition may be utilized. In one preferred embodiment, a γδ T-cell is engineered to express different TCRs, from human or mouse origin, from one or more expression cassettes that recognize the same antigen in the context of different MHC haplotypes. In another preferred embodiment, a γδ T-cell is engineered to express one TCR and two or more antibodies directed to the same or different peptides from a given antigen complexed with different MHC haplotypes. In some cases, expression of a single TCR by an engineered γδ T-cell facilitates proper TCR pairing. An engineered γδ T-cell that expresses different TCRs can provide a universal allogeneic engineered γδ T-cell. In a second preferred embodiment, a γδ T-cell is engineered to express one or more different antibodies directed to peptide-MHC complexes, each directed to the same or different peptide complexed with the same or different MHC haplotypes. In some cases, a tumor recognition moiety can be an antibody that binds to peptide-MHC complexes.

A γδ T-cell can be engineered to express TCRs from one or more expression cassettes that recognize the same antigen in the context of different MHC haplotypes. In some cases, an engineered γδ T-cell is designed to express a single TCR, or a TCR in combination with a CAR to minimize the likelihood of TCR mispairing within the engineered cell. The tumor recognition moieties expressed from two or more expression cassettes preferably have different polynucleotide sequences, and encode tumor recognition moieties that recognize different epitopes of the same target. An engineered γδ T-cell that expresses such different TCRs or CARs can provide a universal allogeneic engineered γδ T-cell.

In some cases, a γδ T-cell is engineered to express one or more tumor recognition moieties. Two or more tumor recognition moieties may be expressed from genetically identical, or substantially identical, antigen-specific chimeric (CAR) polynucleotides engineered in the γδ T-cell. Two or more tumor recognition moieties may be expressed from genetically distinct CAR polynucleotides engineered in the γδ T-cell. The genetically distinct CAR(s) may be designed to recognize different antigens associated with the same condition.

A γδ T-cell may alternatively be bi-specific. A bi-specific engineered γδ T-cell can express two or more tumor recognition moieties. A bi-specific engineered γδ T-cell can express both TCR and CAR tumor recognition moieties. A bi-specific engineered γδ T-cell can be designed to recognize different antigens associated with the same condition. An engineered γδ T-cell can express two or more CAR/TCR(s) bi-specific polynucleotides that recognize an identical or substantially identical antigen. An engineered γδ T-cell can express two or more CAR/TCR(s) bi-specific constructs that recognize distinct antigens. In some cases, a bi-specific construct of the disclosure binds to an activating and an inactivating domain of a target cell, thereby providing increased target specificity. The γδ T-cell may be engineered to express at least 1 tumor recognition moiety, at least 2 tumor recognition moieties, at least 3 tumor recognition moieties, at least 4 tumor recognition moieties, at least 5 tumor recognition moieties, at least 6 tumor recognition moieties, at least 7 tumor recognition moieties, at least 8 tumor recognition moieties, at least 9 tumor recognition moieties, at least 10 tumor recognition moieties, at least 11 tumor recognition moieties, at least 12 tumor recognition moieties, or another suitable number of tumor recognition moieties.

Proper TCR function may be enhanced by two functioning ζ (zeta) proteins comprising ITAM motifs. Proper TCR function may also be enhanced by expression of αβ or γδ activation domains, such as CD28, CD2, CTLA4, ICOS, JAMAL, PD-1, CD27, CD30, 41-BB, OX40, NKG2D, HVEM, or CD46. The expressed polynucleotide may include the genetic code for a tumor recognition moiety, a linker moiety, and an activation domain. Translation of the polynucleotide by the engineered γδ T-cell may provide a tumor recognition moiety and an activation domain linked by a protein linker. Often, the linker comprises amino acids that do not obstruct the folding of the tumor recognition moiety and the activation domain. A linker molecule can be at least about 5 amino acids, about 6 amino acids, about 7 amino acids, about 8 amino acids, about 9 amino acids, about 10 amino acids, about 11 amino acids, about 12 amino acids, about 13 amino acids, about 14 amino acids, about 15 amino acids, about 16 amino acids, about 17 amino acids, about 18 amino acids, about 19 amino acids, or about 20 amino acids in length. In some cases, at least 50%, at least 70% or at least 90% of the amino acids in the linker are serine or glycine.

In some cases, an activation domain can comprise one or more mutations. Suitable mutations may be, for example, mutations that render an activation domain constitutively active. Altering the identity of one or more nucleic acids changes the amino acid sequence of the translated amino acid. A nucleic acid mutation can be made such that the encoded amino acid is modified to a polar, non-polar, basic or acidic amino acid. A nucleic acid mutation can be made such that the tumor recognition moiety is optimized to recognize an epitope from a tumor. The engineered tumor recognition moiety, an engineered activation domain, or another engineered component of a γδ T-cell may include more than 1 amino acid mutation, 2 amino acid mutations, 3 amino acid mutations, 4 amino acid mutations, 5 amino acid mutations, 6 amino acid mutations, 7 amino acid mutations, 8 amino acid mutations, 9 amino acid mutations, 10 amino acid mutations, 11 amino acid mutations, 12 amino acid mutations, 13 amino acid mutations, 14 amino acid mutations, 15 amino acid mutations, 16 amino acid mutations, 17 amino acid mutations, 18 amino acid mutations, 19 amino acid mutations, 20 amino acid mutations, 21 amino acid mutations, 22 amino acid mutations, 23 amino acid mutations, 24 amino acid mutations, 25 amino acid mutations, 26 amino acid mutations, 27 amino acid mutations, 28 amino acid mutations, 29 amino acid mutations, 30 amino acid mutations, 31 amino acid mutations, 32 amino acid mutations, 33 amino acid mutations, 34 amino acid mutations, 35 amino acid mutations, 36 amino acid mutations, 37 amino acid mutations, 38 amino acid mutations, 39 amino acid mutations, 40 amino acid mutations, 41 amino acid mutations, 42 amino acid mutations, 43 amino acid mutations, 44 amino acid mutations, 45 amino acid mutations, 46 amino acid mutations, 47 amino acid mutations, 48 amino acid mutations, 49 amino acid mutations, or 50 amino acid mutations.

In some cases, a γδ T-cell of the disclosure does not express one or more MHC molecules. Deletion of one or more MHC loci in an engineered γδ T-cell can decrease the likelihood that the engineered γδ T-cell will be recognized by the host immune system. The human Major Histocompatibility Complex (MHC) loci, known as the human leukocyte antigen (HLA) system, comprises a large gene family that is expressed in antigen presenting cells, including γδ T-cells. The HLA-A, HLA-B, and HLA-C molecules function to present intracellular peptides as antigens to antigen presenting cells. The HLA-DP, HLA-DM, HLA-DOA, HLA-DOB, HLA-DQ, and HLA DR molecules function to present extracellular peptides as antigens to antigen presenting cells. Some alleles of the HLA genes have been associated with GVHD, autoimmune disorders, and cancer. An engineered γδ T-cell described herein can be further engineered to lack, or to disrupt gene expression of one or more HLA genes. An engineered γδ T-cell described herein can be further engineered to lack, or to disrupt gene expression of one or more components of the MHC complex, such as complete deletion of one or more of the MHC genes, deletion of specific exons, or deletion of the $\beta_2$ microglobulin (B2m). Genetic excision or genetic disruption of at least one HLA gene can provides a clinically therapeutic γδ T-cell that can be administered to a subject with any HLA haplotype without causing host-versus-graft disease. An engineered γδ T-cell as described herein can be a universal donor for a human subject with any HLA haplotype.

A γδ T-cell can be engineered to lack one or various HLA locus (loci). An engineered γδ T-cell can be engineered to lack an HLA-A allele, an HLA-B allele, an HLA-C allele, an HLA-DR allele, an HLA-DQ allele, or an HLA-DP allele. In some cases, an HLA allele is associated with a human condition, such as an auto-immune condition. For instance, the HLA-B27 allele has been associated with arthritis and uveitis, the HLA-DR2 allele has been associated with systemic lupus erythematosus, the HLA-DR3 allele has been associated with 21-hydroxylase deficiency, the HLA-DR4 has been associated with rheumatoid arthritis and type 1 diabetes. An engineered γδ T-cell that lacks, for example, the HLA-B27 allele can be administered to a subject afflicted with arthritis without being readily recognized the immune system of the subject. In some cases, deletion of one or more HLA loci provides an engineered γδ T-cell that is a universal donor for any subject with any HLA haplotype.

In some cases, engineering a γδ T-cell requires the deletion of a portion of the γδ T-cell genome. In some cases, the deleted portion of the genome comprises a portion of the MHC locus (loci). In some instances, the engineered γδ T-cell is derived from a wild-type human γδ T-cell, and the MHC locus is an HLA locus. In some cases, the deleted a portion of the genome comprises a portion of a gene corresponding to a protein in the MHC complex. In some cases, the deleted portion of the genome comprises the β2 microglobulin gene. In some instances, the deleted portion of the genome comprises an immune checkpoint gene, such as PD-1, CTLA-4, LAG3, ICOS, BTLA, KIR, TIM3, A2aR, B7-H3, B7-H4, and CECAM-1. In some cases, an engineered γδ T-cell can be designed to express an activation domain that enhances T-cell activation and cytotoxicity. Non-limiting examples of activation domains that can be expressed by an engineered γδ T-cell include: CD2, ICOS, 4-1 BB (CD137), OX40 (CD134), CD27, CD70, CD80, CD86, DAP, CD122, GITR, FceRIg.

Any portion of the genome of an engineered γδ T-cell can be deleted to disrupt the expression of an endogenous γδ T-cell gene. Non-limiting examples of genomic regions that can be deleted or disrupted in the genome of an γδ T-cell include a promoter, an activator, an enhancer, an exon, an intron, a non-coding RNA, a micro-RNA, a small-nuclear RNA, variable number tandem repeats (VNTRs), short tandem repeat (STRs), SNP patterns, hypervariable regions, minisatellites, dinucleotide repeats, trinucleotide repeats, tetranucleotide repeats, or simple sequence repeats. In some cases, the deleted a portion of the genome ranges between 1 nucleic acid to about 10 nucleic acids, 1 nucleic acid to about 100 nucleic acids, 1 nucleic acid to about 1,000 nucleic acids, 1 nucleic acid to about 10,000 nucleic acids, 1 nucleic acid to about 100,000 nucleic acids, 1 nucleic acid to about 1,000,000 nucleic acids, or other suitable range.

HLA gene expression in an engineered γδ T-cell can also be disrupted with various techniques known in the art. In some cases, large loci gene editing technologies are used to excise a gene from the engineered γδ T-cell genome, or to disrupt gene expression of at least one HLA locus in the engineered γδ T-cell. Non-limiting examples of gene editing technologies that can be used to edit a desired locus on a genome of an engineered γδ T-cell include Clustered Regularly Interspaced Short Palindromic Repeats (CRISPR)-Cas, zinc finger nucleases (ZFNs), Transcription activator-like effector nucleases (TALENs), and meganuclease technologies, as described, respectively by WO201409370, WO2003087341, WO2014134412, and WO 2011090804, and each of which is incorporated by reference herein in its entireties.

A γδ T-cell may be engineered from an isolated non-engineered γδ T-cell that already expresses a tumor recognition moiety. The engineered γδ T-cell can retain a tumor cell recognition moiety that is endogenously expressed by the isolated wild-type γδ T-cell. In some cases, the engineered γδ T-cell tumor cell recognition moiety replaces the wild-type γδ TCR.

A γδ T-cell can be engineered to express one or more homing molecules, such as a lymphocyte homing molecule. Homing molecules can be, for instance, lymphocyte homing receptors or cell adhesion molecules. A homing molecule can help an engineered γδ T-cell to migrate and infiltrate a solid tumor, including a targeted solid tumor upon administration of the engineered γδ T-cell to the subject. Non-limiting examples of homing receptors include members of the CCR family, e.g: CCR2, CCR4, CCR7, CCR8, CCR9, CCR10, CLA, CD44, CD103, CD62L, E-selectin, P-selectin, L-selectin, integrins, such as VLA-4 and LFA-1. Non-limiting examples of cell adhesion molecules include ICAM, N-CAM, VCAM, PE-CAM, L1-CAM, Nectin (PVRL1, PVRL2, PVRL3), LFA-1, integrin alphaXbeta2, alphavbeta7, macrophage-1 antigen, CLA-4, glycoprotein IIb/IIIa. Additional examples of cell adhesion molecules include calcium dependent molecules, such as T-cadherin, and antibodies to matrix metaloproteinases (MMPs) such as MMP9 or MMP2.

The steps involved in T-cell maturation, activation, proliferation, and function may be regulated through co-stimulatory and inhibitory signals through immune checkpoint proteins. Immune checkpoints are co-stimulatory and inhibitory elements intrinsic to the immune system. Immune checkpoints aid in maintaining self-tolerance and modulating the duration and amplitude of physiological immune responses to prevent injury to tissues when the immune system responds to disease conditions, such as cell transformation or infection. The equilibrium between the co-stimulatory and inhibitory signals used to control the immune response from either γδ and αβ T-cells can be modulated by immune checkpoint proteins. Immune checkpoint proteins, such as PD1 and CTLA4 are present on the surface of T-cells and can be used to turn an immune response "on" or "off." Tumors can dysregulate checkpoint protein function as an immune-resistance mechanism, particularly against T-cells that are specific for tumor antigens. An engineered γδ T-cell of the disclosure can be further engineered to lack one or more immune checkpoint locus (loci), such as PD-1, CTLA-4, LAG3, ICOS, BTLA, KIR, TIM3, A2aR, CEACAM1, B7-H3, and B7-H4. Alternatively, the expression of an endogenous immune check point gene in an engineered γδ T-cell of the disclosure can be disrupted with gene editing technologies.

Immunological checkpoints can be molecules that regulate inhibitory signaling pathways (exemplified by CTLA4, PD1, and LAG3) or molecules that regulate stimulatory signaling pathways (exemplified by ICOS) in an engineered γδ T-cell of the disclosure. Several proteins in the extended immunoglobulin superfamily can be ligands for immunological checkpoints. Non-limiting examples of immune checkpoint ligand proteins include B7-H4, ICOSL, PD-L1, PD-L2, MegaCD40L, MegaOX40L, and CD137L. In some cases, immune checkpoint ligand proteins are antigens expressed by a tumor. In some cases, the immune checkpoint gene is a CTLA-4 gene. In some cases, the immune checkpoint gene is a PD-1 gene.

PD1 is an inhibitory receptor belonging to the CD28/CTLA4 family and is expressed on activated T lymphocytes, B cells, monocytes, DCs, and T-regs. There are two known ligands for PD1, PD-L1 and PD-L2, which are expressed on T cells, APCs, and malignant cells function to suppress self-reactive lymphocytes and to inhibit the effector function of TAA-specific cytotoxic T lymphocytes (CTLs). Accordingly, an engineered γδ T-cell that lacks PD1 can retain its cytotoxic activity regardless of expression of PD-L1 and PD-L2 by tumor cells. In some cases, an engineered γδ T-cell of the disclosure lacks the gene locus for the PD-1 gene. In some cases, expression of the PD-1 gene in an engineered γδ T-cell is disrupted by gene editing technologies.

CTLA4 (cytotoxic T-lymphocyte antigen 4) is also known as CD152 (Cluster of differentiation 152). CTLA4 shares sequence homology and ligands (CD80/B7-1 and CD86/B7-2) with the costimulatory molecule CD28, but differs by delivering inhibitory signals to T-cells expressing CTLA4 as a receptor. CTLA4 has a much higher overall affinity for both ligands and can out-compete CD28 for binding when ligand densities are limiting. CTLA4 is often expressed on the surface of $CD8^+$ effector T-cells, and plays a functional role in the initial activation stages of both naive and memory T-cells. CTLA4 counteracts the activity of CD28 via increased affinity for CD80 and CD86 during the early stages of T-cell activation. The major functions of CTLA4 include down-modulation of helper T-cells and enhancement of regulatory T-cell immunosuppressive activity. In some instances, an engineered γδ T-cell of the disclosure lacks the CTLA4 gene. In some cases, expression of the CTLA4 gene in an engineered γδ T-cell is disrupted by gene editing technologies.

LAG3 (Lymphocyte-activation gene 3) is expressed on activated antigen-specific cytotoxic T-cells, and can enhance the function of regulatory T-cells and independently inhibit $CD8^+$ effector T-cell activity. LAG3 is a CD-4-like negative regulatory protein with a high affinity binding to MHC Class II proteins, which are upregulated on some epithelial cancers, leading to tolerance of T cell proliferation and homeostasis. Reduction of the LAG-3/Class II interaction using a LAG-3-IG fusion protein may enhance antitumor immune responses. In some cases, an engineered γδ T-cell of the disclosure lacks the gene locus for the LAG3 gene. In some instances, expression of the LAG3 gene in an engineered γδ T-cell is disrupted by gene editing technologies.

Phenotype of Engineered γδ T-Cells

An engineered γδ T-cell may home to a specific physical location in a subject's body. Migration and homing of engineered γδ T cells, can be dependent on the combined expression and actions of specific chemokines and/or adhesion molecules. Homing of engineered γδ T cells can be controlled by the interactions between chemokines and their receptors. For example, cytokines including but not limited to CXCR3 (whose ligands are represented by IP-10/CXCL10 and 6Ckine/SLC/CCL21) CCR4+CXCR5+(receptor for RANTES, MIP-1α, MIP-1β) CCR6+ and CCR7 may affect homing of engineered γδ T cells. In some cases, an engineered γδ T-cell may home to sites of inflammation and injury, and to diseased cells to perform repair functions. In some cases, an engineered γδ T-cell can home to a cancer. In some cases, an engineered γδ T-cell may home to a thymus, a bone marrow, a skin, a larynx, a trachea, pleurae, a lung, an esophagus, an abdomen, a stomach, a small intestine, a large intestine, a liver, a pancreas, a kidney, a urethra, a bladder, a testes, a prostate, a ductus deferens, am ovary, an uretus, a mammary gland, a parathyroid gland, a spleen or another site in a subject's body. An engineered γδ T-cell can express one or more homing moieties, such as particular TCR allele and/or a lymphocyte homing molecule.

An engineered γδ T-cell may have a particular phenotype and a phenotype can be described in terms of cell-surface marker expression. Various types of γδ T-cells can be engineered as described herein. In preferred embodiments, the engineered γδ T-cell is derived from a human, but the engineered γδ T-cell may also be derived from a different source, such as a mammal or a synthetic cell.

Antigens

The invention disclosed herein provides an engineered γδ T-cell that expresses an antigen recognition moiety, wherein the antigen recognition moiety recognizes a disease-specific epitope. An antigen may be a molecule that provokes an immune response. This immune response may involve either antibody production, the activation of specific immunologically-competent cells, or both. An antigen may be, for example, a peptide, a protein, a hapten, a lipid, a carbohydrate, bacteria, a pathogen, or a virus. An antigen may be a tumor antigen. A tumor epitope may be presented by the MHC I or MHC II complexes on the surface of tumor cells. An epitope can be the portion of the antigen that is expressed on the cell surface and recognized by the tumor recognition moiety.

Non-limiting examples of antigens recognized by an engineered γδ T-cell include CD-19, CD-30, CD-22, CD37, CD38, CD-33, CD-138, CD-123, CD-79b, CD-70, CD-75, CA6, GD2, alphafetoprotein, carcinoembryonic antigen, CA-125, MUC-16, 5T4, NaPi2b, ROR1, ROR2, 5T4, Her2/Neu, EGFRvIII, GPMNB, LIV-1, glycolipidF77, fibroblast activating protein, PSMA, STEAP-1, STEAP-2, mesothelin, c-met, CSPG4, Nectin-4, VEGFR2, PSCA, folate binding protein receptor, SLC44A4, Cripto, CTAG1B, AXL, IL-13R, IL-3R, SLTRK6, gp100, MART1, Tyrosinase, SSX2, SSX4, NYESO-1, epithelial tumor antigen, MAGEA, KKLC1, mutated ras, βraf, p53, MICA and MICB, or another antigen associated with a condition. See revised list—CD 19, CD30, CD22, CD37, CD38, CD56, CD33, CD30, CD138, CD123, CD79b, CD70, CD75, CA6, GD2, alphafetoprotein (AFP), carcinoembryonic antigen (CEA), RON, CEACAM5, CA-125, MUC-16, 5T4, NaPi2b, ROR1, ROR2, 5T4, PLIF, Her2/Neu, EGFRvIII, GPMNB, LIV-1, glycolipidF77, fibroblast activating protein, PSMA, STEAP-1, STEAP-2, mesothelin, c-met, CSPG4, Nectin-4, VEGFR2, PSCA, folate binding protein/receptor, SLC44A4, Cripto, CTAG1B, AXL, IL-13R, IL-3R, SLTRK6, gp100, MART1, Tyrosinase, SSX2, SSX4, NYESO-1, epithelial tumor antigen (ETA), MAGEA family genes (such as MAGE3A. MAGE4A), KKLC1, mutated ras, βraf, p53, MHC class I chain-related molecule A (MICA), or MHC class I chain-related molecule B (MICB), HPV, CMV.

An antigen can be expressed in the intracellular or the extracellular compartment of a cell and an engineered γδ T-cell can recognize an intracellular or an extracellular tumor antigen. In some cases, an αβ TCR in the engineered γδ T-cell recognizes a peptide derived from either an intracellular or an extracellular tumor antigen. For example, an antigen may be a protein intracellularly or extracellularly produced by a cell infected with a virus, such as an HIV, an EBV, a CMV, or an HPV protein. An antigen may also be a protein intracellularly or extracellularly expressed by a cancerous cell.

An antigen recognition moiety may recognize an antigen from a cell in distress, such as a cancerous cell or a cell that has been infected with a virus. For instance, the human MHC class I chain-related genes (MICA and MICB) are located within the HLA class I region of chromosome 6. MICA and MICB proteins are considered to be markers of "stress" in the human epithelia, and act as ligands for cells expressing a common natural killer-cell receptor (NKG2D). As stress markers, MICA and MICB can be highly expressed from cancerous cells. An engineered γδ T-cell can recognize a MICA or a MICB tumor epitope.

A tumor recognition moiety may be engineered to recognize an antigen with certain avidity. For instance, a tumor recognition moiety encoded by a TCR or CAR construct may recognize an antigen with a dissociation constant of at least at least 10 fM, at least 100 fM, at least 1 picomolar (pM), at least 10 pM, at least 20 pM, at least 30 pM, at least 40 pM, at least 50 pM, at least 60 pM, at least 7 pM, at least 80 pM, at least 90 pM, at least 100 pM, at least 200 pM, at least 300 pM, at least 400 pM, at least 500 pM, at least 600 pM, at least 700 pM, at least 800 pM, at least 900 pM, at least 1 nanomolar (nM), at least 2 nM, at least 3 nM, at least 4 nM, at least 5 nM, at least 6 nM, at least 7 nM, at least 8 nM, at least 9 nM, at least 10 nM, at least 20 nM, at least 30 nM, at least 40 nM, at least 50 nm, at least 60 nM, at least 70 nM, at least 80 nM, at least 90 nM, at least 100 nM, at least 200 nM, at least 300 nM, at least 400 nM, at least 500 nM, at least 600 nM, at least 700 nM, at least 800 nM, at least 900 nM, at least 1 μM, at least 2 μM, at least 3 μM, at least 4 μM, at least 5 μM, at least 6 μM, at least 7 μM, at least 8 μM, at least 9 μM, at least 10 μM, at least 20 μM, at least 30 μM, at least 40 μM, at least 50 μM, at least 60 μM, at least 70 μM, at least 80 μM, at least 90 μM, or at least 100 μM.

In some instances, a tumor recognition moiety may be engineered to recognize an antigen with a dissociation constant of at most 10 fM, at most 100 fM, at most 1 picomolar (pM), at most 10 pM, at most 20 pM, at most 30 pM, at most 40 pM, at most 50 pM, at most 60 pM, at most 7 pM, at most 80 pM, at most 90 pM, at most 100 pM, at most 200 pM, at most 300 pM, at most 400 pM, at most 500 pM, at most 600 pM, at most 700 pM, at most 800 pM, at most 900 pM, at most 1 nanomolar (nM), at most 2 nM, at most 3 nM, at most 4 nM, at most 5 nM, at most 6 nM, at most 7 nM, at most 8 nM, at most 9 nM, at most 10 nM, at most 20 nM, at most 30 nM, at most 40 nM, at most 50 nm, at most 60 nM, at most 70 nM, at most 80 nM, at most 90 nM, at most 100 nM, at most 200 nM, at most 300 nM, at most 400 nM, at most 500 nM, at most 600 nM, at most 700 nM, at most 800 nM, at most 900 nM, at most 1 μM, at most 2 μM, at most 3 μM, at most 4 μM, at most 5 μM, at most 6 μM, at most 7 μM, at most 8 μM, at most 9 μM, at most 10 μM, at most 20 μM, at most 30 μM, at most 40 μM, at most 50 μM, at most 60 μM, at most 70 μM, at most 80 μM, at most 90 μM, or at most 100 μM.

Isolation of γδ T-Cells

In some aspects, the present disclosure provides methods for the genetic engineering of γδ T-cells that have been isolated from a subject. A γδ T-cell can be isolated from a complex sample of a subject. A complex sample can be a peripheral blood sample, a cord blood sample, a tumor, a stem cell precursor, a tumor biopsy, a tissue, a lymph, or from epithelial sites of a subject directly contacting the external milieu, or derived from stem precursor cells. A γδ T-cell may be directly isolated from a complex sample of a subject, for example, by sorting γδ T-cell(s) that express one or more cell surface markers with flow cytometry techniques. Wild-type γδ T-cells exhibit numerous antigen recognition, antigen-presentation, co-stimulation, and adhesion molecules that can be associated with a γδ T-cell(s). One or more cell surface markers such as specific γδ TCRs, antigen recognition, antigen-presentation, ligands, adhesion molecules, or co-stimulatory molecules may be used to isolate a wild-type γδ T-cell from a complex sample. Various molecules associated with, or expressed by, a γδ T-cell may be used to isolate a γδ T-cell from a complex sample. In some cases, the present disclosure provides methods for isolation of mixed population of Vδ1+, Vδ2+, Vδ3+ cells or any combination thereof.

Peripheral blood mononuclear cells can be collected from a subject, for example, with an apheresis machine, including the Ficoll-Paque™ PLUS (GE Healthcare) system, or another suitable device/system. γδ T-cell(s), or a desired subpopulation of γδ T-cell(s), can be purified from the collected sample with, for example, with flow cytometry techniques. Cord blood cells can also be obtained from cord blood during the birth of a subject.

Positive and/or negative selection of cell surface markers expressed on the collected γδ T-cell(s) can be used to directly isolate a γδ T-cell, or a population of γδ T-cell(s) expressing similar cell surface markers from a peripheral blood sample, a cord blood sample, a tumor, a tumor biopsy, a tissue, a lymph, or from an epithelial sample of a subject. For instance, a γδ T-cell can be isolated from a complex sample based on positive or negative expression of CD2, CD3, CD4, CD8, CD24, CD25, CD44, Kit, TCR α, TCR β, TCR α, TCR δ, NKG2D, CD70, CD27, CD30, CD16, CD337 (NKp30), CD336 (NKp46), OX40, CD46, CCR7, and other suitable cell surface markers.

A γδ T-cell may be isolated from a complex sample that is cultured in vitro. In some embodiments, whole PBMC population, without prior depletion of specific cell populations such as monocytes, αβ T-cells, B-cells, and NK cells, can be activated and expanded. In other embodiments, enriched γδ T-cell populations can be generated prior to their specific activation and expansion. In some aspects, activation and expansion of γδ T-cell are performed without the presence of native or engineered APCs. In some aspects, isolation and expansion of γδ T cells from tumor specimens can be performed using immobilized γδ T cell mitogens, including antibodies specific to γδ TCR, and other γδ TCR activating agents, including lectins.

In some embodiments, γδ T-cell(s) can rapidly expand in response to contact with one or more antigens. Some γδ T-cell(s), such as Vγ9Vδ2+ γδ T-cell(s) rapidly expand in vitro in response to contact with some antigens, like prenyl-pyrophosphates, alkyl amines, and metabolites or microbial extracts during tissue culture. In addition, some wild-type γδ T-cell(s), such as Vγ2Vδ2+ γδ T-cell(s) rapidly expand in vivo in humans in response to certain types of vaccination(s). Stimulated γδ T-cells can exhibit numerous antigen-presentation, co-stimulation, and adhesion molecules that can facilitate the isolation of a γδ T-cell(s) from a complex sample. A γδ T-cell(s) within a complex sample can be stimulated in vitro with at least one antigen for 1 day, 2 days, 3 days, 4 days, 5 days, 6 days, 7 days, or another suitable period of time. Stimulation of the γδ T-cell with a suitable antigen can expand the γδ T-cell population in vitro.

Non-limiting examples of antigens that may be used to stimulate the expansion of γδ T-cell(s) from a complex sample in vitro include, prenyl-pyrophosphates, such as isopentenyl pyrophosphate (IPP), alkyl-amines, metabolites of human microbial pathogens, metabolites of commensal bacteria, -methyl-3-butenyl-1-pyrophosphate (2M3B1PP), (E)-4-hydroxy-3-methyl-but-2-enyl pyrophosphate (HMB-PP), ethyl pyrophosphate (EPP), farnesyl pyrophosphate (FPP), dimethylallyl phosphate (DMAP), dimethylallyl pyrophosphate (DMAPP), ethyl-adenosine triphosphate (EPPPA), geranyl pyrophosphate (GPP), geranylgeranyl pyrophosphate (GGPP), isopentenyl-adenosine triphosphate (IPPPA), monoethyl phosphate (MEP), monoethyl pyrophosphate (MEPP), 3-formyl-1-butyl-pyrophosphate (TU-BAg 1), X-pyrophosphate (TUBAg 2), 3-formyl-1-butyl-uridine triphosphate (TUBAg 3), 3-formyl-1-butyl-deoxythymidine triphosphate (TUBAg 4), monoethyl alkylamines, allyl pyrophosphate, crotoyl pyrophosphate, dimethylallyl-γ-uridine triphosphate, crotoyl-γ-uridine triphosphate, allyl-γ-uridine triphosphate, ethylamine, isobutylamine, sec-butylamine, iso-amylamine and nitrogen containing bisphosphonates.

Figure 4:
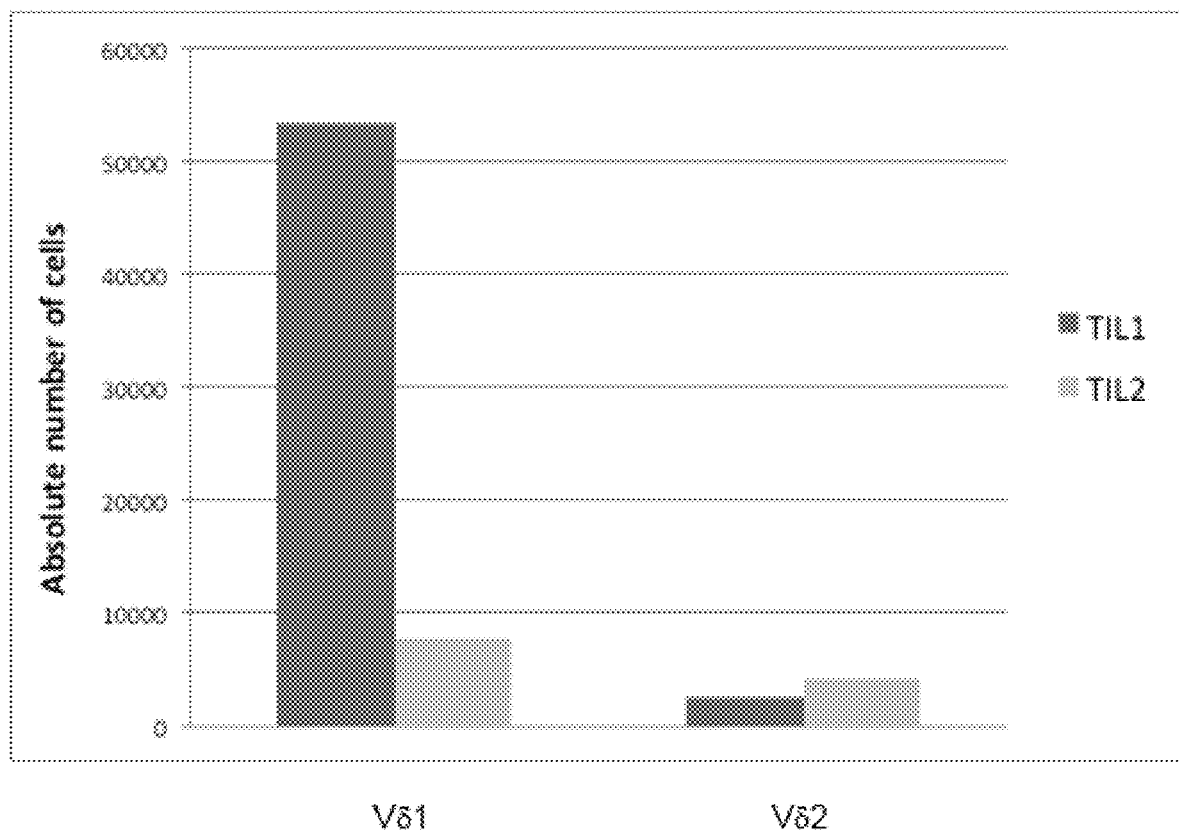
FIG. 4 depicts a graph illustrating growth of γδ1 and γδ2 lymphocytes isolated from colon adenocarcinoma metastasis to liver (TIL 1) and renal tumors (TIL 2) and have been shown to express CCR4 and CCR7.

Activation and expansion of γδ T-cells can be performed using activation and co-stimulatory agents described herein to trigger specific γδ T-cell proliferation and persistence populations. In some embodiments, activation and expansion of γδ T-cells from different cultures can achieve distinct clonal or mixed polyclonal population subsets. In some embodiments, different agonist agents can be used to identify agents that provide specific γδ activating signals. In one aspect, agents that provide specific γδ activating signals can be different monoclonal antibodies (MAbs) directed against the γδ TCRs. In one aspect, the MAbs can bind to different epitopes on the constant or variable regions of γ TCR and/or δ TCR. In one aspect, the MAbs can include γδ TCR pan MAbs. In one aspect, the γδ TCR pan MAbs may recognize domains shared by different γ and δ TCRs on both, including δ1 and δ2 cell populations. In one aspect, the antibodies may be 5A6.E9 (Thermo scientific), B1 (Biolegend), IMMU510 and/or 11F12 (Beckman Coulter). In one aspect, the MAbs can be directed to specific domains unique to the variable regions of the γ chain (7A5 Mab, directed to like Vγ9 TCR (Thermo Scientific #TCR1720)), or domains on Vδ1 variable region (Mab TS8.2 (Thermo scientific #TCR1730; MAb TC1, MAb R9.12 (Beckman Coulter)), or Vδ2 chain (MAb 15D (Thermo Scientific #TCR1732)). The ability of these MAbs to specifically activate and expand unique population Vδ1 or the Vδ2 cell subsets was tested (FIG. 4). FIG. 4 depicts δ2 T-Cells growth in serum-containing media (R2: RPMI+10% FBS) and serum-free media (AIMV+bovine albumin; CTS Optimizer serum-free media with CTS serum-free Supplement). All media contain 100 IU/mL IL-2, 2 mM glutamine and 1× penicillin/streptomycin. Cells were stimulated with Zoledronic acid at 1, 5 and 20 μM on day 0. Media was replenished every 2-3 days without further addition of Zoledronic acid. Total δ2 T-Cells expanded from $10^6$ PBMC and fold expansion after 13 days are indicated for each condition. In some embodiments, antibodies against different domains of the γδ TCR (pan antibodies and antibodies recognizing specific variable region epitopes on subset populations) can be combined to evaluate their ability to enhanced activation of γδ T cells. In some embodiments, γδ T-cells activators can include γδ TCR-binding agents such as MICA, agonist antibody to NKG2D, (Fc tag) fusion protein of MICA, ULBP1, ULBP3 (R&D systems Minneapolis, Minn.) ULBP2, or ULBP6 (Sino Biological Beijing, China). In some embodiments, companion co-stimulatory agents to assist in triggering specific γδ T cell proliferation without induction of cell anergy and apoptosis can be identify. These co-stimulatory agents can include ligands to receptors expressed on γδ cells, such as NKG2D, CD161, CD70, JAML, DNAX accessory molecule-1 (DNAM-1) ICOS, CD27, CD137, CD30, HVEM, SLAM, CD122, DAP, and CD28-. In some aspects, co-stimulatory agents can be antibodies specific to unique epitopes on CD2 and CD3 molecules. CD2 and CD3 can have different conformation structures when expressed on αβ or γδ T-cells (s), and in some cases, specific antibodies to CD3 and CD2 can lead to distinct activation of γδ T-cells.

A population of γδ T-cell(s) may be expanded ex vivo prior to engineering of the γδ T-cell(s). Non-limiting example of reagents that can be used to facilitate the expansion of a γδ T-cell population in vitro include anti-CD3 or anti-CD2, anti-CD27, anti-CD30, anti-CD70, anti-OX40 antibodies, IL-2, IL-15, IL-12, IL-9, IL-33, IL-18, or IL-21, CD70 (CD27 ligand), phytohaemagglutinin (PHA), concavalin A (ConA), pokeweed (PWM), protein peanut agglutinin (PNA), soybean agglutinin (SBA), Les Culinaris Agglutinin (LCA), *Pisum sativum* Agglutinin (PSA), *Helix pomatia* agglutinin (HPA), *Vicia graminea* Lectin (VGA), or another suitable mitogen capable of stimulating T-cell proliferation. Genetic engineering of the γδ T-cell(s) may comprise stably integrating a construct expressing a tumor recognition moiety, such as an αβ TCR, a γδ TCR, a CAR encoding an antibody, an antigen binding fragment thereof, or a lymphocyte activation domain into the genome of the isolated γδ T-cell(s), a cytokine (IL-15, IL-12, IL-2. IL-7. IL-21, IL-18, IL-19, IL-33, IL-4, IL-9, IL-23, IL1β) to enhance T-cell proliferation, survival, and function ex vivo and in vivo. Genetic engineering of the isolated γδ T-cell may also comprise deleting or disrupting gene expression from one or more endogenous genes in the genome the isolated γδ T-cell, such as the MHC locus (loci).

Ex-Vivo Expansion of Engineered γδ T-Cells

In other aspects, the present disclosure provides methods for the ex vivo expansion of a population of engineered γδ T-cells for adoptive transfer therapy. An engineered γδ T-cell of the disclosure may be expanded ex vivo. An engineered γδ T-cell of the disclosure can be expanded in vitro without activation by APCs, or without co-culture with APCs and aminophosphates.

A method of the invention can expand various γδ T-cell(s) populations, such as a Vγ1$^+$, a Vγ2$^+$, Vγ3$^+$ γδ T-cell population. In some instances, a γδ T-cell population can be expanded in vitro in fewer than 36 days, fewer than 35 days, fewer than 34 days, fewer than 33 days, fewer than 32 days, fewer than 31 days, fewer than 30 days, fewer than 29 days, fewer than 28 days, fewer than 27 days, fewer than 26 days, fewer than 25 days, fewer than 24 days, fewer than 23 days, fewer than 22 days, fewer than 21 days, fewer than 20 days, fewer than 19 days, fewer than 18 days, fewer than 17 days, fewer than 16 days, fewer than 15 days, fewer than 14 days, fewer than 13 days, fewer than 12 days, fewer than 11 days, fewer than 10 days, fewer than 9 days, fewer than 8 days, fewer than 7 days, fewer than 6 days, fewer than 5 days, fewer than 4 days, fewer than 3 days.

In some aspects, provided are methods for expanding various γδ T-cells, including engineered and non-engineered γδ T-cells by contacting the γδ T-cells with an activation agent. In some cases, the activation agent binds to a specific epitope on a cell-surface receptor of a γδ T-cell. The activation agent can be an antibody, such as a monoclonal antibody. The activation agent can specifically activate the growth of one or more types of γδ T-cells, such δ1, δ2, or δ3 cell populations. In some embodiments the activation agent specifically activates the growth of δ1 cell populations. In other cases, the activation agent specifically activates the growth of δ2 cell populations.

An activation agent may stimulate the expansion of engineered and non-engineered γδ T-cells at a fast rate of growth. For instance, an agent that stimulates an expansion of the γδ T-cell population at a mean rate of 1 cell division in less than 30 hours, 1 cell division in less than 29 hours, 1 cell division in less than 28 hours, 1 cell division in less than 27 hours, 1 cell division in less than 26 hours, 1 cell division in less than 25 hours, 1 cell division in less than 24 hours, 1 cell division in less than 23 hours, 1 cell division in less than 22 hours, 1 cell division in less than 21 hours, 1 cell division in less than 20 hours, 1 cell division in less than 19 hours, 1 cell division in less than 18 hours, 1 cell division in less than 17 hours, 1 cell division in less than 16 hours, 1 cell division in less than 15 hours, 1 cell division in less than 14 hours, 1 cell division in less than 13 hours, 1 cell division in less than 12 hours, 1 cell division in less than 11 hours, 1 cell division in less than 10 hours, 1 cell division in less than 9 hours, 1 cell division in less than 8 hours, 1 cell division in less than 7 hours, 1 cell division in less than 6 hours, 1 cell division in less than 5 hours, 1 cell division in less than 4 hours, 1 cell division in less than 3 hours, 1 cell division in less than 2 hours.

In some cases, an activation agent may stimulate the expansion of engineered and non-engineered γδ T-cells at a mean rate of about 1 division per about 4 hours, a mean rate of about 1 division per about 5 hours, a mean rate of about 1 division per about 6 hours, a mean rate of about 1 division per about 7 hours, a mean rate of about 1 division per about 8 hours, a mean rate of about 1 division per about 9 hours, a mean rate of about 1 division per about 10 hours, a mean rate of about 1 division per about 11 hours, a mean rate of about 1 division per about 12 hours, a mean rate of about 1 division per about 13 hours, a mean rate of about 1 division per about 14 hours, a mean rate of about 1 division per about 15 hours, a mean rate of about 1 division per about 16 hours, a mean rate of about 1 division per about 17 hours, a mean rate of about 1 division per about 18 hours, a mean rate of about 1 division per about 19 hours, a mean rate of about 1 division per about 20 hours, a mean rate of about 1 division per about 21 hours, a rate of about 1 division per about 22 hours, a rate of about 1 division per about 23 hours, a mean rate of about 1 division per about 24 hours, a mean rate of about 1 division per about 25 hours, a mean rate of about 1 division per about 26 hours, a mean rate of about 1 division per about 27 hours, a rate of about 1 division per about 28 hours, a rate of about 1 division per about 29 hours, a mean rate of about 1 division per about 30 hours, a mean rate of about 1 division per about 31 hours, a mean rate of about 1 division per about 32 hours, a mean rate of about 1 division per about 33 hours, a rate of about 1 division per about 34 hours, a rate of about 1 division per about 35 hours, a mean rate of about 1 division per about 36 hours.

An activation agent may stimulate the expansion of sub-populations of engineered and non-engineered γδ T-cells at different rates of growth. For instance, an agent may stimulate the growth of a δ1 cell population at a faster rate such that over a period of time from 1 day to 90 days of culture resulting in greater than 10-fold, 100-fold, 200-fold, 300-fold, 400-fold, 500-fold, 600-fold, 700-fold, 800-fold, 900-fold, 1,000-fold, 10,000-fold, 100,000-fold or 1,000,000-fold expansion over another γδ T-cell population, such as a δ2 or δ3 population or another γδ sub-population. In other cases, the agent may stimulate the growth of a δ2 or δ3 population at faster rates such that over a period of time from 1 day to 90 days of culture resulting in greater than 10-fold, 100-fold, 200-fold, 300-fold, 400-fold, 500-fold, 600-fold, 700-fold, 800-fold, 900-fold, 1,000-fold, 10,000-fold, 100,000-fold or 1,000,000-fold expansion over δ1 T-cell population or another γδ T-cell sub-population. In other cases, the agent may stimulate the growth of a δ2 population at faster rates such that over a period of time from 1 day to 90 days of culture resulting in greater than 10-fold, 100-fold, 200-fold, 300-fold, 400-fold, 500-fold, 600-fold, 700-fold, 800-fold, 900-fold, 1,000-fold, 10,000-fold, 100, 000-fold or 1,000,000-fold expansion over δ1 T-cell population, δ3 T-cell population or another γδ T-cell sub-population.

In some aspects, the disclosure provides a γδ T-cell population, wherein the expansion of the γδ T-cell population is activated with an agent that stimulates an expansion of the γδ T-cell population at a rapid rate, such as a rate of about 1 cell division per 1 hours or faster. In some cases, the agent selectively stimulates the proliferation of either δ1, δ2, or δ3 T-cells. A γδ T-cell population can comprises an amount of non-engineered γδ T-cells and an amount of engineered γδ T-cells. In some cases, the γδ T-cell population comprises different percentages of δ1, δ2, and δ3 T-cells. An engineered or non-engineered γδ T-cell population can comprise, for example, fewer than 90% δ1 T-cells, fewer than 80% δ1 T-cells, fewer than 70% δ1 T-cells, fewer than 60% δ1 T-cells, fewer than 50% δ1 T-cells, fewer than 40% δ1 T-cells, fewer than 30% δ1 T-cells, fewer than 20% δ1 T-cells, fewer than 10% δ1 T-cells, or fewer than 5% δ1 T-cells. Alternatively, an engineered or non-engineered γδ T-cell population can comprise greater than 5% δ1 T-cells, greater than 10% δ1 T-cells, greater than 20% δ1 T-cells, greater than 30% δ1 T-cells, greater than 40% δ1 T-cells, greater than 50% δ1 T-cells, greater than 60% δ1 T-cells, greater than 70% δ1 T-cells, greater than 80% δ1 T-cells, or greater than 90% δ1 T-cells.

An engineered or non-engineered γδ T-cell population can comprise, for example, fewer than 90% δ2 T-cells, fewer than 80% δ2 T-cells, fewer than 70% δ2 T-cells, fewer than 60% δ2 T-cells, fewer than 50% δ2 T-cells, fewer than 40% δ2 T-cells, fewer than 30% δ2 T-cells, fewer than 20% δ2 T-cells, fewer than 10% δ2 T-cells, or fewer than 5% δ2 T-cells. Alternatively, an engineered or non-engineered γδ T-cell population can comprise greater than 5% δ2 T-cells, greater than 10% δ2 T-cells, greater than 20% δ2 T-cells, greater than 30% δ2 T-cells, greater than 40% δ2 T-cells, greater than 50% δ2 T-cells, greater than 60% δ2 T-cells, greater than 70% δ2 T-cells, greater than 80% δ2 T-cells, or greater than 90% δ2 T-cells.

An engineered or non-engineered γδ T-cell population can comprise, for example, fewer than 90% δ3 T-cells, fewer than 80% δ3 T-cells, fewer than 70% δ3 T-cells, fewer than 60% δ3 T-cells, fewer than 50% δ3 T-cells, fewer than 40% δ3 T-cells, fewer than 30% δ3 T-cells, fewer than 20% δ3 T-cells, fewer than 10% δ3 T-cells, or fewer than 5% δ3 T-cells. Alternatively, an engineered or non-engineered γδ T-cell population can comprise greater than 5% δ3 T-cells, greater than 10% δ3 T-cells, greater than 20% δ3 T-cells, greater than 30% δ3 T-cells, greater than 40% δ3 T-cells, greater than 50% δ3 T-cells, greater than 60% δ3 T-cells, greater than 70% δ3 T-cells, greater than 80% δ3 T-cells, or greater than 90% δ3 T-cells.

One or more activation agent can contact the γδ T-cells and thereafter a costimulatory molecule can contact the γδ T-cells to provide further stimulation and to expand the γδ T-cells. In some embodiments, the activation agent and/or costimulatory agent can be lectins of plant and non-plant origin, monoclonal antibodies that activate γδ T-cells, and other non-lectin/non-antibody agents. In other cases, the plant lectin can be concanavalin A (ConA) although other plant lectins such as phytohemagglutinin (PHA) may be used. Other examples of lectins include protein peanut agglutinin (PNA), soybean agglutinin (SBA), les culinaris agglutinin (LCA), *Pisum sativum* agglutinin (PSA), *Helix pomatia* agglutinin (HPA), *Vicia graminea* Lectin (VGA).

Non-limiting examples of activating agents and costimulatory molecules include antibodies such as 5A6.E9, B1, TS8.2, 15D, B6, B3, TS-1, γ3.20, 7A5, IMMU510, R9.12, 11F2, or a combination thereof. Other examples of activating agents and costimulatory molecules include zoledronate, phorbol 12-myristate-13-acetate (TPA), mezerein, staphylococcal enterotoxin A (SEA), streptococcal protein A, or a combination thereof.

In other cases, the activation agent and/or costimulatory agent can be, antibodies or ligands to α TCR, β TCR, γ TCR, δ TCR, CD277, CD28, CD46, CTLA4, ICOS, PD-1, CD30, NKG2D, NKG2A, HVEM, 4-1 BB (CD137), OX40 (CD134), CD70, CD80, CD86, DAP, CD122, GITR, FceRIg, CD1, CD16, CD161, DNAX, accessory molecule-1 (DNAM-1), SLAM, coxsackie virus and adenovirus receptor or a combination thereof.

Epitope Identification

In one aspect, the disclosure provides a method for identifying the epitope of an agent that stimulates the expansion of engineered and non-engineered γδ T-cells at a fast rate of growth. An epitope can include at least 3, 4, 5, 6, 7, 8, 9, 10, 11, 12, 13, 14, 15, 16, 17, 18, 19, or 20 amino acids in a unique spatial conformation. Epitopes can be formed both from contiguous amino acids or noncontiguous amino acids juxtaposed by tertiary folding of a protein. Epitopes formed from contiguous amino acids can be typically retained on exposure to denaturing solvents whereas epitopes formed by tertiary folding can be typically lost on treatment with denaturing solvents.

Epitope mapping can be performed to identify the linear or non-linear, discontinuous amino acid sequence(s), i.e. the epitope, that is recognized by an activating agent of interest, such as the, 5A6.E9, B1, TS8.2, 15D, B6, B3, TS-1, 3.20, IMMU510, R9.12, 11F2 and 7A5 antibodies. A general approach for epitope mapping can require the expression of the full-length polypeptide sequence that is recognized by an antibody or ligand of interest, as well as various fragments, i.e., truncated forms of the polypeptide sequence, generally in a heterologous expression system. These various recombinant polypeptide sequences or fragments thereof (e.g., fused with an N-terminal protein (e.g., GFP)) can then be used to determine if the antibody or ligand of interest is capable of binding to one or more of the truncated forms of the polypeptide sequence. Through the use of reiterative truncation and the generation of recombinant polypeptide sequences with overlapping amino acid regions, it is possible to identify the region of the polypeptide sequence that is recognized by the antibody of interest (see, e.g., Epitope Mapping Protocols in Methods in Molecular Biology, Vol. 66, Glenn E. Morris, Ed (1996)). The methods rely on the ability of an agent such as an antibody of interest to bind to sequences that have been recreated from epitope libraries, such as epitope libraries derived from, synthetic peptide arrays on membrane supports, combinatorial phage display peptide libraries. The epitope libraries then provide a range of possibilities that are screened against an antibody. Additionally, site specific mutagenesis, or random Ala scan, targeting one or more residues of an epitope can be pursued to confirm the identity of an epitope.

A library of epitopes can be created by synthetically designing various possible recombinations of a γδ T-cell receptor (γδ TCR) as cDNA constructs and expressing them in a suitable system. For instance, a plurality of Vδ1 gene segments differing in their Jδ region can be synthetically designed, including Jδ1, Jδ2 and Jδ3 gene segments. Alternatively, Vδ2Jδ1 and Vδ3Jδ1 chains can also ordered as synthetic genes and cloned into suitable vectors. A plurality of synthetically cloned δ TCR chains, such as Vδ1Jδ1, Vδ1Jδ2, Vδ1Jδ3, Vδ1Jδ4, Vδ2 and Vδ3, chains can be co-transfected into a host system with synthetically cloned γ TCR chains such as Vγ2, Vγ3, Vγ4, Vγ5, Vγ8, Vγ9 and Vγ10 synthetically designed gene segments. In other cases δ TCR chains, such as Vδ1Jδ1, Vδ1Jδ2, Vδ1Jδ3, Vδ1Jδ4, Vδ2 and Vδ3, chains can be amplified out of Total RNA extracted from human PBMCs or γδ T-cells isolated from human normal and malignant tissue.

The host system can be any suitable expression system such as 293 cells, insect cells, or a suitable in-vitro translation system. The plurality of various possible recombinations of synthetically designed γδ T-cell segments transfected into a host system can provide, for instance, more than 25, 30, 35, 40, 45, 50, 55, 60, 65, 70, 75, 80, 85, or 90 possible pairing combinations of γδ TCRs. The binding of an agent to one of the epitopes in the previously described library can be detected by contacting a labeled antibody, such as TS-1, 5A6.E9, B1, TS8.2, 15D, B6, B3, γ3.20, R9.12, 7A5, with an epitope of the library and detecting a signal from the label.

For epitope mapping, computational algorithms have also been developed which have been shown to map conformational discontinuous epitopes. Conformational epitopes can be identified by determining spatial conformation of amino acids with methods that include, e.g., x-ray crystallography and 2-dimensional nuclear magnetic resonance. Some epitope mapping methods, such as, x-ray analyses of crystals of antigen:antibody complexes can provide atomic resolution of the epitope. In other cases, computational combinatorial methods for epitope mapping can be employed to model a potential epitope based on the sequence of the antibody, such as TS-1 antibody or TS8.2 antibody. In such cases, the antigen binding portion of the antibody is sequenced, and computation models are used to reconstruct and predict a potential binding site of the antibody.

In some cases the disclosure provides a method of determining an epitope of a γδ T-cell receptor, comprising: (a) preparing a library of epitopes from the γδ T-cell receptor; (b) contacting the library of epitopes with an antibody; and (b) identifying the amino acid sequence of at least one epitope in the library of epitopes that is bound by the antibody. In some cases, the antibody is selected from the group consisting of, 5A6.E9, B1, TS8.2, 15D, B6, B3, TS-1, R9.12, 11F2 and 7A5 antibodies. In one instance, the antibody is attached to a solid support. The library of epitopes can comprise sequences that correspond to continuous and discontinuous epitopes of a T-cell receptor, such as a γ TCR or a δ TCR. In some cases, the library of epitopes comprises fragments from a γδ T-cell receptor ranging from about 10 amino acids to about 30 amino acids in length, from about 10 amino acids to about 20 amino acids in length, or from about 5 amino acids to about 12 amino acids in length. In some cases, the antibody is labeled and the label is a radioactive molecule, a luminescent molecule, a fluorescent molecule, an enzyme, or biotin.

Methods of Treatment

Pharmaceutical compositions containing an engineered γδ T-cell described herein may be administered for prophylactic and/or therapeutic treatments. In therapeutic applications, the compositions can be administered to a subject already suffering from a disease or condition in an amount sufficient to cure or at least partially arrest the symptoms of the disease or condition. An engineered γδ T-cell can also be administered to lessen a likelihood of developing, contracting, or worsening a condition. Effective amounts of a population of engineered γδ T-cells for therapeutic use can vary based on the severity and course of the disease or condition, previous therapy, the subject's health status, weight, and/or response to the drugs, and/or the judgment of the treating physician.

An engineered γδ T-cell of the disclosure can be used to treat a subject in need of treatment for a condition. Examples of conditions include cancer, infectious disease, autoimmune disorder and sepsis. Subjects can be humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. A subject can be of any age. Subjects can be, for example, elderly adults, adults, adolescents, pre-adolescents, children, toddlers, infants.

Figure 2:
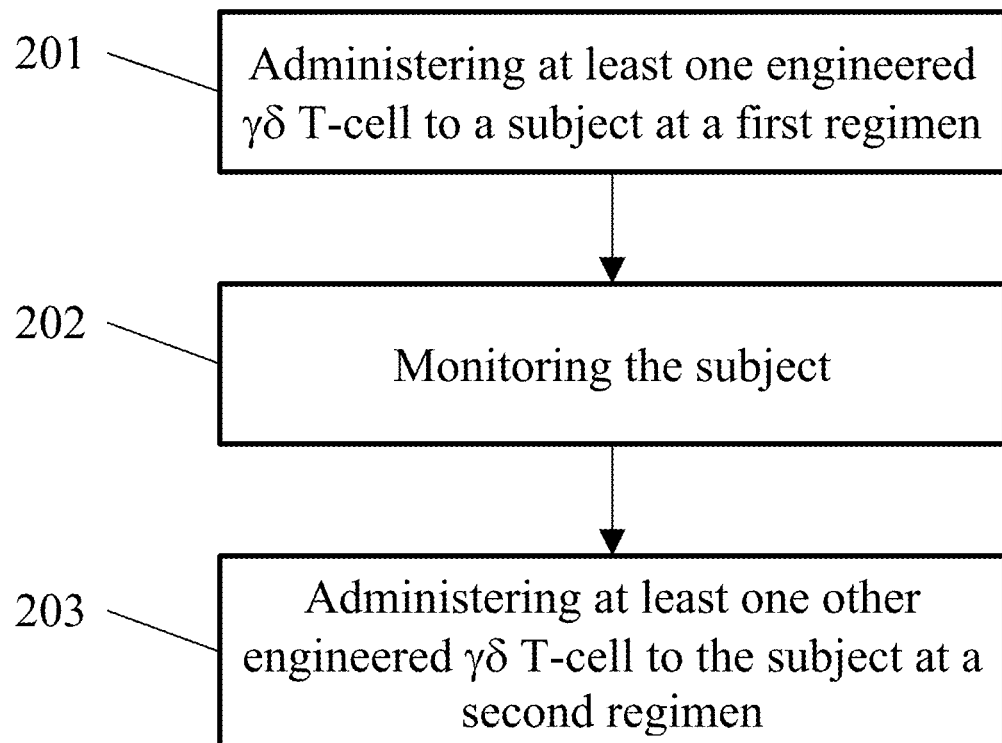
FIG. 2 schematically illustrates a method for treating a subject.

A method of treating a condition (e.g., ailment) in a subject with a γδ T-cell may comprise administering to the subject a therapeutically-effective amount of an engineered γδ T-cell. A γδ T-cell of the disclosure may be administered at various regimens (e.g., timing, concentration, dosage, spacing between treatment, and/or formulation). A subject can also be preconditioned with, for example, chemotherapy, radiation, or a combination of both, prior to receiving a an engineered γδ T-cell of the disclosure. As part of a treatment, an engineered γδ T-cell may be administered to a subject at a first regimen and the subject may be monitored to determine whether the treatment at the first regimen meets a given level of therapeutic efficacy. In some cases, the engineered γδ T-cell or another engineered γδ T-cell may be administered to the subject at a second regimen. FIG. 2 schematically illustrates a method for treating a subject. In a first operation 201, at least one engineered γδ T-cell is administered to a subject that has or is suspected of having a given condition (e.g., cancer). The engineered γδ T-cell may be administered at a first regimen. In a second operation 202, the subject may be monitored, for example by a healthcare provider (e.g., treating physician or nurse). In some examples, the subject is monitored to determine or gauge an efficacy of the engineered γδ T-cell in treating the condition of the subject. In some situations, the subject may also be monitored to determine the in vivo expansion of a γδ T-cell population in the subject. Next, in a third operation 203, at least one other engineered γδ T-cell is administered to the subject at a second regimen. The second regimen may be the same as the first regimen or different than the first regimen. In some situations, the third operation 203 is not performed, for example, if the administration of the engineered γδ T-cell in the first operation 201 is found to be effective (e.g., a single round of administration may be sufficient to treat the condition). Due to their allogeneic and universal donor characteristics, a population of engineered γδ T-cells may be administrated to various subjects, with different MHC haplotypes. An engineered γδ T-cell may be frozen or cryopreserved prior to being administered to a subject.

Figure 3:
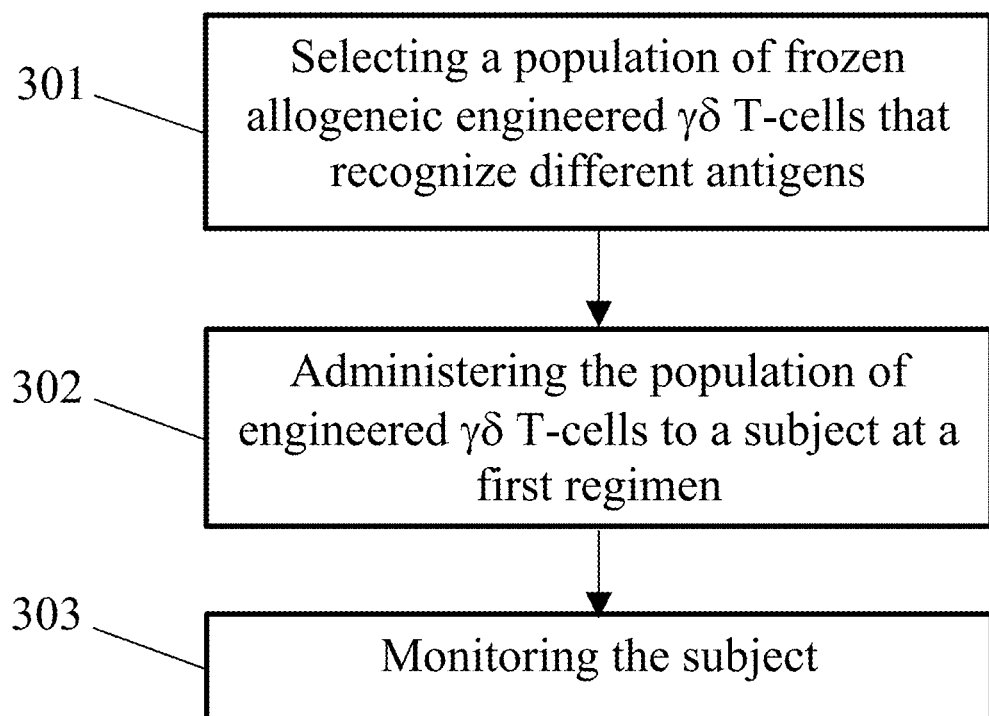
FIG. 3 schematically illustrates a method for administrating a population of engineered γδ T-cells to a subject.

A population of engineered γδ T-cells may also be frozen or cryopreserved prior to being administered to a subject. A population of engineered γδ T-cells can comprise two or more cells that express identical, different, or a combination of identical and different tumor recognition moieties. For instance, a population of engineered γδ T-cells can comprises several distinct engineered γδ T-cells that are designed to recognize different antigens, or different epitopes of the same antigen. For example, human cells afflicted with melanoma can express the NY-ESO-1 oncogene. Infected cells within the human can process the NY-ESO-1 oncoprotein into smaller fragments and present various portions of the NY-ESO-1 protein for antigen recognition. A population of engineered γδ T-cells can comprise various engineered γδ T-cells that express different tumor recognition moieties designed to recognize different portions of the NY-ESO-1 protein. FIG. 3 schematically illustrates a method for treating a subject with a population of engineered γδ T-cells that recognizes different epitopes of the melanoma antigen NY-ESO-1. In a first operation 301, a population of engineered γδ T-cells that recognize different epitopes of the same antigen is selected. For example, the population of engineered γδ T-cells may comprise two or more cells that expressing different tumor recognition moieties that recognize different portions of the NY-ESO-1 protein. In a second operation 302, The population of engineered γδ T-cells may be administered at a first regimen. In a second operation 303, the subject may be monitored, for example by a healthcare provider (e.g., treating physician or nurse).

A γδ T-cell of the disclosure may be used to treat various conditions. In some cases, an engineered γδ T-cell of the disclosure may be used to treat a cancer, including solid tumors and hematologic malignancies. Non-limiting examples of cancers include: acute lymphoblastic leukemia, acute myeloid leukemia, adrenocortical carcinoma, AIDS-related cancers, AIDS-related lymphoma, anal cancer, appendix cancer, astrocytomas, neuroblastoma, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenström macroglobulinemia, and Wilms tumor.

In some cases, an engineered γδ T-cell of the disclosure may be used to treat an infectious disease. An infectious disease may be caused, for example, by a pathogenic bacterium or by a virus. Various pathogenic proteins, nucleic acids, lipids, or fragments thereof can be expressed by a diseased cell. An antigen presenting cell can internalize such pathogenic molecules, for instance with phagocytosis or by receptor-mediated endocytosis, and display a fragment of the antigen bound to an appropriate MHC molecule. For instance, various 9 mer fragments of a pathogenic protein may be displayed by an APC. Engineered γδ T-cells of the disclosure may be designed to recognize various antigens and antigen fragments of a pathogenic bacterium or a virus. Non-limiting examples of pathogenic bacteria can be found in the: a) *Bordetella* genus, such as *Bordetella pertussis* species; b) *Borrelia* genus, such *Borrelia burgdorferi* species; c) *Brucelia* genus, such as *Brucella abortus, Brucella canis, Brucela meliterisis*, and/or *Brucella suis* species; d) *Campylobacter* genus, such as *Campylobacter jejuni* species; e) *Chlamydia* and *Chlamydophila* genuses, such as *Chlamydia pneumonia, Chlamydia trachomatis*, and/or *Chlamydophila psittaci* species; f) *Clostridium* genus, such as *Clostridium botulinum, Clostridium difficile, Clostridium perfringens, Clostridium tetani* species; g) *Corynebacterium* genus, such as *Corynebacterium diphtheria* species; h) *Enterococcus* genus, such as *Enterococcus faecalis*, and/or *Enterococcus faecium* species; i) *Escherichia* genus, such as *Escherichia coli* species; j) *Francisella* genus, such as *Francisella tularensis* species; k) *Haemophilus* genus, such as *Haemophilus influenza* species; l) *Helicobacter* genus, such as *Helicobacter pylori* species; m) *Legionella* genus, such as *Legionella pneumophila* species; n) *Leptospira* genus, such as *Leptospira interrogans* species; o) *Listeria* genus, such as *Listeria monocytogenes* species; p) *Mycobacterium* genus, such as *Mycobacterium leprae, Mycobacterium tuberculosis*, and/or *mycobacterium ulcerans* species; q) *Mycoplasma* genus, such as *Mycoplasma pneumonia* species; r) *Neisseria* genus, such as *Neisseria gonorrhoeae* and/or *Neisseria meningitidia* species; s) *Pseudomonas* genus, such as *Pseudomonas aeruginosa* species; t) *Rickettsia* genus, such as *Rickettsia rickettsii* species; u) *Salmonella* genus, such as *Salmonella typhi* and/or *Salmonella typhimurium* species; v) *Shigella* genus, such as *Shigella sonnei* species; w) *Staphylococcus* genus, such as *Staphylococcus aureus, Staphylococcus epidermidis*, and/or *Staphylococcus saprophyticus* species; x) *Streptpcoccus* genus, such as *Streptococcus agalactiae, Streptococcus pneumonia*, and/or *Streptococcus pyogenes* species; y) *Treponema* genus, such as *Treponema pallidum* species; z) *Vibrio* genus, such as *Vibrio cholera*; and/or aa) *Yersinia* genus, such as *Yersinia pestis* species.

In some cases, an engineered γδ T-cell of the disclosure may be used to treat an infectious disease, an infectious disease may be caused a virus. Non-limiting examples of viruses can be found in the following families of viruses and are illustrated with exemplary species: a) Adenoviridae family, such as Adenovirus species; b) Herpesviridae family, such as Herpes simplex type 1, Herpes simplex type 2, Varicella-zoster virus, Epstein-barr virus, Human cytomegalovirus, Human herpesvirus type 8 species; c) Papillomaviridae family, such as Human papillomavirus species; d) Polyomaviridae family, such as BK virus, JC virus species; e) Poxviridae family, such as Smallpox species; f) Hepadnaviridae family, such as Hepatitis B virus species; g) Parvoviridae family, such as Human bocavirus, Parvovirus B19 species; h) Astroviridae family, such as Human astrovirus species; i) Caliciviridae family, such as Norwalk virus species; j) Flaviviridae family, such as Hepatitis C virus (HCV), yellow fever virus, dengue virus, West Nile virus species; k) Togaviridae family, such as Rubella virus species; l) Hepeviridae family, such as Hepatitis E virus species; m) Retroviridae family, such as Human immunodeficiency virus (HIV) species; n) Orthomyxoviridaw family, such as Influenza virus species; o) Arenaviridae family, such as Guanarito virus, Junin virus, Lassa virus, Machupo virus, and/or Sabiá virus species; p) Bunyaviridae family, such as Crimean-Congo hemorrhagic fever virus species; q) Filoviridae family, such as Ebola virus and/or Marburg virus species; Paramyxoviridae family, such as Measles virus, Mumps virus, Parainfluenza virus, Respiratory syncytial virus, Human metapneumovirus, Hendra virus and/or Nipah virus species; r) Rhabdoviridae genus, such as Rabies virus species; s) Reoviridae family, such as Rotavirus, Orbivirus, Coltivirus and/or Banna virus species. In some examples, a virus is unassigned to a viral family, such as Hepatitis D.

In some cases, an engineered γδ T-cell of the disclosure may be used to treat an immune disease, such as an autoimmune disease. Inflammatory diseases, including autoimmune diseases are also a class of diseases associated with B-cell disorders. Examples of immune diseases or conditions, including autoimmune conditions, that can be treated with an engineered γδ T-cell disclosed herein include: rheumatoid arthritis, rheumatic fever, multiple sclerosis, experimental autoimmune encephalomyelitis, psoriasis, uveitis, diabetes mellitus, systemic lupus erythematosus (SLE), lupus nephritis, eczema, scleroderma, polymyositis/scleroderma, polymyositis/dermatomyositis, uncerative protitis, severe combined immunodeficiency (SCID), DiGeorge syndrome, ataxia-telangiectasia, seasonal allergies, perennial allergies, food allergies, anaphylaxis, mastocytosis, allergic rhinitis, atopic dermatitis, Parkinson's, Alzheimer's, hypersplenism, leukocyte adhesion deficiency, X-linked lymphoproliferative disease, X-linked agammaglobulinemia, selective immunoglobulin A deficiency, hyper IgM syndrome, HIV, autoimmune lymphoproliferative syndrome, Wiskott-Aldrich syndrome, chronic granulomatous disease, common variable immunodeficiency (CVID), hyperimmunoglobulin E syndrome, Hashimoto's thyroiditis, acute idiopathic thrombocytopenic purpura, chronic idiopathic thrombocytopenia purpura, dermatomyositis, Sydenham's chorea, myasthenia gravis, polyglandular syndromes, bullous pemphigoid, Henoch-Schonlein purpura, poststreptococcalnephritis, erythema nodosum, erythema multiforme, gA nephropathy, Takayasu's arteritis, Addison's disease, sarcoidosis, ulcerative colitis, polyarteritis nodosa, ankylosing spondylitis, Goodpasture's syndrome, thromboangitisubiterans, Sjogren's syndrome, primary biliary cirrhosis, Hashimoto's thyroiditis, thyrotoxicosis, chronic active hepatitis, polychondritis, pamphigus vulgaris, Wegener's granulomatosis, membranous nephropathy, amyotrophic lateral sclerosis, tabes dorsalis, giant cell arteritis/polymyalgia, peraiciousanemia, rapidly progressive glomerulonephritis, psoriasis, fibrosing alveolitis, and cancer.

Treatment with a γδ T-cell of the disclosure may be provided to the subject before, during, and after the clinical onset of the condition. Treatment may be provided to the subject after 1 day, 1 week, 6 months, 12 months, or 2 years after clinical onset of the disease. Treatment may be provided to the subject for more than 1 day, 1 week, 1 month, 6 months, 12 months, 2 years, 3 years, 4 years, 5 years, 6 years, 7 years, 8 years, 9 years, 10 years or more after clinical onset of disease. Treatment may be provided to the subject for less than 1 day, 1 week, 1 month, 6 months, 12 months, or 2 years after clinical onset of the disease. Treatment may also include treating a human in a clinical trial. A treatment can comprise administering to a subject a pharmaceutical composition comprising an engineered γδ T-cell of the disclosure.

In some cases, administration of an engineered γδ T-cell of the disclosure to a subject modulates the activity of endogenous lymphocytes in a subject's body. In some cases, administration of the engineered γδ T-cell(s) to a subject provides an antigen to an endogenous T-cell and may boost an immune response. In some cases, the memory T-cell is a $CD4^+$ T-cell. In some cases, the memory T-cell is a $CD8^+$ T-cell. In some cases, administration of the engineered γδ T-cell(s) to a subject activates the cytotoxicity of another immune cell. In some cases, the other immune cell is a CD8+ T-cell. In some cases, the other immune cell is a Natural Killer T-cell. In some cases, administration of the engineered γδ T-cell(s) to a subject suppress a regulatory T-cell. In some cases, the regulatory T-cell is a Fox3+ Treg cell. In some cases, the regulatory T-cell is a Fox3− Treg cell. Non-limiting examples of cells whose activity can be modulated by an engineered γδ T-cell of the disclosure include: hematopioietic stem cells; B cells; CD4; CD8; red blood cells; white blood cells; dendritic cells, including dendritic antigen presenting cells; leukocytes; macrophages; memory B cells; memory T-cells; monocytes; natural killer cells; neutrophil granulocytes; T-helper cells; and T-killer cells.

During most bone marrow transplants, a combination of cyclophosphamide with total body irradiation is conventionally employed to prevent rejection of the hematopietic stem cells (HSC) in the transplant by the subject's immune system. In some cases, incubation of donor bone marrow with interleukin-2 (IL-2) ex vivo is performed to enhance the generation of killer lymphocytes in the donor marrow. Interleukin-2 (IL-2) is a cytokine that is necessary for the growth, proliferation, and differentiation of wild-type lymphocytes. Current studies of the adoptive transfer of γδ T-cells into humans may require the co-administration of γδ T-cells and interleukin-2 However, both low- and high-dosages of IL-2 can have highly toxic side effects. IL-2 toxicity can manifest in multiple organs/systems, most significantly the heart, lungs, kidneys, and central nervous system. In some cases, the disclosure provides a method for administrating an engineered γδ T-cell to a subject without the co-administration of a cytokine, such as IL-2, IL-15, IL-12, IL-21. In some cases, an engineered γδ T-cell can be administered to a subject without co-administration with IL-2. In some cases, an engineered γδ T-cell is administered to a subject during a procedure, such as a bone marrow transplant without the co-administration of IL-2.

Methods of Administration

One or multiple engineered γδ T-cell(s) can be administered to a subject in any order or simultaneously. If simultaneously, the multiple engineered γδ T-cell(s) can be provided in a single, unified form, such as an intravenous injection, or in multiple forms, for example, as multiple intravenous infusions, s.c, injections or pills. The engineered γδ T-cell(s) can be packed together or separately, in a single package or in a plurality of packages. One or all of the engineered γδ T-cell(s) can be given in multiple doses. If not simultaneous, the timing between the multiple doses may vary to as much as about a week, a month, two months, three months, four months, five months, six months, or about a year. In some cases, an engineered γδ T-cell(s) can expand within a subject's body, in vivo, after administration to a subject. Engineered γδ T-cell(s) can be frozen to provide cells for multiple treatments with the same cell preparation. Engineered γδ T-cell(s) of the disclosure, and pharmaceutical compositions comprising the same, can be packaged as a kit. A kit may include instructions (e.g., written instructions) on the use of the engineered γδ T-cell(s) and compositions comprising the same.

In some cases, a method of treating a cancer comprises administering to a subject a therapeutically-effective amount of an engineered γδ T-cell(s), wherein the administration treats the cancer. In some embodiments the therapeutically-effective amount of the engineered γδ T-cell(s) is administered for at least about 10 seconds, 30 seconds, 1 minute, 10 minutes, 30 minutes, 1 hour, 2 hours, 3 hours, 4 hours, 5 hours, 6 hours, 12 hours, 24 hours, 2 days, 3 days, 4 days, 5 days, 6 days, 1 week, 2 weeks, 3 weeks, 1 month, 2 months, 3 months, 4 months, 5 months, 6 months, or 1 year. In some embodiments the therapeutically-effective amount of the engineered γδ T-cell(s) is administered for at least one week. In some embodiments the therapeutically-effective amount of the engineered γδ T-cell(s) is administered for at least two weeks.

An engineered γδ T-cell(s) described herein can be administered before, during, or after the occurrence of a disease or condition, and the timing of administering a pharmaceutical composition containing an engineered γδ T-cell can vary. For example, the engineered γδ T-cell can be used as a prophylactic and can be administered continuously to subjects with a propensity to conditions or diseases in order to lessen a likelihood of the occurrence of the disease or condition. The engineered γδ T-cell(s) can be administered to a subject during or as soon as possible after the onset of the symptoms. The administration of the engineered γδ T-cell(s) can be initiated immediately within the onset of symptoms, within the first 3 hours of the onset of the symptoms, within the first 6 hours of the onset of the symptoms, within the first 24 hours of the onset of the symptoms, within 48 hours of the onset of the symptoms, or within any period of time from the onset of symptoms. The initial administration can be via any route practical, such as by any route described herein using any formulation described herein. In some examples, the administration of an engineered γδ T-cell of the disclosure is an intravenous administration. One or multiple dosages of an engineered γδ T-cell can be administered as soon as is practicable after the onset of a cancer, an infectious disease, an immune disease, sepsis, or with a bone marrow transplant, and for a length of time necessary for the treatment of the immune disease, such as, for example, from about 24 hours to about 48 hours, from about 48 hours to about 1 week, from about 1 week to about 2 weeks, from about 2 weeks to about 1 month, from about 1 month to about 3 months. For the treatment of cancer, one or multiple dosages of an engineered γδ T-cell can be administered years after onset of the cancer and before or after other treatments. In some examples, an engineered γδ T-cell (s) can be administered for at least about 10 minutes, 30 minutes, 1 hour, 2 hours, 3 hours, 4 hours, 5 hours, 6 hours, 12 hours, 24 hours, at least 48 hours, at least 72 hours, at least 96 hours, at least 1 week, at least 2 weeks, at least 3 weeks, at least 4 weeks, at least 1 month, at least 2 months, at least 3 months, at least 4 months, at least 5 months, at least 6 months, at least 7 months, at least 8 months, at least 9 months, at least 10 months, at least 11 months, at least 12 months, at least 1 year, at least 2 years at least 3 years, at least 4 years, or at least 5 years. The length of treatment can vary for each subject.

Dosages

An engineered γδ T-cell(s) disclosed herein may be formulated in unit dosage forms suitable for single administration of precise dosages. In some cases, the unit dosage forms comprise additional lymphocytes. In unit dosage form, the formulation is divided into unit doses containing appropriate quantities of one or more compounds. The unit dosage can be in the form of a package containing discrete quantities of the formulation. Non-limiting examples are packaged tablets or capsules, and powders in vials or ampoules. Aqueous suspension compositions can be packaged in single-dose non-reclosable containers. Multiple-dose reclosable containers can be used, for example, in combination with a preservative or without a preservative. In some examples, the pharmaceutical composition does not comprise a preservative. Formulations for parenteral injection can be presented in unit dosage form, for example, in ampoules, or in multi-dose containers with a preservative.

An engineered γδ T-cell described herein may be present in a composition in an amount of at least 5 cells, at least 10 cells, at least 20 cells, at least 30 cells, at least 40 cells, at least 50 cells, at least 60 cells, at least 70 cells, at least 80 cells, at least 90 cells, at least 100 cells, at least 200 cells, at least 300 cells, at least 400 cells, at least 500 cells, at least 600 cells, at least 700 cells, at least 800 cells, at least 900 cells, at least $1\times10^3$ cells, at least $2\times10^3$ cells, at least $3\times10^3$ cells, at least $4\times10^3$ cells, at least $5\times10^3$ cells, at least $6\times10^3$ cells, at least $7\times10^3$ cells, at least $8\times10^3$ cells, at least $9\times10^3$ cells, at least $1\times10^4$ cells, at least $2\times10^4$ cells, at least $3\times10^4$ cells, at least $4\times10^4$ cells, at least $5\times10^4$ cells, at least $6\times10^4$ cells, at least $7\times10^4$ cells, at least $8\times10^4$ cells, at least $9\times10^4$ cells, at least $1\times10^5$ cells, at least $2\times10^5$ cells, at least $3\times10^5$ cells, at least $4\times10^5$ cells, at least $5\times10^5$ cells, at least $6\times10^5$ cells, at least $7\times10^5$ cells, at least $8\times10^5$ cells, at least $9\times10^5$ cells, at least $1\times10^6$ cells, at least $2\times10^6$ cells, at least $3\times10^6$ cells, at least $4\times10^6$ cells, at least $5\times10^6$ cells, at least $6\times10^6$ cells, at least $7\times10^6$ cells, at least $8\times10^6$ cells, at least $9\times10^6$ cells, at least $1\times10^7$ cells, at least $2\times10^7$ cells, at least $3\times10^7$ cells, at least $4\times10^7$ cells, at least $5\times10^7$ cells, at least $6\times10^7$ cells, at least $7\times10^7$ cells, at least $8\times10^7$ cells, at least $9\times10^7$ cells, at least $1\times10^8$ cells, at least $2\times10^8$ cells, at least $3\times10^8$ cells, at least $4\times10^8$ cells, at least $5\times10^8$ cells, at least $6\times10^8$ cells, at least $7\times10^8$ cells, at least $8\times10^8$ cells, at least $9\times10^8$ cells, at least $1\times10^9$ cells, or more.

The therapeutically effective dose of an engineered γδ T-cell of the invention can be from about 1 cell to about 10 cells, from about 1 cell to about 100 cells, from about 1 cell to about 10 cells, from about 1 cell to about 20 cells, from about 1 cell to about 30 cells, from about 1 cell to about 40 cells, from about 1 cell to about 50 cells, from about 1 cell to about 60 cells, from about 1 cell about 70 cells, from about 1 cell to about 80 cells, from about 1 cell to about 90 cells, from about 1 cell to about 100 cells, from about 1 cell to about $1\times10^3$ cells, from about 1 cell to about $2\times10^3$ cells, from about 1 cell to about $3\times10^3$ cells, from about 1 cell to about $4\times10^3$ cells, from about 1 cell to about $5\times10^3$ cells, from about 1 cell to about $6\times10^3$ cells, from about 1 cell to about $7\times10^3$ cells, from about 1 cell to about $8\times10^3$ cells, from about 1 cell to about $9\times10^3$ cells, from about 1 cell to about $1\times10^4$ cells, from about 1 cell to about $2\times10^4$ cells, from about 1 cell to about $3\times10^4$ cells, from about 1 cell to about $4\times10^4$ cells, from about 1 cell to about $5\times10^4$ cells, from about 1 cell to about $6\times10^4$ cells, from about 1 cell to about $7\times10^4$ cells, from about 1 cell to about $8\times10^4$ cells, from about 1 cell to about $9\times10^4$ cells, from about 1 cell to about $1\times10^5$ cells, from about 1 cell to about $2\times10^5$ cells, from about 1 cell to about $3\times10^5$ cells, from about 1 cell to about $4\times10^5$ cells, from about 1 cell to about $5\times10^5$ cells, from about 1 cell to about $6\times10^5$ cells, from about 1 cell to about $7\times10^5$ cells, from about 1 cell to about $8\times10^5$ cells, from about 1 cell to about $9\times10^5$ cells, from about 1 cell to about 1×10⁶ cells, from about 1 cell to about 2×10⁶ cells, from about 1 cell to about 3×10⁶ cells, from about 1 cell to about 4×10⁶ cells, from about 1 cell to about 5×10⁶ cells, from about 1 cell to about 6×10⁶ cells, from about 1 cell to about 7×10⁶ cells, from about 1 cell to about 8×10⁶ cells, from about 1 cell to about 9×10⁶ cells, from about 1 cell to about 1×10⁷ cells, from about 1 cell to about 2×10⁷ cells, from about 1 cell to about 3×10⁷ cells, from about 1 cell to about 4×10⁷ cells, from about 1 cell to about 5×10⁷ cells, from about 1 cell to about 6×10⁷ cells, from about 1 cell to about 7×10⁷ cells, from about 1 cell to about 8×10⁷ cells, from about 1 cell to about 9×10⁷ cells, from about 1 cell to about 1×10⁸ cells, from about 1 cell to about 2×10⁸ cells, from about 1 cell to about 3×10⁸ cells, from about 1 cell to about 4×10⁸ cells, from about 1 cell to about 5×10⁸ cells, from about 1 cell to about 6×10⁸ cells, from about 1 cell to about 7×10⁸ cells, from about 1 cell to about 8×10⁸ cells, from about 1 cell to about 9×10⁸ cells, or from about 1 cell to about 1×10⁹ cells.

In some cases, the therapeutically effective dose of an engineered γδ T-cell of the invention can be from about $1\times10^3$ cells to about 1 cell to about $2\times10^3$ cells, from about $1\times10^3$ cells to about $3\times10^3$ cells, from about $1\times10^3$ cells to about $4\times10^3$ cells, from about $1\times10^3$ cells to about $5\times10^3$ cells, from about $1\times10^3$ cells to about $6\times10^3$ cells, from about $1\times10^3$ cells to about $7\times10^3$ cells, from about $1\times10^3$ cells to about $8\times10^3$ cells, from about $1\times10^3$ cells to about $9\times10^3$ cells, from about $1\times10^3$ cells to about $1\times10^4$ cells, from about $1\times10^3$ cells to about $2\times10^4$ cells, from about $1\times10^3$ cells to about $3\times10^4$ cells, from about $1\times10^3$ cells to about $4\times10^4$ cells, from about $1\times10^3$ cells to about $5\times10^4$ cells, from about $1\times10^3$ cells to about $6\times10^4$ cells, from about $1\times10^3$ cells to about $7\times10^4$ cells, from about $1\times10^3$ cells to about $8\times10^4$ cells, from about $1\times10^3$ cells to about $9\times10^4$ cells, from about $1\times10^3$ cells to about $1\times10^5$ cells, from about $1\times10^3$ cells to about $2\times10^5$ cells, from about $1\times10^3$ cells to about $3\times10^5$ cells, from about $1\times10^3$ cells to about $4\times10^5$ cells, from about $1\times10^3$ cells to about $5\times10^5$ cells, from about $1\times10^3$ cells to about $6\times10^5$ cells, from about $1\times10^3$ cells to about $7\times10^5$ cells, from about $1\times10^3$ cells to about $8\times10^5$ cells, from about $1\times10^3$ cells to about $9\times10^5$ cells, from about $1\times10^3$ cells to about $1\times10^6$ cells, from about $1\times10^3$ cells to about $2\times10^6$ cells, from about $1\times10^3$ cells to about $3\times10^6$ cells, from about $1\times10^3$ cells to about $4\times10^6$ cells, from about $1\times10^3$ cells to about $5\times10^6$ cells, from about $1\times10^3$ cells to about $6\times10^6$ cells, from about $1\times10^3$ cells to about $7\times10^6$ cells, from about $1\times10^3$ cells to about $8\times10^6$ cells, from about $1\times10^3$ cells to about $9\times10^6$ cells, from about $1\times10^3$ cells to about $1\times10^7$ cells, from about $1\times10^3$ cells to about $2\times10^7$ cells, from about $1\times10^3$ cells to about $3\times10^7$ cells, from about $1\times10^3$ cells to about $4\times10^7$ cells, from about $1\times10^3$ cells to about $5\times10^7$ cells, from about $1\times10^3$ cells to about $6\times10^7$ cells, from about $1\times10^3$ cells to about $7\times10^7$ cells, from about $1\times10^3$ cells to about $8\times10^7$ cells, from about $1\times10^3$ cells to about $9\times10^7$ cells, from about $1\times10^3$ cells to about $1\times10^8$ cells, from about $1\times10^3$ cells to about $2\times10^8$ cells, from about $1\times10^3$ cells to about $3\times10^8$ cells, from about $1\times10^3$ cells to about $4\times10^8$ cells, from about $1\times10^3$ cells to about $5\times10^8$ cells, from about $1\times10^3$ cells to about $6\times10^8$ cells, from about $1\times10^3$ cells to about $7\times10^8$ cells, from about $1\times10^3$ cells to about $8\times10^8$ cells, from about $1\times10^3$ cells to about $9\times10^8$ cells, or from about $1\times10^3$ cells to about $1\times10^9$ cells.

Preservation

In some embodiments, γδ T-cells may be formulated in freezing media and placed in cryogenic storage units such as liquid nitrogen freezers (−195C) or ultra-low temperature freezers (−65C, −80C or −120C) for long-term storage of at least about 1 month, 2 months, 3 months, 4 months, 5 months, 6 months, 1 year, 2 years, 3 years, or at least 5 years. The freeze media can contain dimethyl sulfoxide (DMSO), and/or sodium chloride (NaCl), and/or dextrose, and/or dextran sulfate and/or hydroyethyl starch (HES) with physiological pH buffering agents to maintain pH between about 6.0 to about 6.5, about 6.5 to about 7.0, about 7.0 to about 7.5, about 7.5 to about 8.0 or about 6.5 to about 7.5. The cryopreserved γδ T-cells can be thawed and further processed by stimulation with antibodies, proteins, peptides, and/or cytokines as described herein. The cryopreserved γδ T-cells can be thawed and genetically modified with viral vectors (including retroviral and lentiviral vectors) or non-viral means (including RNA, DNA, and proteins) as described herein. The modified γδ T-cells can be further cryopreserved to generate cell banks in quantities of at least about 1, 5, 10, 100, 150, 200, 500 vials at about at least $10^1$, $10^2$, $10^3$, $10^4$, $10^5$, $10^6$, $10^7$, $10^8$, $10^9$, or at least about $10^{10}$ cells per mL in freeze media. The cryopreserved cell banks may retain their functionality and can be thawed and further stimulated and expanded. In some aspects, thawed cells can be stimulated and expanded in suitable closed vessels such as cell culture bags and/or bioreactors to generate quantities of cells as allogeneic cell product. Cryopreserved γδ T-cells can maintain their biological functions for at least about 6 months, 7 months, 8 months, 9 months, 10 months, 11 months, 12 months, 13 months, 15 months, 18 months, 20 months, 24 months, 30 months, 36 months, 40 months, 50 months, or at least about 60 months under cryogenic storage condition. In some aspects, no preservatives are used in the formulation. The cryopreserved γδ T-cells can be thawed and infused into multiple patients as allogeneic off-the-shelf cell product.

The present invention may be better understood by reference to the following examples, which are not intended to limit the scope of the claims.

EXAMPLES

Example 1

Primary Cell Isolation

Primary human peripheral blood mononuclear cells (PBMCs) are collected from healthy donors using an apheresis machine. The PBMCs are purified with the Ficolll-Paque™ PLUS (GE Healthcare Bio-Sciences AB, Uppsala, Sweden) system or similar systems. The cells are then re-suspended in an appropriate growth medium.

Alternatively, primary human cells are collected from peripheral blood, cord blood, bone marrow, healthy tissues, or tissues afflicted with a disease, such as cancerous tissues.

Example 2

Tissue from Healthy Donors

Fresh tissues from healthy donors are received from The Cooperative Human Tissue Network (CHTN) and are transported to the laboratory in RPMI-1640 media. Tissues are sliced into 1-3 mm³ fragments with a scalpel. 2-5 fragments/well placed in a 24-well plate (Costar) in 2 mL RPMI-1640 supplemented with GlutaMAX, 25 mM HEPES pH 7.2, 100 U/ml penicillin, 100 U/ml streptomycin and 10% Human AB Serum and 100 IU/ml of rhIL-2 or digested as described below. The plates are incubated in a humidified incubator at 37° C., with 5% $CO_2$ in air. Cultures are inspected every other day to monitor proliferation of lymphocytes. Half of the medium is replaced in all wells every 7 days after culture initiation. Lymphocytes are collected when a dense lymphocytic carpet covers the surrounding the fragments or lymphocyte population derived from digested tissues reached the proper concentration, as described below.

Example 3

Tissue Enzymatic Digestion

Fresh tissue samples from healthy donors were received from The Cooperative Human Tissue Network (CHTN) and were transported to the laboratory in RPMI-1640 media. Lymphocytes were isolated by enzymatic digestion using two enzyme blend Liberase™ DL Research Grade (Sigma Aldrich Co., St. Louis, Mo.), or Liberase™ Research Grade (Sigma Aldrich Co., St. Louis, Mo.). The tissues were cut into 2-3 mm3 fragments and digested for 1 hour at 370 C and 5% CO2. The digested cell suspension was passed through a 40-micron filter, spun down and washed with RPMI-1640 medium. Cells were counted and re-suspended in RPMI medium (GIBCO BRL), supplemented with 10% Human AB serum (Corning) and 100 IU/ml of rhIL-2. The collected cell population was seeded at 0.5 to 1×106 cells/ml in 24-well tissue culture plates. Cells were split into RPMI-IL2 containing medium when cells exceeded concentration of 1.5×106 cells/ml.

Example 4

Culture of Tumor Specimens

Fresh tumor specimens from patients with primary and metastatic cancers, including those of the colon, breast, ovary, kidney, head and neck, oral cavity, pancreas and liver, were received from The Cooperative Human Tissue Network (CHTN) and were transported to the laboratory in RPMI media. Tumor specimens were sliced into 1-3 $mm^3$ fragments with a scalpel. 2-5 fragments/well were placed in a 24-well plate (Costar) in 2 ml RPMI-1640 supplemented with GlutaMAX, 25 mM HEPES pH 7.2, 100 U/ml penicillin, 100 U/ml streptomycin and 10% Human AB serum and 100 IU/ml of rhIL-2 The plates were incubated in a humidified incubator at 37° C., with 5% $CO_2$ in air. Cultures were inspected every other day to monitor proliferation of lymphocytes. Half of the medium was replaced in all wells every 7 days after culture initiation. Lymphocytes were collected when a dense lymphocytic carpet covers the surrounding the fragments.

Example 5

Fresh Tumor Specimens Enzymatic Digestion

Fresh tumor specimens from patients with primary and metastatic cancers, including those of the colon, breast, ovary, kidney, head and neck, oral cavity, pancreas and liver, were received from The Cooperative Human Tissue Network (CHTN) and were transported to the laboratory in RPMI media. Lymphocytes were isolated by enzymatic digestion using two enzyme blend Liberase™ DL Research Grade (Sigma Aldrich Co., St. Louis, Mo.), or Liberase™ Research Grade (Sigma Aldrich Co., St. Louis, Mo.). The tissues were cut into 2-3 $mm^3$ fragments of and digested for 1 hour at 37° C. with 5% $CO_2$ in air. The digested cell suspension was passed through a 40-micron filter, spun down and washed with RPMI-1640 medium. Cells were counted and re-suspended in RPMI medium (GIBCO BRL), supplemented with 10% Human AB Serum (Corning) and 100 IU/ml of rhIL-2. The collected cell population was seeded at 0.5 to 1×$10^6$ cells/ml in 24-well tissue culture plates. Cells were split into RPMI-IL2 containing medium when cells exceeded concentration of 1.5×$10^6$ cells/ml.

Example 6

Culture of Primary Cells in Exemplary Serum Supplemented Media

PBMC populations were generated by separation from buffy coats derived from healthy donors, using Ficoll-Paque™ PLUS (GE Healthcare Bio-Sciences PA, USA). PBMCs were cultured at 1×$10^6$ cells/mL in 24-well tissue culture plate in RPMI-1640 (Corning CellGro) supplemented with 10% fetal Bovine serum (Gibco), 2 mmol/L L-glutamine, 100 U/mL penicillin, 100 U/mL streptomycin, and 100 rhIL-2/ml.

Similar culture conditions can be used to grow primary human cells collected from peripheral blood, cord blood, bone marrow, healthy tissues, or tissues afflicted with a disease, such as the cancerous tissues previously described.

Example 7

Culture of Primary Cells in Exemplary Serum-Free Media

PBMC populations were generated by separation from buffy coats derived from healthy donors, using Ficoll-Paque™ PLUS (GE Healthcare Bio-Sciences PA, USA). PBMCs were cultured at 1×$10^6$ cells/mL in 24-well tissue culture plate in CTS serum-free media with CTS-OpTmizer supplement.

Similar culture conditions can be used to grow primary human cells collected from peripheral blood, cord blood, bone marrow, healthy tissues, or tissues afflicted with a disease, such as the cancerous tissues previously described.

Example 8

Depletion of Adherent Monocytes and Macrophages

PMBCs are collected with apheresis methods as previously described and red blood cells are removed by hypotonic treatment or density separation using Ficoll gradient centrifugation. The red blood cell-free PBMCs are incubated in large-scale tissue culture vessels such as 10-stack or 40-stack Cell Factory (Nunc), roller bottles (Nunc). Adherent populations, comprising macrophages and monocytes, typically remain bound to the surface of the cell culture vessels. The cell population grown in suspension population is enriched in γδ T-cells. Approximately $10^8$, $10^9$ or $10^{10}$ PBMC are incubated with CD4 and CD8 coated iron-containing microbeads (e.g. Miltenyi Biotech Microbeads). The incubated cell population flows pass a magnetic field in which the $CD4^+$ and $CD8^+$ T-cells are retained. The "flow-through" cell population is enriched for γδ T-Cells.

Example 9

Depletion of Monocytes and Macrophages

PMBCs are collected with apheresis methods as previously described and red blood cells are removed by hypotonic treatment or density separation using Ficoll gradient centrifugation. The red blood cell-free PBMCs are incubated in large-scale tissue culture vessels such as 10-stack or 40-stack Cell Factory (Nunc), roller bottles (Nunc). Monocytes and macrophages are removed by flowing the red blood cell-removed PBMC over a packed glass wool column. The "flow-through" cell population is enriched in γδ T-cells for further processing.

Example 10

Enrichment of γδ T-Cells

PMBCs are collected with apheresis methods as previously described and red blood cells are removed by hypotonic treatment or density separation using Ficoll gradient centrifugation. The red blood cell-free PBMCs are incubated in large-scale tissue culture vessels such as 10-stack or 40-stack Cell Factory (Nunc), roller bottles (Nunc). Monocytes and macrophages are depleted either with the methods described in Example 8 or in Example 9. Approximately $10^8$, $10^9$ or $10^{10}$ PBMC are incubated with CD4 and CD8 coated iron-containing microbeads (e.g. Miltenyi Biotech Microbeads). The incubated cell population flows pass a magnetic field in which the $CD4^+$ and $CD8^+$ T-cells are retained. The "flow-through" cell population is enriched for γδ T-cells. Undesired cells, such as NK, γδ T-cells, B cells, monocytes and macrophages are removed by immunomagnetic beads separation (e.g. Miltenyi Biotech AutoMACS system) using a cocktail of antibodies directed against the undesired cell types.

Alternatively, undesired cell types are removed by using tetrameric antibody complex or bi-specific antibody directed against surface receptors on NK, ab T cells, B cells, monocytes and macrophages.

Example 11

Isolation of γδ T-Cells from Primary Cells with Antibodies

In one example, native γδ T-cells are isolated from primary cultures with flow cytometry sorting, based on the positive (i.e. γδ TCR) or negative (i.e. αβ TCR, CD4, CD8, CD56), expression of cell surface markers.

Example 12

Isolation of γδ T-Cells from Primary Tumors

Freshly harvested tumor specimens were obtained from NCI Cooperative Human Tissue Network (CHTN). Colon adenocarcinoma metastasis to liver (TIL 1) and renal tumor (TIL 2) were shipped in RPMI-1640 media. The tumor tissues were minced into small pieces of 2 mm³ in size using a flat blade followed by digestion with 2 mL Liberase enzyme cocktail (Sigma Chemical Co., St. Louis, Mo.) in RPMI and 3000 units of DNase as described. After digestion tumors were filtered through sterile gauze 40-micron nylon mesh, and washed twice in RPMI-1640. Cells were counted and plated in 24 well plate at 1×106/ml in RPMI-1640 containing 10% human AB serum supplemented with L-glutamine, and 100 U/mL of rhIL-2. Tumor infiltrating lymphocytes were collected after 6 days in culture. The presence of γδ T lymphocytes was analyzed by flow cytometry anti-δ1 TCR (FITC conjugated anti Vδ1TS8.2, (Thermo Fisher) and anti-Vδ2 B6 (Biolegend). Data was analyzed with FlowJo software.

FIG. 4 depicts a graph illustrating growth of γδ1 and γδ2 lymphocytes isolated from colon adenocarcinoma metastasis to liver (TIL 1) and renal tumors (TIL 2). These lymphocytes have been shown to express CCR4 and CCR7. As illustrated by FIG. 4, the Vδ1 subset was the predominant population isolated from both types of tumors.

Example 13

Stimulation and Expansion of γδ T-Cells

γδ T-Cells are stimulated and expanded in serum-free media such as Ex-Vivo 10, Ex-Vivo 15, Ex-Vivo 20, AIMV media, Optimizer CTS, containing cytokines (IL-2, IL-4, IL-7, IL-15, IL-12, IL-21, IL-23 or IL-33), growth factors (insulin and transferrin, insulin-like growth factors), albumin, lipids (cholesterol, lipid solutions, lipid pre-cursors), vitamins, copper, iron, selenium, protein hydrolysate, essential amino acids, non-essential amino acids, and shear protectant (Pluronic F-68).

The serum-free media described in this examples can be supplemented with additives to support high cell density γδ T-cell growth between $10^5$ to $2 \times 10^7$ cells/mL in suspension culture (e.g. WAVE bioreactor) while maintaining biological functionality of the γδ T-cell.

Example 14

Additives that Provide Robust γδ T-Cell Growth in Serum-Free Media

Additional additives that provided robust γδ T-cell growth included Calcium Chloride, Anhydrous, Calcium Nitrate, Cupric Sulfate, Pentahydrate, Ferric Citrate, Ferric Nitrate, Ferrous Sulfate, Zinc Sulfate, and/or Putrescine.

Trace metals were provided in the serum free media to provide low level of elemental components to replace serum, including Ammonium Paramolybdate, Vanadium, Manganes, Nickel, Sodium Selenite, Sodium Metasilicate, Nonahydrate, Stannous Chloride, Aluminum Chloride, Barium Acetate, Cadmium Chloride, Chromic Chloride, Cobalt, Germanium Dioxide, Potassium Bromide, Potassium Iodide, Rubidium Chloride, Silver Nitrate, Sodium Fluoride, and/or Zirconyl Chloride.

Other components added to cell culture media that support robust growth of γδ T-cells are Adenosine, Guanosine, Cytidine, Uridine, Betaine, Taurine, Folinic acid, Ethanolamine, Linoleic Acid, Oleic Acid Hydrocortisone, pyruvate, plant hydrolysates, yeast hydrolysates, and/or beta-mercaptoethanol.

Vitamins added to promote robust γδ T cell growth include: Biotin (B7), D-Calcium Pantothenate (B5), Choline Chloride, Cyanocobalamin (B12), Folic Acid (B9), i-Inositol (myo-Inositol), Niacinamide (B3), Pyridoxal, Monohydrochloride, Pyridoxine, Monohydrochloride (B6), Riboflavin (B2), Thiamine, and/or Monohydrochloride (B1).

Example 15

Characterization of Expanded γδ T-Cells: Immunophenotype

Expanded T-cell populations are characterized by FACS staining for cell surface markers that distinguish between the different populations. The cells were washed once in HEPES buffered saline solution (HBSS) containing 2% fetal bovine serum, incubated with appropriate amounts of MAbs at 4° C. for 30 minutes and rewashed in HBSS. Briefly, 1×10⁶ cells are stained in 100 ul volume of FACS staining medium (FSM; HBSS containing 2% fetal bovine serum) containing fluoroisothiocyanate (FITC) or phycoerythrin (PE) conjugated MAbs directed against CD2, CD3 (BioLegend, clone OKT3), CD4 (BioLegend clone OKT4), CD7, CD8 (BioLegend, clone RPAT8), CD11a, CD16, CD18, CD19, CD27, CD28, CD38, CD45RA, CD56, CD57, CD69, CD71, CD95, CD107, ICAM-1, MICA/B, NKG2D DR5, CCR1, CCR2, CCR3, CCR4, CCR5 CCR6, CCR7, CCR10, CXCR1, CXCR2, CXCR3, CXCR5, CXCR5, CXCR6, CXCR7, IL-2R, IL-7R, Ki67, L-selectin, VLA-4, JAML, PD1, PDL1, CTLA-4, Ox40, TCR Vδ1 (ThermoFisher Scientific, clone TS8.2), or TCR Vδ2 (BioLegend, clone B6).

In addition to surface markers, cytokine secretion, intracellular cytokines and/or membrane associated cytokines are characterized including TNF-α, IFN-γ, GM-CSF, IL-1, IL-2, IL-4, IL-6, IL-7, IL-10, IL-17, or IL-21.

Live cells were determined by absence or low incorporation of zombie violet (BioLegend) amine dye. Fluorescence Minus One (FMO) controls are used to define positive and negative gate boundaries of the surface expression of each antigen. Stained cells are collected on a Sony SH800 cytometer and data analyzed using FlowJo v10.1. Flow cytometry data are visualized as dot plots.

Example 16

δ2 T-Cell Expansion in Serum-Containing and Serum-Free Media

Figure 5:
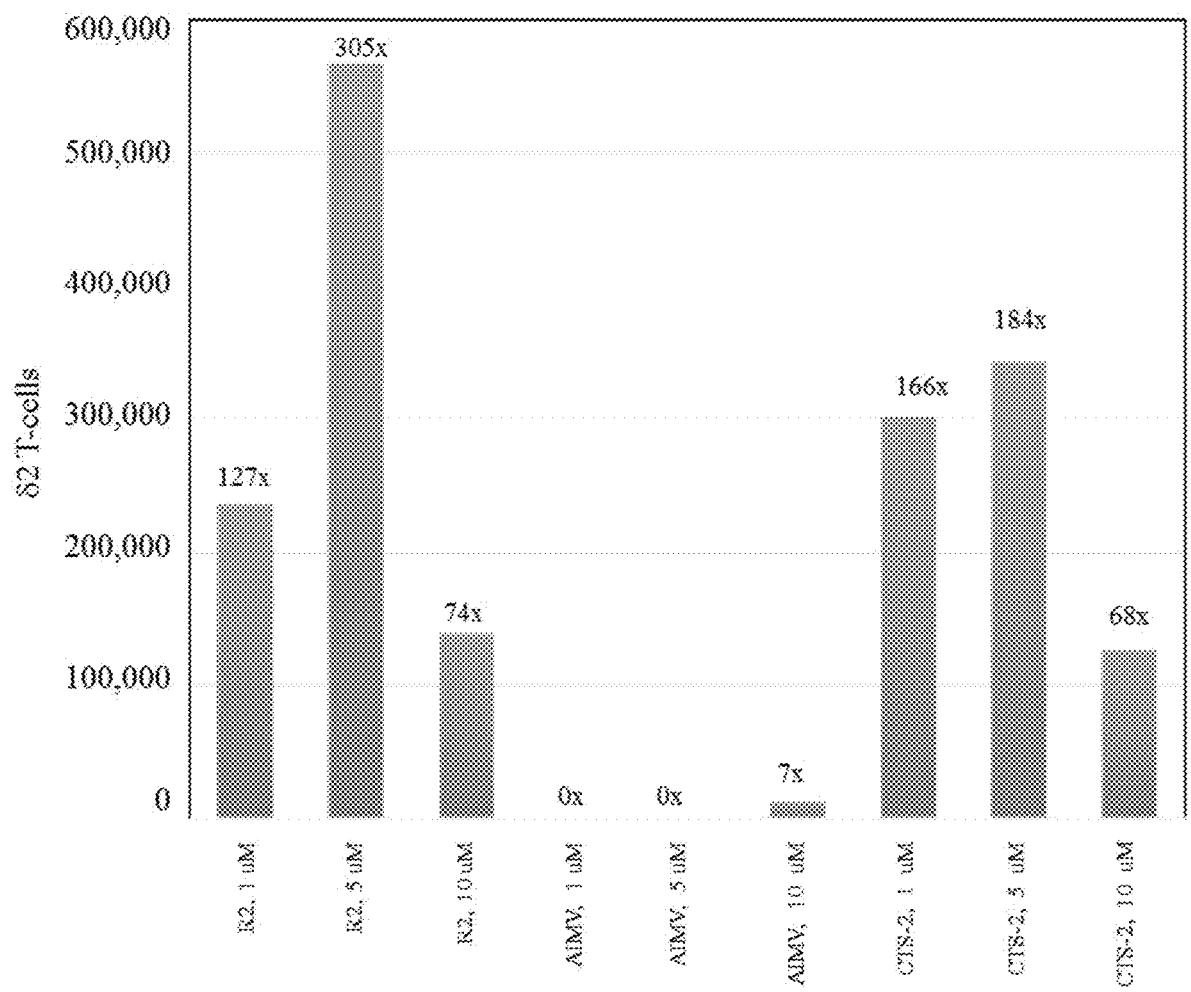
FIG. 5 depicts a graph illustrating γδ T-cells growth in serum-containing and serum-free media.

The growth and rate of expansion of different δ2 T-cells was evaluated in serum-containing media (R2:RPMI+10% FBS), and serum-free media (AIMV+bovine albumin; CTS serum-free Supplement). FIG. 5 depicts a graph illustrating the growth of δ2 T-cells. All media used in the current experiment contained 100 IU/mL IL-2, 2 mM glutamine and 1× penicillin/streptomycin. In addition, cells were stimulated with Zoledronic acid at 1, 5, and 20 μM on day 0. Media was replenished every 2-3 days without further addition of Zoledronic acid. The total number δ2 T-cells expanded from 10⁶ PBMC and the fold expansion of each treatment after a time period of 13 days are shown in FIG. 5.

Example 17

Anti-γδ TCR Antibody Blocking and Competing Assays

Figure 6:
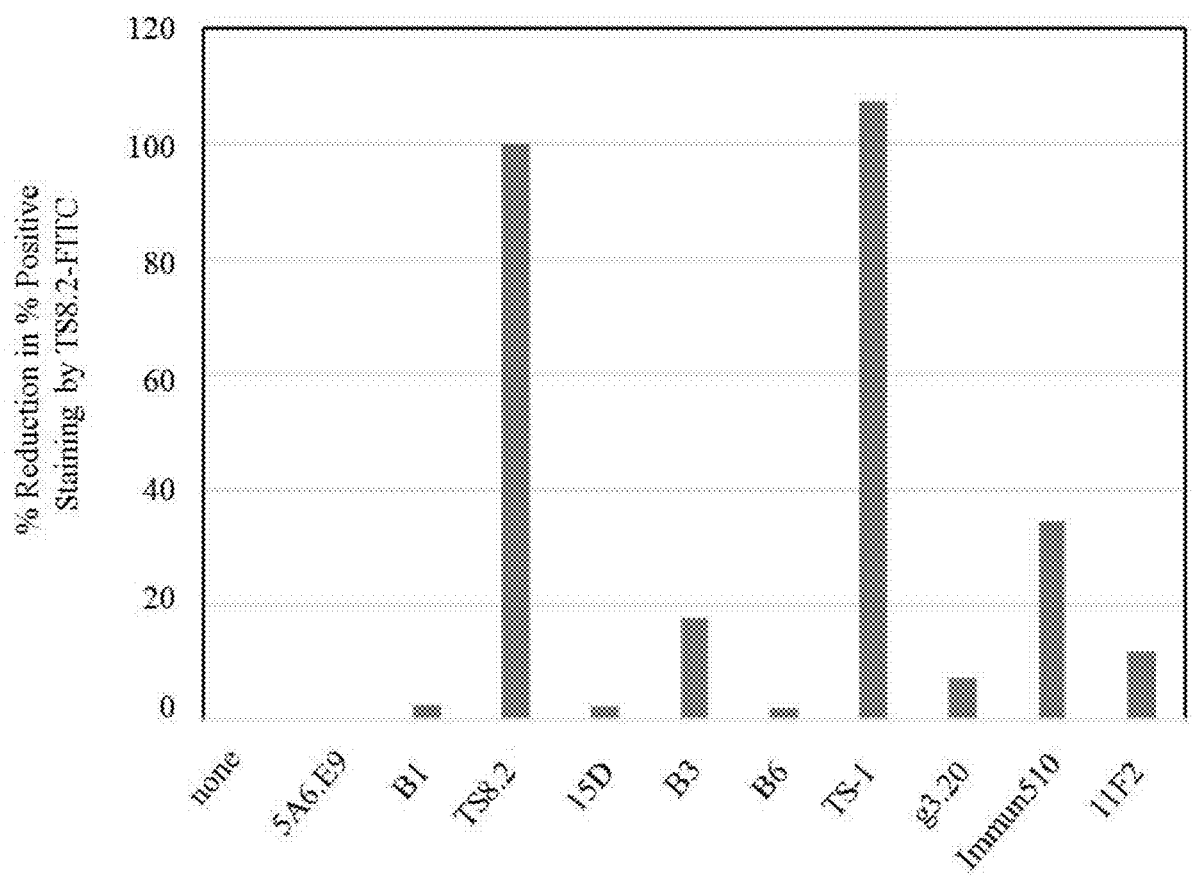
FIG. 6 depicts a graph illustrating anti-γδ TCR antibody blocking experiments with 5A6.E9, B1, TS8.2, 15D, B3, B6, TS-1, γ3.20, IMMU510, or 11F2.
Figure 7:
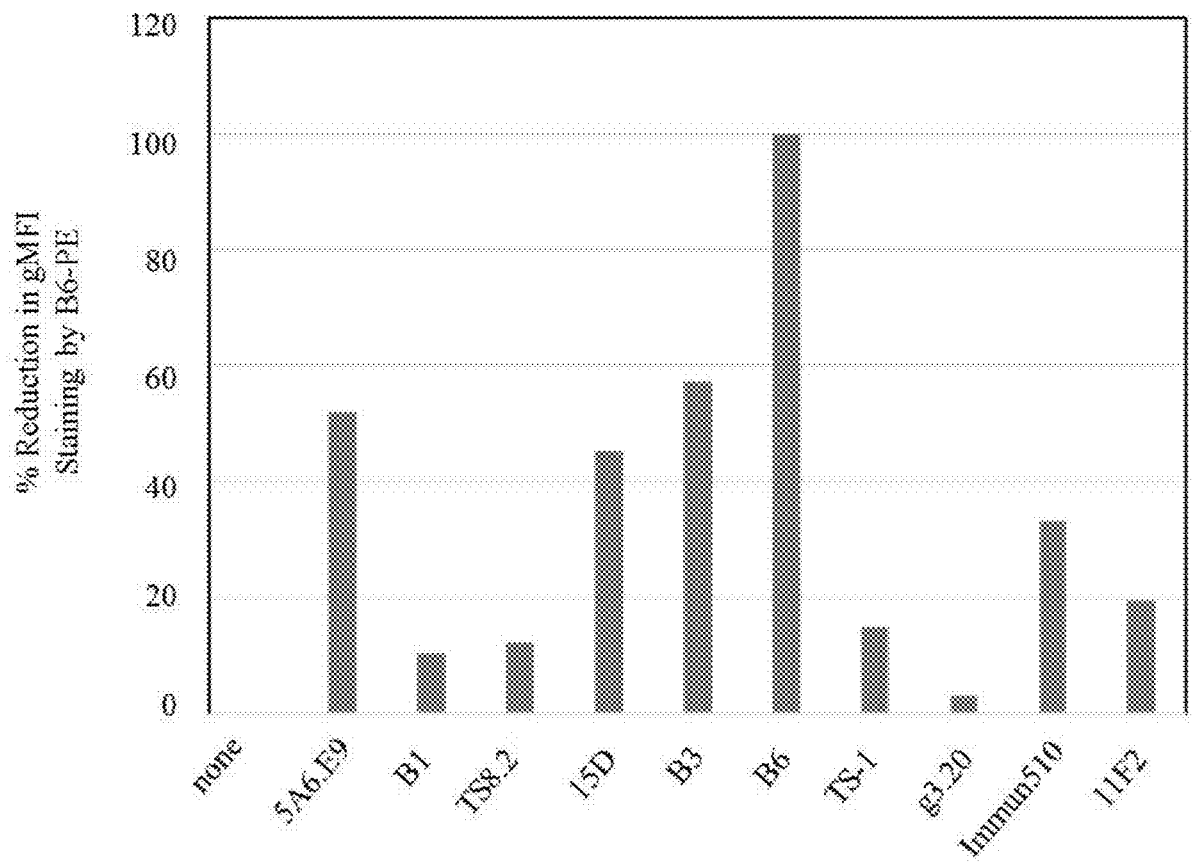
FIG. 7 depicts a graph illustrating anti-γδ TCR antibody blocking experiments with 5A6.E9, B1, TS8.2, 15D, B3, B6, TS-1, γ3.20, IMMU510, or 11F2.
Figure 8:
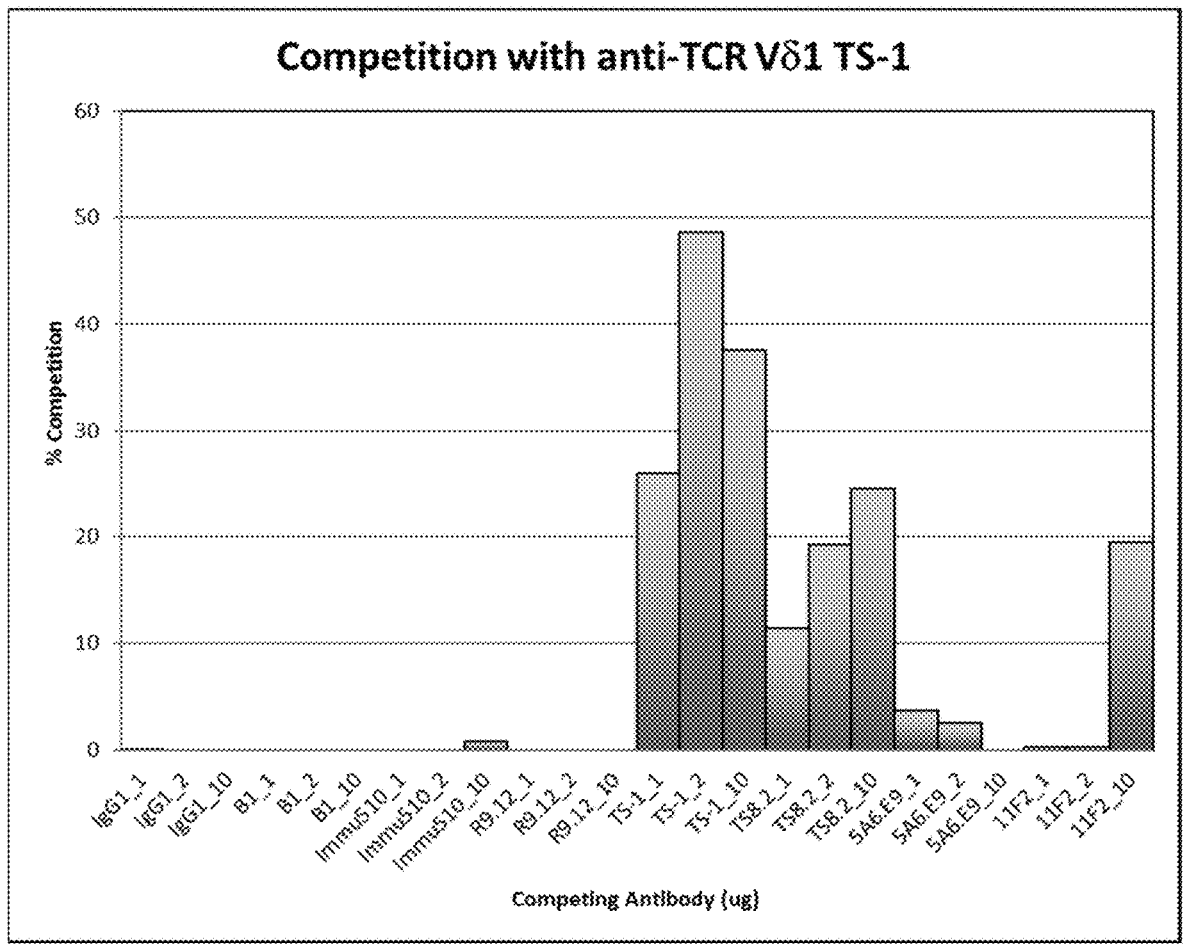
FIG. 8 depicts a competition experiment with anti-TCR Vδ1 TS-1 antibody
Figure 9:
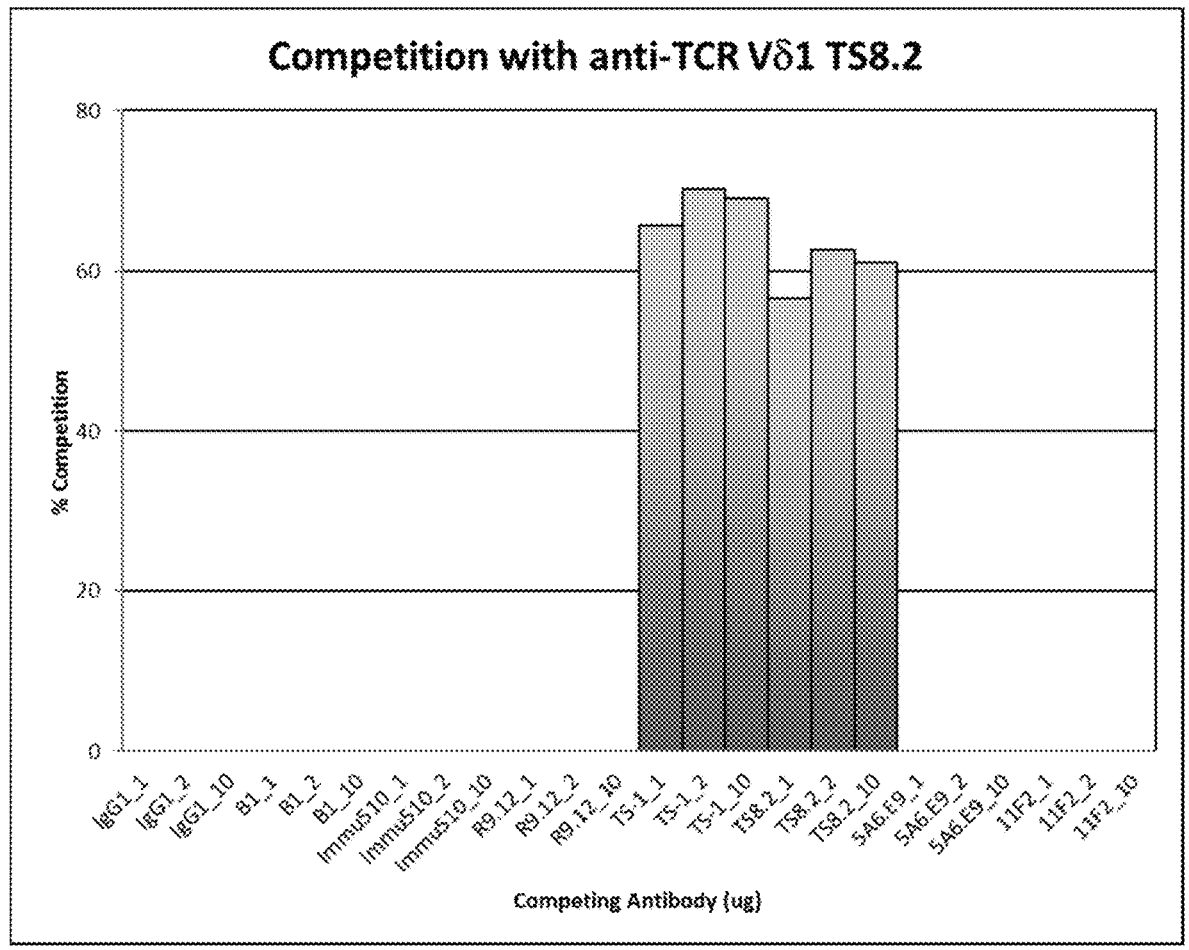
FIG. 9 depicts a competition experiment with anti-TCR Vδ1 TS8-2 antibody

FIG. 6 and FIG. 7 depict graphs illustrating anti-γδ TCR antibody blocking experiments and FIG. 8 and FIG. 9 depict antibody competition assays. FIG. 6 and FIG. 7 illustrate the results of blocking experiments were PBMCs were pre-incubated with various antibodies, namely, 5A6.E9, B1, TS8.2, 15D, B3, B6, TS-1, γ3.20, IMMU510, or 11F2. The cells were subsequently washed and stained with the secondary TS8.2-FITC (δ1-specific) or B6-PE (δ2-specific) antibodies. PBMCs samples were analyzed by flow cytornetry. Reduction in geometric mean fluoresce intensity (gMFI) was used to assess degree of blocking. The level of inhibition is illustrated against TS8.2-FITC (FIG. 6) and against B6-PE (FIG. 7).

Competition studies between MAbs TS-1 and TS8.2 and antibodies 5A6.E9, B1, IMMU510, R9.12-2, or 11F2 for binding on γδ1TCR-expressing cell line BE13 were performed by incubating 1×10⁵ cells with 1, 2 or 10 μg of unlabeled competing antibodies (IgG1, 5A6.E9, B1, TS8.2, TS-1, R9.12, IMMU510, or 11F2) and 0.2 μg of FITC conjugated anti-Vδ1 TCR clone TS8.2 (FIG. 8) or anti-Vδ1 TCR clone TS-1 (FIG. 9) simultaneously on ice for 30 minutes. % Competition is calculated by change in geometric mean fluorescence divided by the maximum change in geometric mean fluorescence. As depicted in FIG. 9, TS-1 antibody competed with TS8.2 binding to the cells as effectively as the TS8.2 antibody itself. None of the other antibodies were able to compete with TS8.2 binding. TS8.2 antibody competed with TS-1 binding to the cells but not as effectively as the TS-1 itself. Some level of competition with TS-1 binding was also observed with 11F2 antibody. These results indicate that TS-1 and TS8.2 antibodies bind both to γδ1 but likely not at the same epitope.

Example 18

Enzymatic Digestion of Tumor Specimens and γδ T-Cell Expansion with Antibodies to Specific γδ Epitopes 24 well plates were coated with 0.5-1 μg anti-γδ TCR antibodies. Cells isolated from digested tumor tissues as described in example 10 were counted and seeded on antibody coated wells at 0.5-1×10⁶ cell/ml 1 in RPMI 1640 medium supplemented with 10% human AB serum and rhIL-2 (100 IU/mL). The cultures were incubated at 37° C., 5% $CO_2$ for 74-21 days.

Example 19

Enzymatic Digestion of Tumor Specimens and γδ T-Cell Expansion with Antibodies to Specific γδ Epitopes Cells isolated from digested tumor tissues as described in example 5 were counted and seeded on antibody coated wells of a 3D cell culture plate (Corning® Costar® Ultra-Low attachment multi well plates) at 0.5-1×10⁶ cell/ml in RPMI 1640 medium supplemented with 10% human AB serum and rhIL-2 (100 IU/mL). The cultures were incubated at 37° C., 5% $CO_2$ for 74-21 days.

Example 20

Activation and Expansion of γδ T-Cells from PBMC

Activating agents were tested either as soluble agents, or agents immobilized on the culture wells. Soluble antigens and antibodies were added at a final concentration of 0.1-5 μg/ml to human PBMCs cultured in 24 well plate at a cell density of 1×10⁶ cell/ml. Alternatively, the same anti γδ TCR antibodies were immobilized by coating wells of 24-well culture plates. Anti γδ TCR antibodies were added at 0.1-10 μg/ml concentration. Wells were washed twice with PBS, then PBMCs were transferred to the plates and cultured in either RPMI-1640, AIM-V or CTS-OpTmizer media as described above. Cultured media was supplemented with 100 IU/mL of rhIL-2.

Example 21

Activation and Expansion of γδ T-Cells from PBMC

Figure 10:
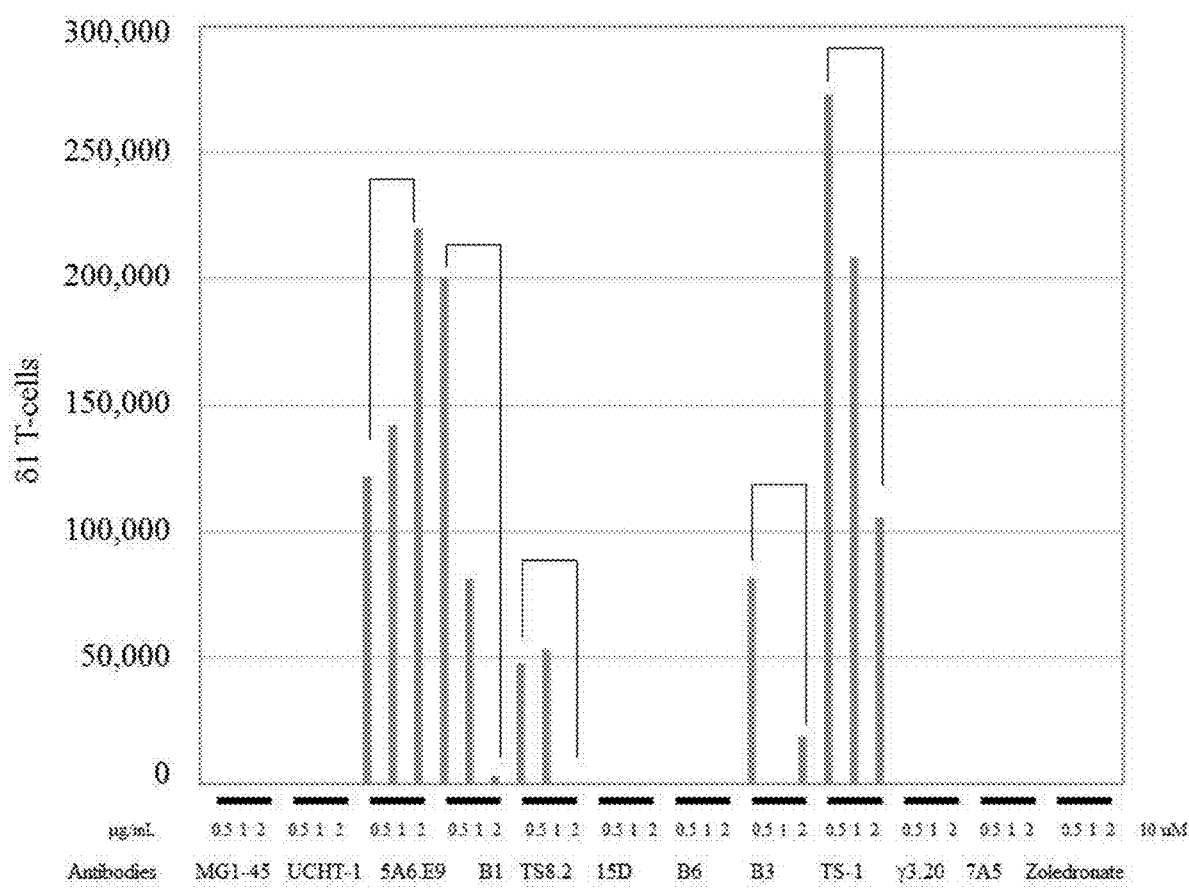
FIG. 10 depicts a graph illustrating activation and expansion of δ1 T-cells from PBMC.
Figure 11:
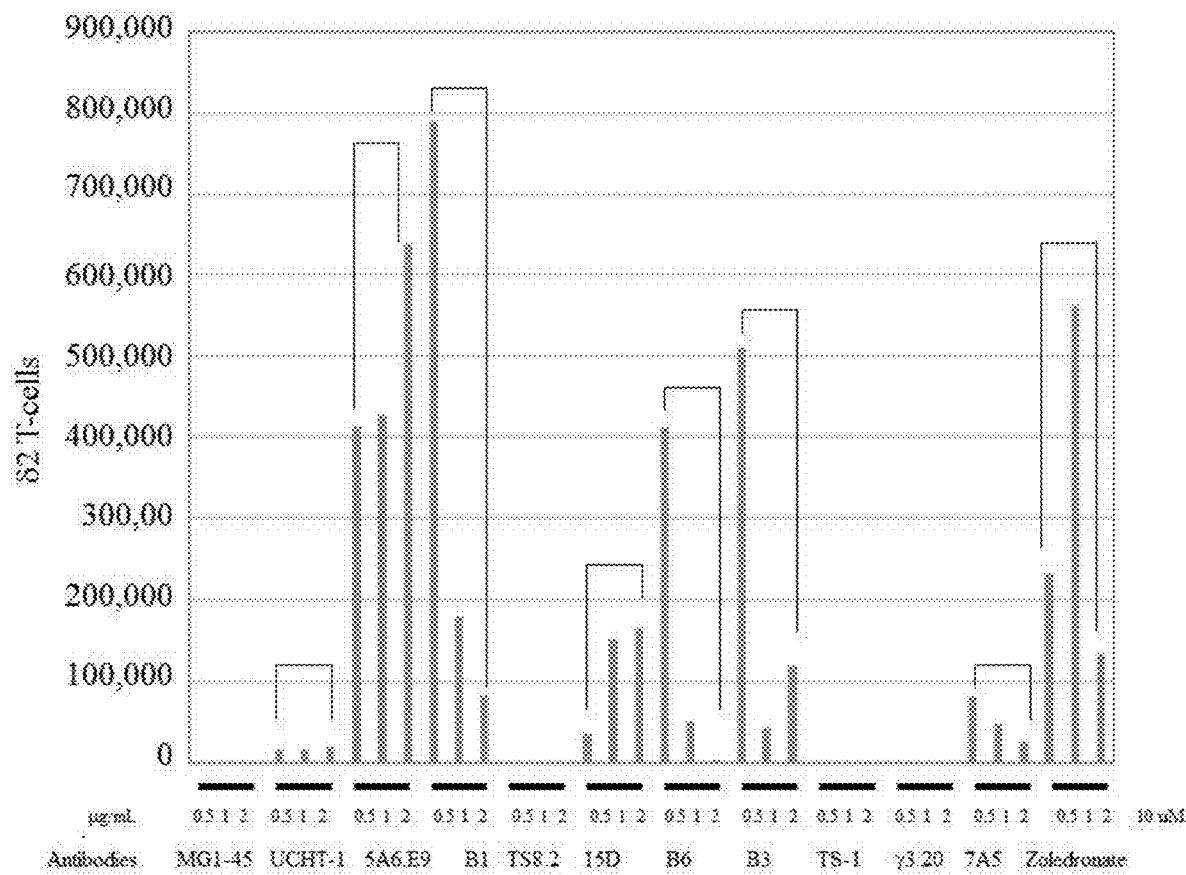
FIG. 11 depicts a graph illustrating activation and expansion of δ2 T-cells from PBMC.

One million PBMCs/ml from donor B3 were stimulated on Day-0 with various antibodies immobilized at 0.5, 1, and 2 μg per well in 24-well plates. The antibodies tested were Mouse IgG1 Isotype control clone MG1-45 (Bio Legend), UCHT-1, 5A6.E9, B1, TS8.2, 15D, B6, B3, TS-1, γ3.20, 7A5, and Zoledronate. FIG. 10 and FIG. 11 depict graphs illustrating activation and expansion of δ1 and δ2 T-cells respectively from PBMC. Cells were activated and expanded in media containing RPMI with 10% FBS, 100 IU/mL rhIL-2, glutamine and 1× penicillin streptomycin. On Day-7 after the initial stimulation, cells were passaged in fresh media and placed in a newly coated 24-well plate with the same antibodies at the same concentrations. Media in the re-stimulated cultures were replenished every 2-3 days until Day 13 and analyzed by flow cytometry.

Figure 12:
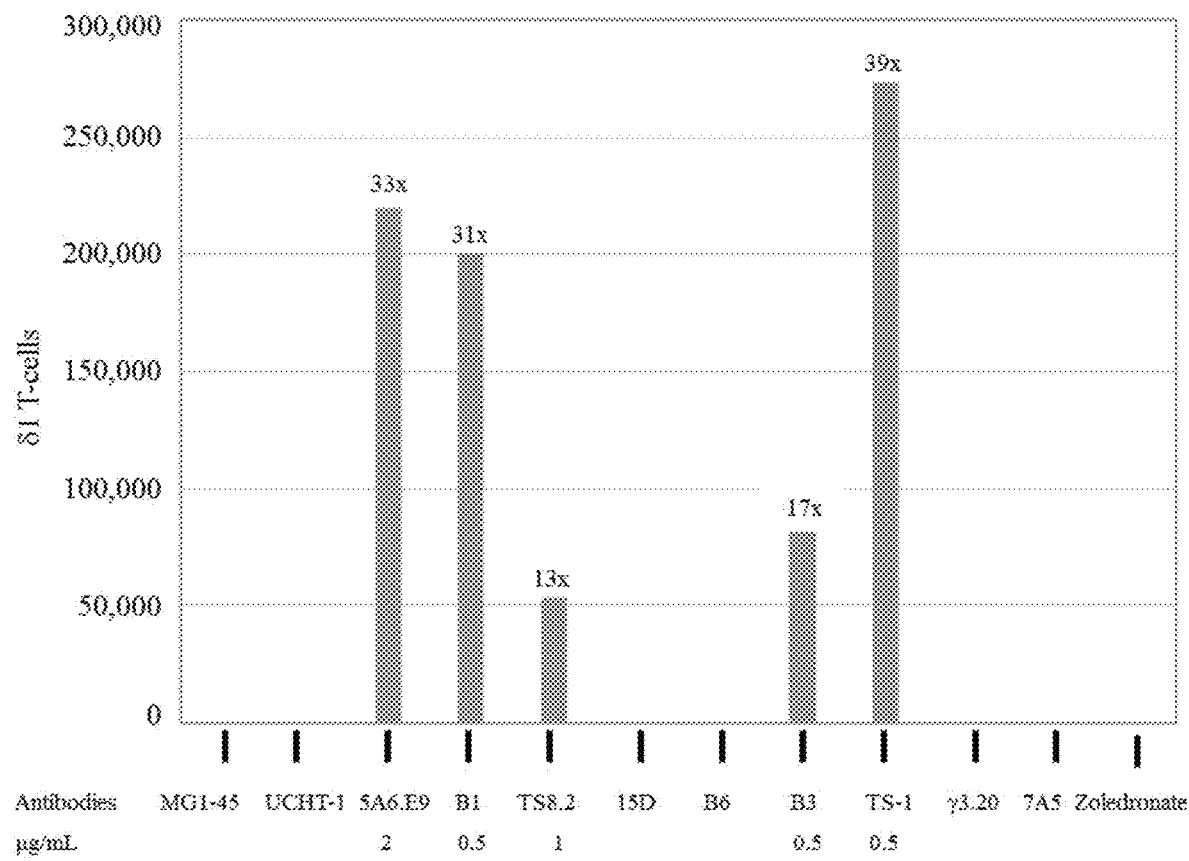
FIG. 12 depicts a graph illustrating fold expansion of δ1 T-cells from PBMC.
Figure 13:
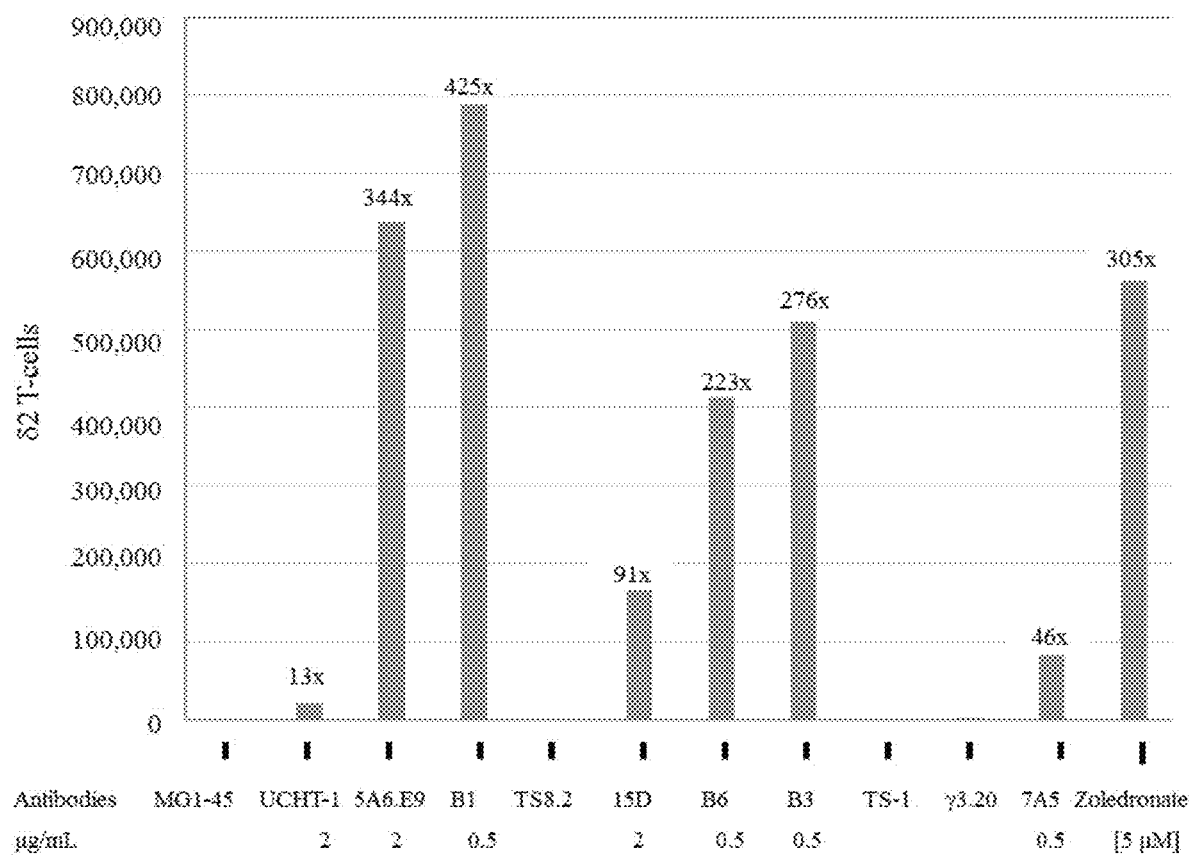
FIG. 13 depicts a graph illustrating fold expansion of δ2 T-cells from PBMC.

FIG. 12 illustrates the total number of δ1 T-cells, and FIG. 13 illustrates the total number of δ2 T-cells after 13 days of growth and expansion. The total number of γδ T-cells was calculated by multiplying the percentage δ1 and δ2 T-cells (as determined by flow cytometry using TS8.2-FITC and B6-PE, respectively) by the total viable cell number and subtracting the negative control values from δ1 and δ2 T-cell cells activated by the non-specific mouse IgG MG1-45.

Activation for cell expansion was obtained only when the antibodies were immobilized on the culture plates, with no detected expansion when these antibodies were added to the culture in soluble form, including in whole PBMC cell population (data not shown). Pan γδ TCR MAbs 5A6.E9 and B1 and activated the growth of both δ1 and δ2 cell populations. MAbs 15D and B6 induced selective growth of δ2 cell population. MAbs TS8.2 and TS-1 induced selective growth of δ1 cell population. Of interest is that although MAbs TS-1 and TS8.2 compete with each other in binding to cell surface TCR, TS-1 induced proliferation was 3-fold higher. Similarly, different extent of δ2 cell population proliferation induction was detected between antibodies B1, 5A6.E9, 15D, B6, and B3. This data indicates that unique epitopes are required to trigger a specific and robust expansion of γδ cell populations.

Example 22

Epitope Mapping of Activating γδ TCR MAbs

The specific activating epitopes on γδ TCR are identified as described below for TS-1 MAb. Similar steps are undertaken to identify the activating epitopes of the other γδ activating antibodies described herein.

First, the specific γδ recombination recognized by TS-1 is identified. The TS-1 Antibody (Thermo Fisher Scientific) was generated by immunization of mice with the human T cell acute lymphoblastic leukemia γδ cell line MOLT-13 (Brenner et al., US005260223A). We sequenced the MOLT-13 γδ TCR chains and identified the specific δ chain rearrangement to consist of Vδ1Dδ3Jδ1 gene segments. To determine if the TS-1 binding specificity is to the variable region of Vδ1 or if the binding site spans the TCR CDR3 region that includes the Vδ1-Jδ1 junction, and to assess the role of the γ chain in epitope recognition, an extensive set of γ and δ chains are cloned in pCI expression vector (Promega). Differently designed γ and δ TCR chains were ordered as synthetic gBlocks from IDT. The synthetic genes digested with NheI-NotI are cloned into the pCI-neo vector. The sequence of plasmid DNA from individual bacterial colonies is confirmed by sequencing.

Three Vδ1 gene segments differing in their Jδ region are designed (Jδ1, Jδ2 and Jδ3). In addition, Vδ2Jδ1 and Vδ3Jδ1 chains are ordered as synthetic genes and cloned similarly. Five δ TCR chains (Vδ1Jδ1, Vδ1Jδ2, Vδ1Jδ3, Vδ2 and Vδ3) to be co-transfected with γ TCR chains using Vγ2, Vγ3, Vγ4, Vγ5, Vγ8, Vγ9 and Vγ10 gene segments. 35 possible pairing combinations of γδ TCRs are transfected and expressed on the surface of 293 transfected cells. Transient transfection of 293 cells with pCI vectors encoding γδ chains is done using Lipofectamine 2000 (Invitrogen). Transfected 293 cells are characterized for expression of γδ TCR by Flow cytometry using a set of anti γδ TCR antibodies of different specificities. FACS analyses is done on a FACSCanto flow cytometer (BD Biosciences), and analyzed using FlowJo software (Tree Star). Once the specific γδ TCR chain pairing recognized by TS-1 mAb is identified, the specific binding epitope is characterized as a linear or as conformational dependent.

The ability of the antibody to bind to the denatured or the native TCR is confirmed by Western Blot analysis. Cell lysates of cells expressing TCR are prepared by homogenization in ice-cold modified RIPA Lysis Buffer with cocktail of protease inhibitors (Sigma). Protein concentration is determined by Bradford assay (Bio-Rad protein assay, Microplate Standard assay). The cell lysate is boiled for 5 min in 1×SDS loading buffer (50 mM Tris-HCl pH 6.8, 12.5% glycerol, 1% sodium dodecylsulfate, 0.01% bromophenol blue) containing 5% b-mercaptoethanol, and run on Polyacrylamide gel electrophoresis (PAGE). After electrophoresis, the separated molecules are transferred onto PVDF membrane. Next, the membrane is blocked and incubated with the antibody. A secondary fluorescently tagged antibody is used for detection with the aid of a fluorescence imaging system.

In case the binding to the δ chain is detected by Western blot analysis a set of synthetic-membrane-bound overlapping peptides derived from the polypeptide sequence of the reactive chain is used. (JPT peptide technology GmbH Germany). The peptide array consists of overlapping 12-mer peptides, with a single residue offset covering the Vδ1 entire sequence SPOTscan analysis is performed as follows. The membrane is washed three times in TBS and blocked overnight in blocking buffer (5% Low fat milk in TBST (0.05% Tween 20 in TBS). The membrane is washed in TBS and incubated with the TCS-1 MAb diluted in blocking buffer at 1 μg/ml for 3 hours at RT.

After washing of the membrane three times in TBS, bound MAb is detected with HRP conjugated goat anti mouse IgG (Jackson immunReaserch) diluted in blocking buffer for 2 hours at RT. The membrane is finally washed three times in TBS and incubated with signal development solution. The color reaction is allowed to develop for 10 to 40 min at RT. The binding site is represented by the sequence of the positive peptide spots.

Example 23

Epitope Mapping of Conformational Epitope

Epitopes that require the formation of disulfide bonds for proper folding/assembly of the antibody's binding epitope are known as conformational epitopes. The identification of critical binding residues can be performed by site-directed mutagenesis of the reactive V delta chain. Mutated chains are tested for loss of reactivity to a specific antibody. A residue encompassed by a binding site can be identified when mutagenesis of the critical residue in an otherwise unreactive chains leads to restored binding of the TS-1 antibody.

Random Ala scan of the reactive TCR chains can be used to assess change in binding affinity, lost recognition, or increased affinity by the TS-1 mAb.

Example 24

Epitope Mapping of Novel Modulators of γδ T-Cell Activation and Expansion

CD2 Epitopes:

The CD2 molecule consists of two extracellular immunoglobulin superfamily domains Ig-like V-type domain and Ig-like C-type domain, on which three major immunogenic regions have been described (Davis et al., Immunol Today 1996; 17: 177-187). Regions 1 and 2 are located in the first domain and region 3 is located in the second domain. Monoclonal antibodies (MAb) that recognize region 1 bind both resting and activated T-cells and can strongly inhibit the binding of CD58 to CD2. Monoclonal antibodies that recognize region 2 have similar binding properties but are not effective at blocking CD58 binding. Monoclonal antibodies that recognize region 3 recognize CD2 only on activated T-cells and do not block CD58 binding.

Mapping of the binding epitope of CD2 agonist MAbs is done by competition assays against CD58, the natural ligand of CD2 and activation assays. In addition, site directed mutagenesis of critical CD2 binding residues is that leads to loss of binding of CD58, is tested for MAbs binding. Examples of mutations include mutagenesis of the CD2 sequence at position 67 (K to R), 70 (Q to K), 110 (Y to D) and at position 111 (D to H). To design constructs for the mapping of the binding epitope of CD2 a sequence alignment of human and mouse CD2 using VectorNTI (Thermo Fisher) are performed. The alignments show a 50% sequence homology between human and mouse CD2. MAbs that bind the extracellular domain of human CD2 are not expected to cross react with the mouse CD2. To identify the binding epitopes, we generate domain swapping of mouse/human chimeric CD2 constructs. In such constructs, the human N-terminal Ig-like V-type domain (residues 25-128) is replaced with mouse residues (23-121) in expression vector expressing the extra cellular domain of CD2. Chimeric cDNA species are transiently transfected into CHO or 293 cells. Human wildtype CD2 and human mouse chimeric constructs are expressed on the surface of CHO cells. Chimeric CD2 Cell-surface expression is analyzed by FACScanto. Binding or loss of binding to chimeric molecule is detected by flow cytometry and validated by activation assays.

NKG2D Epitopes:

Epitope mapping of activating MAbs against NKG2D is tested by the ability of anti-hNKG2D antibody to reduce or block NKG2D interactions with one or more of its ligands, (MICA/MICB) or by competition with an antibody known to block hNKG2D ligand interaction. Agonist MAb is identified by its ability to reduce NKG2D-mediated activation of NK or T-cells. This can be evaluated by typical cytotoxicity assays, addition of ligand-blocking antibodies, or by blocking γδ T-cells mediated killing of MICA-expressing tumor cells in a dose-dependent fashion.

CD27 Epitopes:

Epitope mapping of agonist antibodies against CD27 is done by functional assay and their ability to block the interaction between human CD27 and its natural ligand human CD70. CD27 expressing cells are incubated for 30 min with 5 μg of MAbs at 4° C., after which 1 μg of biotinylated CD70 is added to the tube. The mixture is incubated for another 15 min at 4° C. before washing. Next, cells are incubated for 30 min with a mixture of streptavidin-PE (for detection of CD70 ligand binding) followed by several washing steps and analysis using FACS. Blockage of CD70 binding indicates that the MAb and CD70 share the same epitope.

Example 25

Characterization of TCR VS Repertoire of a Population of Expanded γδ T-Cells Clonal diversity of expanded γδ T-cells from individual donors is assessed with polymerase chain reaction (PCR). The clonal diversity of freshly isolated PBMC from healthy donors is compared to the clonal diversity of cultures that are stimulated for 7 and 13 days with different activation agents described herein, including anti-TCR specific antibodies, ligand, and lectins.

RNA from the aforementioned γδ T-cells is extracted, reverse transcribed into cDNA, and amplified by PCR using Vδ1, Vδ2, and Vδ3-specific primer pairs. Vδ1 forward primer (5'ATGCTGTTCTCCAGCCTGCTGTGTGTATTT 3'; SEQ ID NO: 1) Vδ2 forward primer (5'ATGCAGAGGATCTCCTCCCTCATCCATCT 3'; SEQ ID NO: 2) and Vδ3 forward primer (5'ATGATTCTTACTGTGGGCTTTAGCTTTTTG 3'; SEQ ID NO: 3) were used in combination with A Cδ reverse primer (5'CTTGGGGTAGAATTCCTTCACCAGACAAGC3'; SEQ ID NO: 4) to amplify 500 bp DNA fragments.

The γ chain was amplified in separated RT-PCR reaction using Vγ specific primers to amplify Vγ2, Vγ3, Vγ4, and Vγ5 (5' GGTGCTTCTAGCTTTCCTGTCTCCTGC3' (SEQ ID NO: 10)), Vγ8 (5'ATGCTGTTGGCTCTAGCTCTGCTTCTA3' (SEQ ID NO: 11)) and Vγ9 (5'ATGCTGTCACTGCTCCACACATCAACG3' (SEQ ID NO: 12)) Vγ primers are paired with the Cγ reverse primer (5'GGAAGAAAAATAGTGGGCTTGGGGGAA3' (SEQ ID NO: 13)), The γ reverse primer based on consensus sequence of the Cγ1 and Cγ2. PCR fragments are cloned and the nucleotide sequence of 80 independent Vγ inserts are obtained. The Vδ, Dδ and Jδ junctional sequences are analyzed, together with CDR3 sequence alignment.

Example 26

MAbs and Related Targeting Constructs for Engineering of γδ T-Cells

The human CD20 gene is obtained from a cDNA clone (Origene Technologies, Inc., 6 Taft Court, Suite 100, Rockville, Md. 20850). The CD20 gene is amplified using the forward primer (5' ATGACAACACCCAGAAATTCAGTAAATGG3' (SEQ ID NO: 14)) and the reverse primer (5' TCAAGGAGAGCTGTCATTTTCTATTGGTG3' (SEQ ID NO: 15)) the amplified CD20 cDNA is incorporated into pCDNA3.4 (Thermo Fisher Scientific) as a high expression vector for mammalian cells, and transfected into CHO cells as the host cells. Recombinant CHO cells (CD20/

CHO cells) expressing CD20 molecules at a high level on their cell surfaces are identified by FACS analysis.

The CD20/CHO cells are used to immunize BALB/C mice or transgenic mice engineered to produce fully human antibodies as described in Jakobovits and Bornstein (Jakobovits Curr. Opin. Biotechnol. 1995 6:561-6; Bornstein et al., Invest New Drugs. 2010 28:561-74). Antibodies with high affinity and specificity towards human CD20 are screened by FACS assays. Mouse antibodies are humanized by CDR grafting (Kim and Hong Methods Mol Biol. 2012; 907:237-45. Human single domain CD20 antibodies are also generated from mice or rats engineered to produce human heavy chain single domain antibodies (Janssens et al., PNAS 2006 vol. 103:15130).

The gene coding for the high affinity/specificity CD20 antibody described above is cloned into the MSGV1 retroviral vector backbone or the pCAG lentiviral vector. VH and VL domains are cloned either from the mouse hybridoma expressing the selected MAb, or from humanized antibody chains. γδ T-Cells are engineered with the CD20 MAbs described herein.

Example 27

TCR Constructs for Engineering of γδ T-Cells

Constructs expressing TCRs comprising sequences of highly reactive αβ TCR chains are isolated from T-lymphocytes expressing NY-ESO-1-MHC specific peptide complexes. The NY-ESO-1-MHC specific peptide complexes induce potent in vitro and in vivo anti-tumor activity against various NYES0-1-expressing tumors.

The highly reactive αβ TCR chains are isolated from melanoma, sarcoma patients or from mice bearing patient-derived xenografts derived from human melanoma or sarcoma tumors. Alternatively, the TCR is derived from mice altered to have a humanized immune system that expresses NY-ESO-1 peptides or NYESO-1-peptide complexes (See Gonzales et al., Immunol Res. 2013 57: 326-334; Boucherma etal., J Immuno. 2013. 191; 583-593; Liang-PingL. Et al., Nature Med. 2010, 16:1029-1035). T-cells that recognize epitopes of the NY-ESO-1-in the context of the dominant class I alleles HLA-A*02 (for example, peptide SLLMWITQC Residues 157-167 (SEQ ID NO: 16)) and dominant HLA-A*01-associated peptide are identified.

Sequences of TCRα and TCRβ transcripts are generated αβ reverse transcription-polymerase chain reaction (RT-PCR) using the One step RT-PCR kit (Qiagen Hilden Germany) according to the manufacturer's suggestions. First strand cDNA is generated from RNA isolated from the reactive T-cell. Total RNA is extracted with TRIzol Total RNA Isolation Reagent (Invitrogen Life Technologies) from CTL clones. Amplification of TCR α and β chains is done by a set of degenerate primers that can bind to highly conserved region of the TCR α and β chain V regions centered around the tryptophan-tyrosine residues at amino acid positions 34 and 35 (Kabat numbering) are used in combination with the α and β constant region reverse primers (Moonka and Loh Journal of Immunological Methods 169 (1994) 41-51). Amplified PCR fragments are gel purified and directly sequenced. Sequence information is used to design PCR primers suitable for cloning of the individual full-length cDNAs.

TCRs genes are cloned and inserted into MSGV-based retroviral vectors and full-length cDNAs amplified from selected T cells. Retroviral vectors encoding both α and β chains of wild-type NY-ESO-1-reactive human TCR are constructed using a MSGV1 backbone Linking of the TCRα and TCRβ chains is done via an internal ribosome entry site (IRES) element in one construct, or by separation using a cleavable picorovirus peptide sequence.

Retroviral supernatants are generated by co-transfecting 293 cells that stably expressed MMLV gag and pol proteins with each MSGV1 TCR vector and a vector encoding the endogenous virus retroviral envelope protein using Lipofectamine 2000 (Invitrogen) as described previously or by electroporation using the Nucleofector (Lonza). Supernatants are collected at day 2 and 3 post-transfection and were diluted 1:1 with fresh DMEM containing 10% FCS. Engineered γδ T-cells are capable of properly express the genes encoding the TCR α and β chains without any further manipulation.

Example 28

Engineering γδ T-Cells with an αβ TCR Construct

A polynucleotide comprising an αβ TCR (tumor recognition moiety) is cloned from T-cells selected to be specific to the desired antigen using standard techniques. Isolated endogenous wild-type γδ T-cells are grown with methods described in previous examples to at least $6 \times 10^6$ cells prior to infection with the retrovirus or a lentivirus comprising an expression cassette encoding the tumor recognition moiety. A standard protocol for viral infection can be used to introduce the vector system into the wild-type γδ T-cell. Expression of the selection marker is used to select cells that have been successfully transfected.

The expression of the engineered αβ TCR can be evaluated by flow cytometry and/or by quantitative QRT-PCR and by functional assays with target cells for cytotoxicity and cytokine secretion. The expression of the engineered activation domain can also be evaluated by flow cytometry and/or by quantitative qRT-PCR. The number of engineered γδ T-cells expressing a cell surface marker of interest is determined by flow cytometry. The engineered γδ T-cell is further engineered with a suitable methodology described herein, such as the CRISPR-Cas, talen, meganucleases, zinc finger, or sleeping beauty transposon technologies to delete an exon associated with an HLA gene or a β2M gene.

Example 29

Engineering γδ T-Cells with CAR and TCR Constructs

γδ T-cells are transduced with retro- or lenti-viral based vectors to express targeting moieties that can direct the engineered γδ T-cells to specifically recognize tumor cells and get activated to kill it. The transduced targeting moieties include MAbs directed against tumor-specific surface proteins or tumor-specific intracellular peptides. γδ T-cells are also engineered with high affinity TCRs directed to peptide-MHC complexes.

Alternatively, cells can be engineered via transduction with non-viral vectors.

Example 30

Engineering of Isolated γδ T-Cells with Targeting Moieties

CAR construct design comprises of different main functional domains, a target moiety that recognizes a protein or a MHC associated peptide of interest displayed on a tumor cell, a short spacer that connects the extracellular receptor targeting element to the transmembrane domain, which transverses the cell membrane and connects to the intracellular activation signaling domain.

The target moiety receptor expressed on the surface of a γδ T-cell will be designed to specifically bind to a target protein that is expressed on a cancer cell. Tumor recognition moieties will be designed against leukemia targets including CD19, CD30, CD22, CD37, CD38, CD56, CD33, CD30, CD138, CD123, CD79b, CD70, CD75, CA6, GD2, alphafetoprotein (AFP), carcinoembryonic antigen (CEA), CEACAM5, CA-125, MUC-16, 5T4, NaPi2b, ROR1, ROR2, 5T4, PLIF, Her2/Neu, EGFRvIII, GPMNB, LIV-1, glycolipidF77, fibroblast activating protein, PSMA, STEAP-1, STEAP-2, mesothelin, c-met, CSPG4, Nectin-4, VEGFR2, PSCA, folate binding protein/receptor, SLC44A4, Cripto, CTAG1B, AXL, IL-13R, IL-3R, and SLTRK6.

The target moiety receptor can be derived from a portion of an antibody specific to tumor glycoprotein expressed on the surface of tumor cells, or alternatively the engineered receptor can be derived from a TCR receptor with a known specificity or an antibody recognizing a specific peptide sequence derived from intracellular tumor specific antigen presented on the on the surface in association with MHC complex including gp100, MART1, Tyrosinase, SSX2, SSX4, NYESO-1, epithelial tumor antigen (ETA), MAGEA family genes (such as MAGE3A. MAGE4A), KKLC1, mutated ras, βraf, p53, MHC class I chain-related molecule A (MICA), MHC class I chain-related molecule B (MICB), HPV, or CMV. Such high affinity T-cell receptor like tumor recognition moieties will recognize peptide-MHC complex with a high degree of specificity.

Example 31

Targeting Moiety Constructs with a Spacer and a Transmembrane Domain

Different spacers will be engineered into a tumor recognition moiety construct in order to optimize the potency of an engineered T-cell towards a cancer cell. The size of each spacer will vary according to the size of the target protein, the epitope recognized by the receptor, the size of the engineered tumor recognition moiety and the affinity of the receptor. Spacers that can accommodate conformational changes including sequences of human IgG, CD8a and CD4 hinge region.

Spacers that are tested consist of Gly, Ser, and Thr amino acids used at different lengths (from 19 to 9 residues) in order to provide chimeric receptor with improved binding affinity properties. The hinge and transmembrane portions of each construct is derived from the CD8a sequence (residues 117 to 178 of human CD8a) or alternatively the human IgG1 hinge-Fc cDNA with CD28 transmembrane domain (residues 153-179).

Example 32

Targeting Moiety Constructs with Co-Stimulatory Domains

Different co-stimulatory domains will be engineered into a construct comprising a tumor recognition moiety. A co-stimulatory domain comprising a CD28, 4-1BB, CD2, CD27, NKG2D, CD161, CD30, JAML, CD244 or CD100 costimulatory signaling domain is engineered into a γδ T-cell to mimic a "second signal" that amplifies the activation through the chimeric receptor, leading to a more robust signal to multiply and kill the cancer cell.

The cytoplasmic region is derived from the endodomains of αβ and/or γδ T-cell co-stimulatory molecules including: CD28 (residues 180-220), CD137 (residues 214-255), ICOS (residues 165-199) CD27 (residues 213-260) NKG2D (Residues 1-51), JAML (residues 297-394) CD2 (residues 236-351), CD30 (residues 408-595) OX40 (Residues 1-23), HVEM (residues 224-283), or CD46 molecules. The optimal constructs are selected based on the degree of activation of the engineered γδ T-cell populations for induced cell cytotoxicity and based on the degree of cytokine secretion in-vitro and in-vivo.

Example 33

Targeting Moieties Comprising CD3 Activating Domain

The intracellular CD3ζ (residues 52-164) containing three ITAM domains (ITAM1: APAYQQGQNQLYNELNLGR-REEYDVLDKR, (SEQ ID NO: 5); ITAM 2: PQRRKNPQEGLYNELQKDKMAEAYSEIGM, (SEQ ID NO: 6); and ITAM3: ERRRGKGHDGLYQGLSTATKDTY-DALHMQ, (SEQ ID NO: 7) was cloned.

The intracellular domain of TCRζ was amplified using primers 5' AGAGTGAAGTTCAGCAGGAGCGCA-3' (SEQ ID NO: 8) and the reverse primer 5' CTCGAGTGGCTGTTAGCCAGA-3' (SEQ ID NO: 9).

The CAR constructs are generated by multistep overlap extension PCR. The products were fused in a separate PCR reaction driven by primers tailed with the Platinum Taq DNA Polymerase High Fidelity kit (Invitrogen), using the Overlap extension polymerase chain reaction protocol, The DNA encoding the full-length construct was ligated into MSGV1 Retroviral Vector. The construct provides a CAR targeting moiety comprising a CD3ζ activating domain.

Example 34

Engineering γδ T-Cells with More than One Recognition Moiety

γδ T-cells are transduced with more than one construct comprising a tumor recognition moiety, including a TCR and a MAb directed to the same intracellular tumor-specific protein. Each construct is selected to recognize a specific peptide in the context of different MHC haplotypes, such as A2 and A1, antibodies directed to different targets expressed on the same tumor cells or antibodies directed to different epitopes on the same target.

Example 35

In Vitro Expansion of Engineered γδ T-Cells

Engineered γδ T-cells are grown and expanded with an appropriate tissue culture media, such as the tissue culture media described in previous examples. The Engineered γδ T-cells are grown exponentially to about $1 \times 10^6$ in a 5% $CO_2$ incubator at 37° C. with or without stimulation by an external antigen and without co-culture with APCs or aminophosphates.

Example 36

Functional Characterization of Cytokines Released by Activated Engineered and Non-Engineered γδ T-Cells The expression of IFN-γ, TNF-α (R&D Systems), IL-1β, IL-2, (Biosource International), IL-12 (Diaclone Research), and IL-18 will be measured using commercial enzyme-linked immunosorbent assay (ELISA) kits. The enzyme-linked immunosorbent assays will be performed according to the manufacturers' instructions. The amount of cytokine will be measured at different time points (from 24 to 72 hours) in a polystyrene 96-well plate (Maxisorb, Nunc) coated with a monoclonal mouse IgG1 against the human cytokine, at a concentration of 1 µg/ml in 0.05 M sodium bicarbonate buffer overnight at 4° C. After washing with PBS containing 0.05% Tween 20 the plate will be blocked with 3% bovine serum albumin (BSA, wt/vol, Sigma) in PBST for 1 h at 37° C. A standard (recombinant human Cytokine from R&D) and supernatant from γδ cultures samples will be added and the plate will be incubated at RT for 2 h. Detection with a matched antibody pairs in relation to recombinant human cytokine standards.

Example 37

Identifying Co-Stimulatory Agents

The ability of different co-stimulatory agents to support activation, expansion and viability of engineered and non-engineered γδ T-cells is tested by adding co-stimulatory agents to whole PBMCs or enriched engineered and non-engineered γδ T-cell populations. Co-stimulatory agents are added in a soluble or immobilized form to different activating agents, including anti γδ TCR specific MAbs. Human PBMCs purified from buffy coats of healthy donors as described in previous examples or lymphocytes isolated from tissues are plated at $2 \times 10^6$ in 1 mL of complete RPMI-1640 media supplemented with 100 IU/mL rhIl-2 in 24-well flat-bottom tissue with 2-10 µg of anti γδTCR antibody in the presence or absence of soluble or immobilized agonistic antibodies to CD2, CD27, CD28, CD30, CD137, ICOS, CD161, CD122, CD244, and NKG2D, or stimulating ligands including, CD70-FC (ligand to CD27) MICA, MICB and ULBP (ligands to NKG2D), 4-1BB (ligand to CD137), and Pilar 9 (ligand to CD161).

Example 38

Cytokine Support Activation

The ability of different cytokines to support activation, expansion and viability of engineered and non-engineered γδ T-cells is tested by adding cytokines to whole PBMCs or enriched engineered and non-engineered γδ T-cell populations. To test cytokine activation support, various cytokines are individually added to separate cell cultures every 3 days at 100 IU/mL. The cytokines that are tested include IL-2, IL-7, IL-12, IL-15, IL-33, IL-21, IL-18, IL-19, IL-4, IL-9, IL-23, and IL1β. After the end of a select time period, a sample of cells is harvested and the composition of the cell population, i.e., percentages of γδ T-cells, αβ T-cells, B-cells, and NK cells is determined by flow cytometry.

Cells are kept in culture and expansion of select populations is tested at day 14 and day 21.

Example 39

In-Vitro Cytotoxicity Assay of Engineered and Non-Engineered γδ T-Cells In-Vitro In vitro cytotoxicity assay of engineered or non-engineered γδ-T cells is determined by 4 different cytotoxicity assays: 1) Tumor cell Lysis; 2) cytokine release by activated T cells; 3) LDH assay; and 4) Activation of CD107a expression. A variety of human tumor cell lines or human tumor-derived cells (patient derived xenograft tumor lines) derived from but not limited to colon, breast, ovary, kidney, head and neck, oral cavity, pancreas and liver cancer are used as target cells. Normal human mammary epithelial cells (HMEC) are used as a negative control. Briefly, proliferating target cells are seeded at $1 \times 10^4$ cells per well in a 96 well plate. After 24 hours, medium is removed and activated γδ-T cells are added in RPMI medium (RPMI-1640 from Corning, 10% Hyclone fetal bovine serum, 2 mmol/L L-glutamine, 100 U/mL penicillin, 100 U/mL streptomycin) at an effector to target ratio of 20:1 or 40:1 and incubated for 5 hours at 37° C. in humidified atmosphere for 5% $CO_2$. Cytokine released by engineered and non-engineered γδ-T cells, following this incubation is determined by collecting the co-culture supernatant and quantifying for secretion of cytokines, including IFN-γ, IL2, TNFα, IL-6, and IL1β using a commercially available ELISA kit (BioLegend). LDH assay is performed using a LDH cytotoxicity detection kit (Roche) following manufacturer's instructions. Finally, CD107a expression is determined by adding 5 ul of CD107a antibody conjugated to Cy7PE (BioLegend) following the addition of γδ-T cells to targets cells. Plate is briefly centrifuged and incubated for 1 hour at 37° C. in humidified atmosphere for 5% $CO_2$ and then 8.5 µL of a 1:50 dilution of Golgi stop BD Biosciences (BD) added. Cells were incubated for an additional 2 hours at 37° C. in humidified atmosphere for 5% $CO_2$. Following this incubation, cells are collected on ice, washed once with cold HBSS and stained with 1 ul of zombie aqua (BioLegend) amine dye to determine live cell population in 100 ul of HBSS. Cells are washed in FACS staining medium (FSM; HBSS containing 2% fetal bovine serum) and resuspended in 100 ul of FSM containing saturating amounts of antibodies, including Vδ1 antibodies conjugated to FITC (clone TS8.2 from ThermoFisher) and Vδ2 antibodies conjugated to PE (clone B6 from BioLegend). Antibodies are incubated with cells for 30 minutes on ice and then washed with an excess amount of HBSS. Stained populations are collected on a BD FACSCanto II and analyzed using FlowJo v10.1 software.

Example 40

Anti-Tumor Activity of Expanded γδ T-Cells In-Vitro

The cytotoxic activity against various tumor cell lines and primary tumor cells are tested at effector to target ratio between 1:1 to 40:1. Lysis of tumor cell lines and primary tumor cells are measured by detecting the release of intracellular enzymes lactate dehydrogenase. The percentage of γδ T-cells expressing engineered tumor recognition moieties in the culture is measured by flow cytometry, ELISA and/or ELISPOT assays.

Example 41

In Vivo Anti-Tumor Activity

Cohorts of immune-deficient mice engrafted with human tumor xenografts, or huPBMC-NOG (Taconic) mice, or mice with humanized immune system as described above, are injected subcutaneously or orthotopically with cells derived from patient-derived tumor or tumor cell lines, including cancers of the colon, breast, ovary, kidney, head and neck, prostate, bladder, oral cavity, pancreas and liver, and allowed to reach an average size of 100 $mm^3$. Enriched or isolated γδ-T cells, either nave or engineered, are injected intravenously into mice or directly into the tumor at a range of doses. Tumor regression is defined as a reduction in tumor volume after γδ-T cell dosing, and compared to untreated and standard of care for the specific indication. In some experiments nave or engineered γδ T-cells are labeled with GFP or luciferase and injected to tumor-bearing mice to follow their persistence and homing. At the end of the study, tumors are harvested and GFP positive cells were analyzed by flow cytometry and immunohistochemistry.

Example 42

Cryopreservation of γδ T-Cells in Freeze Media to Generate Cell Banks for Further Processing Non-modified γδ T-Cells will be formulated in freezing media and placed in cryogenic storage units such as liquid nitrogen freezers (−195° C.) or ultra-low temperature freezers (−65° C., −80° C. or −120° C.) for long-term storage. The freeze media will contain dimethyl sulfoxide (DMSO), sodium chloride (NaCl), dextrose, dextran sulfate or hydroyethyl starch (HES) with physiological pH buffering agents ranging between 6.5 and 7.5.

The cryopreserved γδ T-cells will be thawed and further processed by stimulation with antibodies, proteins, peptides, and cytokines. The cryopreserved γδ T-Cells will be thawed and genetically modified as previously described in this application. The engineered γδ T-cells will be further cryopreserved to generate cell banks in quantities of 10, 100, 200 vials at $10^6$ to $10^8$ cells per mL in freeze media.

Example 43

Alternative Cryopreservation of γδ T-Cells in Freeze Media to Generate Cell Banks for Further Processing Other cryoprotectants are added to the cryopreservation support described in the previous example to provide nutritional support and biophysical cell protection against lysis during the freezing and thawing process. These include D-glucose, mannitol, sucrose, adenine, guanosine, recombinant human albumin, citrate, ant-coagulant, Benzonase, DNase, propylene glycol, ethylene glycol, 2-methyl-2,4-pentanediol. Additional additives designed to provide buffering capacity for high cell density frozen product include inorganic phosphate, sodium bicarbonate and HEPES.

Example 44

Cryopreservation of γδ T-Cells in Freeze Media to Generate Cell Banks for Further Processing Initial freezing of γδ T-cells are performed in a temperature controlled ramp designed to achieve a freezing rate of between −0.1° C. to −5° C. per minute using a controlled rate freezer (e.g. CryoMed Controlled Rate Freezer) or a mechanical −70° C. freezer with appropriately insulated racking system to deliver the desired freeze rate. The frozen cells are placed in −70° C. freezers for short-term storage of up to 30 to 60 days. The frozen cells are placed in liquid $N_2$ storage tanks for longer-term storage of up to 12, 24, 36 and 48 months while maintaining γδ T-cell number and cell functions without deterioration as measured by methods described in earlier sections.

The cryopreserved cells described in this example will be thawed and further stimulated and expanded in suitable closed vessels such as cell culture bags and/or bioreactors to generate suitable quantities of engineered γδ T-cells for administration to a subject.

Example 45

Formulation of γδ T-Cells for Direct Infusion into Patients

Engineered γδ T-cells are concentrated by centrifugation and/or membrane dia-filtration to between $5 \times 10^6$ cells/mL and $10^8$ cells/mL in physiological buffer containing cryoprotective excipients and placed in cryogenic storage units such as liquid nitrogen, or ultra-low temperature freezers for long-term storage.

Example 46

Treatment of a Human Subject Afflicted with Cancer

Fresh or frozen Engineered γδ T-cells are thawed at bedside and intravenously infused into human subjects. About 1 cell per kilogram to about $1 \times 10^{10}$ cells per kilogram engineered γδ T-cells are infused into the human subject over a 30-60 minute period of time. The engineered γδ T-cells are administered with or without the aid of the co-stimulatory cytokine IL-2 or other cytokines Optionally, the procedure is repeated. In vivo expansion of the γδ T-cells in the subject is measured by flow cytometry.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An ex vivo method for producing an expanded δ1 γδ T-cell population, comprising
   a) providing a sample of a human subject, wherein the sample comprises γδ T-cells,
   b) selectively expanding
      the δ1 γδ T-cells by culturing cells of the sample in the presence of a cytokine selected from IL-2, IL-7, IL-9, IL-12, IL-15, IL-18, IL-21, and IL-33, and at least one antibody which selectively expands the δ1 γδ T-cells to produce a culture comprising the expanded δ1 γδ T-cell population;
   wherein the culture conditions do not comprise IL-4 and said cells have not been exposed to exogenous IL-4 prior to expansion, and wherein:
      said at least one antibody which selectively expands δ1 γδ T-cells is selected from TS-1, TS8.2 or R9.12 antibodies which bind to a specific epitope of a δ1 TCR chain, to selectively expand δ1 T-cells; and
   wherein the culture comprising the expanded γδ T-cell population comprises a percentage of δ1 γδ T-cells, wherein the percentage of δ1 γδ T-cells is greater than 60% of total viable cells of the culture, optionally wherein the percentage of δ1 γδ T-cells is greater than 80% or 90%, optionally, of total viable cells of the culture.

2. The method of claim 1, wherein said method does not comprise expanding the γδ T-cell population by an antigen presenting cell, an aminophosphate, or a nitrogen containing bisphosphonate.

3. The method of claim 1, wherein said at least one antibody which selectively expands δ1 γδ T-cells are immobilized on a surface.

4. The method of claim 1, wherein said sample is selected from a peripheral blood sample, a cord blood sample or a tumor.

5. The method of claim 1, wherein the expanded γδ T-cell population is further formulated for administration to a subject.

6. The method of claim 1, wherein the expanded γδ T-cell population includes a therapeutically effective amount of γδ T-cells.

7. The method of claim 6, wherein said γδ T-cell population is engineered to stably express one or more tumor recognition moieties.

8. The method of claim 7, wherein the expanded γδ T-cell population comprises at least about $1 \times 10^7$ γδ T-cells.

9. The method of claim 1, wherein said cytokine is selected from the group consisting of IL-2, IL-7, IL-15, and IL-21.

10. The method of claim 9, wherein said cytokine is selected from the group consisting of IL-2, IL-7, and IL-15.

11. The method of claim 1, further comprising:
enriching the γδ T-cells prior to selectively expanding the δ1 γδ T-cells.

12. The method of claim 11, wherein the enriching includes removing one or more of red blood cells, NK cells, αβ cells, B cells, monocytes, and macrophages.

* * * * *